US012611412B2

(12) United States Patent
DeBenedetti et al.

(10) Patent No.: US 12,611,412 B2

(45) Date of Patent: Apr. 28, 2026

(54) TARGETING THE TLK1/NEK1 AXIS IN PROSTATE CANCER

(71) Applicant: Board of Supervisors of Louisiana State University and Agricultural and Mechanical College, Baton Rouge, LA (US)

(72) Inventors: Arrigo DeBenedetti, Bossier City, LA (US); Siddhant Bhoir, Gujarat (IN); Vibha Singh, Shreveport, LA (US); Javeena Hussain, Gujarat (IN); Rupesh Chikhale, Manchester (GB); Richard Bryce, Manchester (GB); Sivapriya Kirubakaran, Gujarat (IN)

(73) Assignee: Board of Supervisors of Louisana State University and Agricultural and Mechanical College, Baton Rouge, LA (US)

( * ) Notice: Subject to any disclaimer, the term of this patent is extended or adjusted under 35 U.S.C. 154(b) by 22 days.

(21) Appl. No.: 18/509,586

(22) Filed: Nov. 15, 2023

(65) Prior Publication Data

US 2024/0189321 A1 Jun. 13, 2024

Related U.S. Application Data

(63) Continuation of application No. 16/834,061, filed on Mar. 30, 2020, now Pat. No. 11,826,369.

(60) Provisional application No. 62/825,800, filed on Mar. 29, 2019.

(51) Int. Cl.
*A61K 31/5415* (2006.01)
*A61K 31/167* (2006.01)
*A61P 35/00* (2006.01)

(52) U.S. Cl.
CPC ........ *A61K 31/5415* (2013.01); *A61K 31/167* (2013.01); *A61P 35/00* (2018.01)

(58) Field of Classification Search
CPC .... A61K 31/5415; A61K 31/167; A61P 35/00
See application file for complete search history.

(56) References Cited

FOREIGN PATENT DOCUMENTS

WO WO-2013119825 A1 * 8/2013 ......... A61K 38/2013

OTHER PUBLICATIONS

DrugAnalogs, 2025, https://www.albion.edu/wp-content/uploads/2021/03/DrugAnalogs.pdf.*

Jiang, J., P. Jia, Z. Zhao, and B. Shen. 2014. Key regulators in prostate cancer identified by co-expression module analysis. BMC Genomics 15:1015.

Karanika, S., T. Karantanos, L. Li, P. G. Corn, and T. C. Thompson. 2015. DNA damage response and prostate cancer: defects, regulation and therapeutic implications. Oncogene 34:2815-2822.

Liu, S., C. K. Ho, J. Ouyang, and L. Zou. 2013. Nekl kinase associates with ATR-ATRIP and primes ATR for efficient DNA damage signaling. Proc Natl Acad Sci U S A 110:2175-80.

Moraes, E. C., G. V. Meirelles, R. V. Honorato, A. de Souza Tde, E. E. de Souza, M. T. Murakami, P. S. de Oliveira, and J. Kobarg. 2015. Kinase inhibitor profile for human nekl, nek6, and nek7 and analysis of the structural basis for inhibitor specificity. Molecules 20:1176-91.

Mortensen, P. B. 1989. The incidence of cancer in schizophrenic patients. J Epidemiol Community Health 43:43-7.

ProstateCancerPrevention, 2022, https://www.mayoclinic.org/diseases-conditions/prostate-cancer/in-depth/prostate-cancer-prevention/art-0045641#:~:text=There's%20no%20proven%20prostate%20cancer,interested%20in%20prostate%20cancer%20prevention. *.

Ronald, S., G. Sunavala-Dossabhoy, L. Adams, B. Williams, and A. De Benedetti. 2011. The expression of Tousled kinases in CaP cell lines and its relation to radiation response and DSB repair. Prostate 71:1367-73.

Ronald, S., S. Awate, A. Rath, J. Carroll, F. Galiano, D. Dwyer, H. Kleiner-Hancock, J.M. Mathis, S. Vigod, and A. De Benedetti. 2013. Phenothiazine Inhibitors of TLKs Affect Double-Strand Break Repair and DNA Damage Response Recovery and Potentiate Tumor Killing with Radiomimetic Therapy. Genes Cancer 4:39-53.

Shaheen, F. S., P. Znojek, A. Fisher, M. Webster, R. Plummer, L. Gaughan, G. C. Smith, H. Y. Leung, N. J. Curtin, and C. N. Robson. 2011. Targeting the DNA double strand break repair machinery in prostate cancer. PLOS One 6: e20311.

Singh, V., P. Jaiswal, I. Ghosh, H. K. Koul, X. Yu, and A. De Benedetti. 2019. Targeting the TLK1/NEK1 DDR axis with Thioridazine suppresses outgrowth of Androgen Independent Prostate tumors. International journal of cancer (in press DOI: 10.1002/ijc.32200)).

StructuralAnalog, 2022, https://en.wikipedia.org/wiki/Structural_analog. *.

Torrey, E. F. 2006. Prostate cancer and schizophrenia. Urology 68:1280-3.

Wu, C. S., Y. T. Tsai, and H. J. Tsai. 2015. Antipsychotic Drugs and the Risk of Ventricular Arrhythmia and/or Sudden Cardiac Death: A Nation-wide Case-Crossover Study. J Am Heart Assoc 4.

* cited by examiner

*Primary Examiner* — Sun Jae Yoo

(74) *Attorney, Agent, or Firm* — Jones Walker LLP

(57) ABSTRACT

A method of treating prostate cancer in a patient comprising administering to the patient a pharmaceutical composition including a first therapeutic including a TLK1B inhibitor, or a pharmaceutically acceptable salt, solvate, ester, amide, clathrate, stereoisomer, enantiomer, prodrug or analog thereof, and a second therapeutic including an antiandrogen or a pharmaceutically acceptable salt, solvate, ester, amide, clathrate, stereoisomer, enantiomer, prodrug or analog thereof.

20 Claims, 61 Drawing Sheets
(26 of 61 Drawing Sheet(s) Filed in Color)

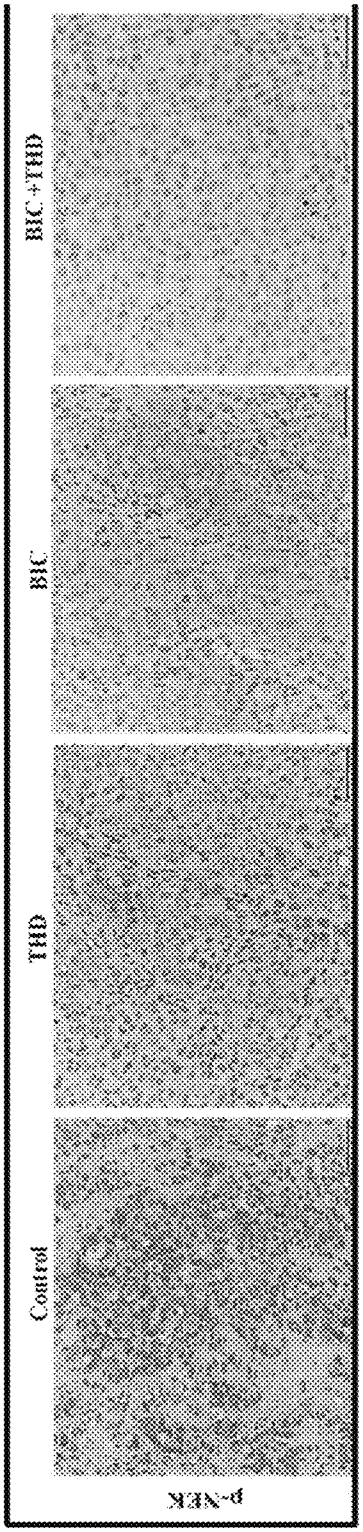
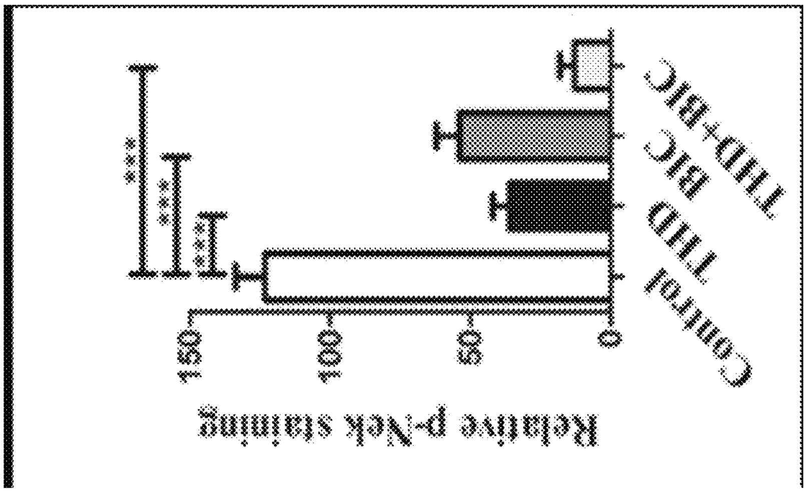
FIG. 1E

FIG. 9D

Docking score (ChemGauss4) and computed MM/GBSA binding free energy for predicted pose of ligand bound to TLK1 or D2 receptor proteins. Standard deviations in parentheses. Energies in kcal/mol.

| Complexes | Dock Score | $\Delta G_{bind}$ |
|---|---|---|
| TLK1-J54 | -9.6 | -39.7 (4.1) |
| TLK1-THD | -8.9 | -28.8 (3.7) |
| D2-J54 | -9.3 | -29.0 (3.4) |
| D2-THD | -11.2 | -39.0 (5.4) |
| D2-Risperidone | -19.0 | -53.4 (3.6) |

C.

FIG. 15A
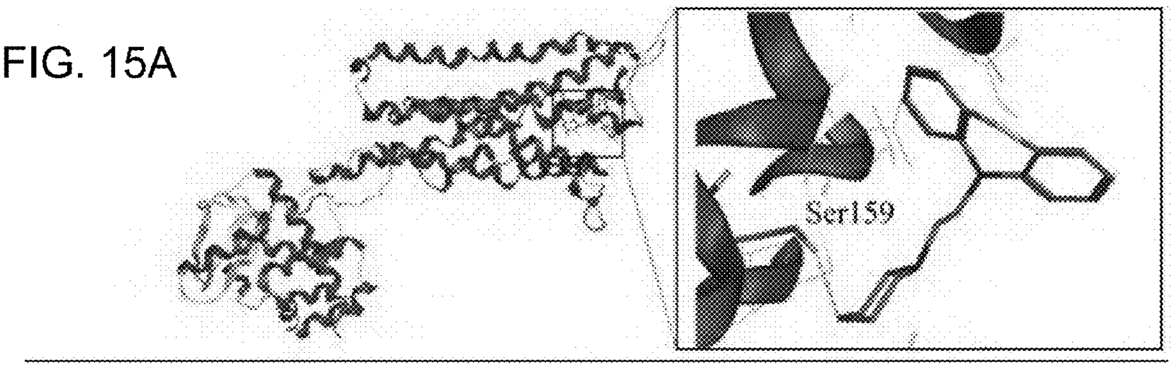
FIG. 15B
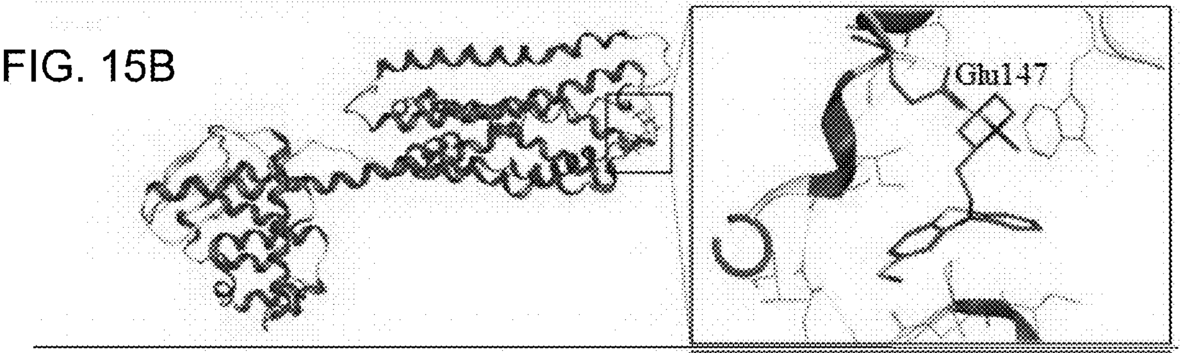
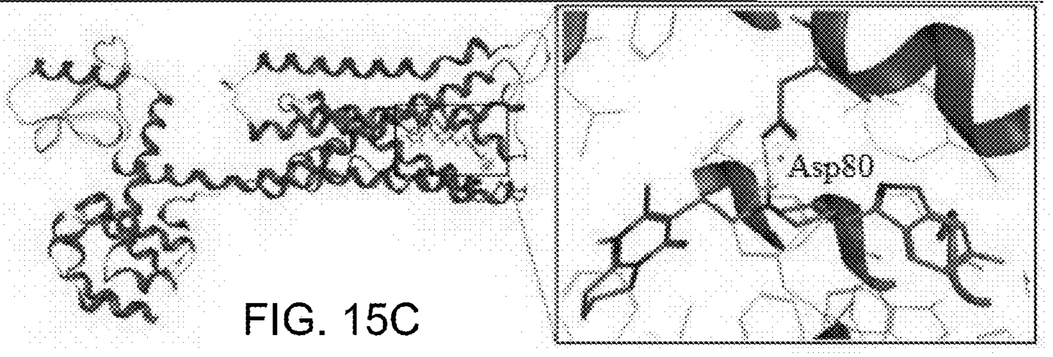
FIG. 15C

13CNMR OF J3-54

Mass Spectra of J3-54

Mass spectra of J3-56

| S.I. | Chemical structure with batch number | S.I. | Chemical structure with batch number |
|---|---|---|---|
| 1 | 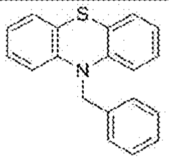 J3-50 | 5 | 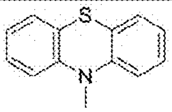 J3- 56 |
| 2 | 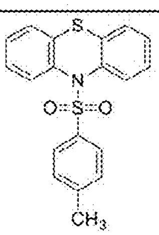 J3-51 | 6 | 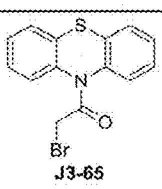 J3-65 |
| 3 | 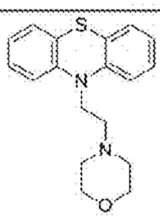 J3-54 | 7 | 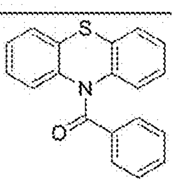 J3-66 |
| 4 | 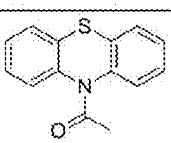 J3-55 | | |
FIG. 22

FIG. 23

| S. No. | Antibody Name | Catalog number | Company |
|---|---|---|---|
| 1 | TLK1 antibody [N2C2] | GTX102891 | Genetex |
| 2 | Rabbit NEK1 Antibody | A304–570A | Bethyl Lab |
| 3 | Purified custom pNek1 antibody | custom | Thermofisher Scientific/Pierce |
| 4 | H2A.X (Ser139) | 05-636 | Millipore |
| 5 | Cleaved Caspase-3 | 9579 | Cell signaling technology |
| 6 | Cleaved Caspase-3 | 9661 | Cell signaling technology |
| 6 | GAPDH | 2118S | Cell signaling technology |
| 7 | Cleaved PARP (Asp214)(D64E10 | 5625 | Cell signaling technology |
| 8 | Anti-PCNA Antibody | MAB424 | Millipore |
| 9 | Phospho-Chk1 (Ser317) | 2344 | Cell signaling technology |
| 10 | Phospho-ATR (Thr1989) | 5801S | Cell signaling technology |
| 11 | Alpha mouse HRP | 7076 | Cell signaling technology |
| 12 | Ki-67 (D3B5) | 12202 | Cell signaling technology |
| 13 | p21 Waf1/Cip1 | 2946 | Cell signaling technology |
| 14 | Alpha rabbit IgG-HRP | 7074S | Cell signaling technology |
| 15 | Anti-beta Tubulin antibody Loading Control (HRP) | Ab218 | Abcam |

FIG. 24

| Cell line | Sub-G1 | G1 | S | G2/M |
|---|---|---|---|---|
| **LNCaP** Control | 0% | 93% | 4% | 3% |
| +BIC | 2% | 94% | 2% | 2% |
| +J54 | 1% | 94% | 3% | 2% |
| +BIC+J54 | 33% | 53% | 4% | 10% |
| **TRAMP-C2** Control | 3% | 42% | 26% | 29% |
| + BIC | 7% | 58% | 21 | 14% |
| +J54 | 11% | 46% | 29% | 14 |
| +BIC+J54 | 26% | 27% | 21% | 26% |

FIG. 25

| Assay system | Inhibition ratio (%) | | | |
|---|---|---|---|---|
| | J54 | THD | Positive substance | |
| | $1\times10^{-7}$ mol/L | $1\times10^{-7}$ mol/L | $1\times10^{-5}$ mol/L | |
| Dopamine D1 (Human) | 12.17 | 67.69 | 100.00 | *R*(+)-SCH-23390 |
| Dopamine D3 (Human) | 19.77 | 95.57 | 99.95 | (±)-7-OH-DPAT |

Receptor: Human recombinant, PKI, Cat No. 6110513

50 mmol/L Tris-HCl (pH 7.4) containing 120 mmol/L NaCl, 5 mmol/L KCl, 2 mmol/L $MgCl_2$ and 1 mmol/L $CaCl_2$ Tracer: SCH23390, [N-methyl-$^3$H]-, PKI, Cat No. NET930

Receptor: Human recombinant, PKI, Cat No. ES-173-M 50 mmol/L Tris-HCl (pH 7.4) containing 5 mmol/L $MgCl_2$ Tracer: 7-Hydroxy DPAT, R-(+)-[$^3$H]-, PKI, Cat No. NET1169

Duplicate samples were analyzed and averaged results are shown.

Data Processing

Inhibition ratios (%) were calculated from "100 – binding ratio".

Binding ratio: $[(B-N)/(B_0-N)]\times100$ (%)

B: Bound radioactivity in the presence of the test article (individual value)

$B_0$: Total bound radioactivity in the absence of the test article (mean value)

N: Non-specific bound radioactivity (mean value)

TARGETING THE TLK1/NEK1 AXIS IN PROSTATE CANCER

CROSS REFERENCE TO RELATED APPLICATIONS/PRIORITY

This application is a continuation of U.S. Ser. No. 16/834,061 filed on Mar. 30, 2020, which claims the benefit of U.S. Provisional Patent Application No. 62/825,800 filed Mar. 29, 2019, all of which are hereby incorporated by reference in their entirety.

STATEMENT REGARDING FEDERALLY SPONSORED RESEARCH OR DEVELOPMENT

This invention was made with government support under Grant No. W81XWH-17-1-0417 awarded by the Medical Research and Development Command. The government has certain rights in the invention.

BACKGROUND

Prostate cancer (PCa) is diagnosed in over 200,000 men each year in the US and accounts for one in four individuals after adjustment for age. Androgen deprivation therapy (ADT) is used to treat advanced PCa with some initial benefits, but Castrate Resistant Prostate Cancer (CRPC) often ensues after 2-3 years. While there are some treatment modalities for CRPC, resistance occurs after a few months and CRPC is currently incurable. Treatments that can significantly improve the benefits of ADT and delay progression have the highest potential of being rapidly implemented and result in a significantly better outcome for advanced PCa, but sufficient treatments have thus far eluded researchers and clinicians.

SUMMARY

Wherefore, it is an object of the present invention to overcome the above-mentioned shortcomings and drawbacks associated with the current technology.

The present invention relates to compositions and methods of treating prostate cancer in a patient comprising administering to the patient a pharmaceutical composition including a first therapeutic including a TLK1B inhibitor, or a pharmaceutically acceptable salt, solvate, ester, amide, clathrate, stereoisomer, enantiomer, prodrug or analog thereof, and a second therapeutic including an antiandrogen or a pharmaceutically acceptable salt, solvate, ester, amide, clathrate, stereoisomer, enantiomer, prodrug or analog thereof. According to a further embodiment the TLK1B inhibitor is a phenothiazine (PTH) antipsychotic. According to a further embodiment the PTH antipsychotic is one of Thioridazine (THD), Perphenazine (PPH), Trifloroperazine (TFP), and Promazine (PMZ), 4-(2-(10H-phenothiazin-10-yl) ethyl) morpholine (J54), and 10-methyl-10H-phenothiazine (J56). According to a further embodiment the PTH antipsychotic is J54. According to a further embodiment antiandrogen is one of bicalutamide, aminoglutethimide, ketoconazole, abiraterone acetate, enzalutamide, and apalutamide. According to a further embodiment the antiandrogen is bicalutamide. According to a further embodiment the TLK1B inhibitor is 4-(2-(10H-phenothiazin-10-yl) ethyl) morpholine (J54) and the antiandrogen is bicalutamide. According to a further embodiment the patient is human. According to a further embodiment the patient is one of chemically and surgically castrated.

The present invention is further related to methods preparing and/or using pharmaceutical composition and pharmaceutical compositions comprising a first therapeutic including a TLK1B inhibitor, or a pharmaceutically acceptable salt, solvate, ester, amide, clathrate, stereoisomer, enantiomer, prodrug or analog thereof, and a second therapeutic including an antiandrogen or a pharmaceutically acceptable salt, solvate, ester, amide, clathrate, stereoisomer, enantiomer, prodrug or analog thereof. according to a further embodiment the TLK1B inhibitor is a phenothiazine (PTH) antipsychotic. According to a further embodiment the PTH antipsychotic is one of Thioridazine (THD), Perphenazine (PPH), Trifloroperazine (TFP), and Promazine (PMZ), 4-(2-(10H-phenothiazin-10-yl) ethyl) morpholine (J54), and 10-methyl-10H-phenothiazine (J56). According to a further embodiment the PTH antipsychotic is J54. According to a further embodiment antiandrogen is one of bicalutamide, aminoglutethimide, ketoconazole, abiraterone acetate, enzalutamide, and apalutamide. According to a further embodiment the antiandrogen is bicalutamide. According to a further embodiment the TLK1B inhibitor is 4-(2-(10H-phenothiazin-10-yl) ethyl) morpholine (J54) and the antiandrogen is bicalutamide. According to a further embodiment, the pharmaceutical composition further comprises an excipient. According to a further embodiment the pharmaceutical composition is in the form of a tablet, a capsule, a liquid solution or suspension, a powder, a liquid, or solid crystals.

The present invention further comprises a purified sample of a 4-(2-(10H-phenothiazin-10-yl) ethyl) morpholine. According to a further embodiment the sample is a solid crystal.

The present invention further relates to targeting a specific liability that incurs in Androgen Responsive PCa cells when shifted to ADT, by adding an inhibitor, such as J54, of the TLK1>Nek1>ATR>Chk1 DDR axis in order to abrogate the checkpoint and promote apoptosis. J54 is a novel, structure-based inhibitor of TLK that holds much promise to prevent progression toward CRPC and death from PCa.

The present invention relates to pharmaceutical compositions of a therapeutic (e.g., a TLK1B inhibitor, an antiandrogen, and a combination of each), or pharmaceutically acceptable salts, solvates, esters, amides, clathrates, stereoisomers, enantiomers, prodrugs or analogs thereof, and use of these compositions for the treatment of a PCa.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 μM-10 μM (e.g., between 0.05 μM-5 μM).

In some embodiments, the peak plasma concentration of the therapeutic is maintained for up to 14 hours. In other embodiments, the peak plasma concentration of the therapeutic is maintained for up to 1 hour.

In some embodiments, the condition is a PCa.

In certain embodiments, the PCa is mild to moderate PCa.

In further embodiments, the PCa is moderate to severe PCa.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the PCa.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 μM-10 μM (e.g., between 0.05 μM-5 μM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 μM, 0.1-10 μM, 0.1-5.0 μM, or 0.1-1 μM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95% or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., a TLK1B inhibitor and antiandrogen combination, such as J54 and bicalutamide, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., PCa). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 1A-1E show that bicalutamide in combination with THD suppresses growth of LNCaP xenografts via pNek1-pATR-pChk1 DDR Pathway. FIG. 1A shows tumor volume for LNCaP Xenograft model treated with THD/Bicalutamide or combination by I.P. injections. FIG. 1B shows tumor weight for LNCaP Xenograft model treated with THD/

Bicalutamide or combination. FIG. 1C shows Western blot on tissue lysate from xenograft tumors for Phospho-protein of DDR pathways. FIG. 1D shows representative LNCaP xenograft tumors pic. Below is graph for tumor weight of respective groups. FIG. 1E shows representative images of Immunohistochemistry for p-NEK1 on control/THD/Bicalutamide or combination (Scale40×). The adjacent graph is quantitation.

In FIG. 1F, the model shows important regulatory features lying in the N and C-lobes. FIG. 1G shows the hinge region connecting N and G-lobes. FIG. 1H shows a detailed view of DFG loop, Activation loop, P+1 loop and the αF-helix. FIG. 1I shows the ATP binding site of the kinase domain.

FIG. 2A depicts the homology model of TLK1 with active sites; ATP binding site, Allosteric sites 1 and 2. FIG. 2B depicts dock pose for compound J3-54 in the ATP-binding site. FIG. 2C depicts Dock pose for compound J3-54 in the allosteric binding site 1. FIG. 2D depicts Dock pose for compound J3-54 in the binding site 2.

FIG. 3A is active in kinase assays, FIG. 3B and was used in high-throughput inhibitor screening with a specific Nek1 peptide, with J54 shown in FIG. 3C. FIGS. 3D-3E show Inhibitory curves of J54 and J56 compared to THD carried out at 0.2 mM ATP or at different competitive concentrations. FIGS. 3F-3K show cytotoxicity and colony formation potential of different PCa cells, and FIGS. 3L and 3M show cell-cycle analysis of LNCaP and TRAMP-C2 cells.

FIG. 5A is a graph showing selected phenothiazines that were tested with recombinant TLK1B in autokinase assays employing γ32P-ATP and determined by TCA-precipitate counts (% activity compared to no drug. ED50 $P<0.01$). FIG. 5B shows an example of PTH inhibitor (PPH) that was tested in cultured cells by IP/autokinase/autoradiography. 293T cells were incubated for 1 hour with PPH. TLK1 was immunoprecipitated, followed by autophosphorylation with y-ATP32. The blots were then probed with TLK1 antiserum.

FIG. 7A shows expression of TLK1B in LNCaP cells transferred to CSS-medium. Cells were grown in medium containing FCS or transferred to CSS, for either 16 h (top), or during a 4 h time-course (bottom). Where indicated, 20 nM rapamycin was also added. FIG. 7B shows expression of TLK1B in NeoTag cells cultured with and without androgen.

FIG. 8D shows ATP dependence. FIG. 8E shows various compounds that were tested for in vitro inhibitory effects, with J54 shown. FIGS. 8F and 8G show inhibitory curves of J54 and J56 compared to THD that were carried out at 0.1 mM ATP or at different competitive concentrations. All experiments were conducted in triplicates. The DiscoverRx ADP Hunter™ (Eurofins DiscoverRx, Fremont, CA, US) Kit was used to measure the generation of ADP resulting from kinase phosphorylation of substrate.

FIGS. 9A-9D show model building and molecular dynamics studies, with FIG. 9A showing a model of TLK1B kinase domain; FIG. 9B showing protein RMSD for TLK1B over 1 μs simulation; FIG. 9C showing Ligand RMSD of J54 (Black) and THD (Red) in post docking simulation for 100 ns; and FIG. 9D showing docking score and computed MM/GBSA binding free energy.

FIG. 10B showing interactions of THD with the active site of TLK1.

FIG. 11A shows clonogenic assays of AS PCa cells (VCaP, LNCaP, and TRAMP-C2) after treatment with BIC, J54, or combination. The cells were grown for 2-3 weeks and stained with crystal violet. All experiments were conducted in triplicates. FIG. 11B shows cell proliferation assays of the indicated cell lines incubated with different concentrations of J54. The cell lines used were human "normal" RWPE-1, LNCaP, (LNCaP-derivative) C4-2B, 22RV1, DU14, PC3, and mouse TRAMP-C2. FIGS. 11C and 11D show cell proliferation of LNCaP and TRAMP-C2 were determined during a 3 days incubation with different concentration of J54 (MTS assay). All experiments were conducted in triplicates. FIG. 11E shows cell cycle analysis by PI-FACS of LNCaP and TRAMP-C2 cells incubated for 24 h with BIC, J54, or combination (5 μM each). Representative analysis of two independent experiments is shown.

FIG. 13A shows the time course of tumor growth of LNCaP cells xenografts in 4 treatment groups. Treatment started 19 days after implantation when the tumors measure –200 mm3. Two independent experiments with 5 mice per group were carried out. J54 and Bicalutamide was dissolved in DMSO and diluted in corn oil 1:10 and administered IP bi-weekly. Sectioning and processing of the tissues were carried out in the FWCC Histology Service, using automated processes and equipment to provide uniform and standardized results. Indirect labeling was with ABC Elite: RTU Vectastain Elite Reagent, Vector #PK-7100; DAB: ImmPact DAB, Vector #SK-4105. Light counterstaining was done with hematoxylin. FIG. 13B shows tumor weights that were determined for all groups at end of the treatment course. FIG. 13C shows examples of tumor size at the end of the experiment. FIG. 13D shows representative sections from tumors resected from mice in the 4 treatment groups analyzed by IHC for pNek1. Note the weak pNek1 stain in the tumor from mice treated with J54, in contrast to the increase seen with BIC.

FIGS. 15A-15C show docked pose of ligands to active site of D2 dopamine receptor after 100 ns of MD simulation: (a) J54, (b) THD and (c) risperidone.

In FIG. 19A, for the pharyngeal pumping assay, wild-type animals (N2 strain) were transferred to plates with diluted DMSO (Control) or drug (J-54 or trifluoperazine) at 160 μM final concentration for 90 min before quantifying pharyngeal pumping see SI methods). The inventors counted visible movement of the grinder (pharyngeal contractions) for 30 sec to obtain the pumping rate (N=45). Note that in pharyngeal pumping, J54 reduced the pumping rate but to a lesser extent than a much lower concentration of TFP. Inhibition of pharyngeal pumping by trifluoperazine (TFP), a typical PTH antipsychotic, is attributed to its known activity as a dopamine and calmodulin antagonist. In FIG. 19B. foraging, regulated by serotonin and dopamine, was studied in wild-type animals evaluated in the presence of DMSO (Control) or J54 at a high dose of 160 μM vs. TFP at 40 μM. The number of omega turns (head touches body) and reversals were then counted over the next 3 min to quantify search behavior for each group (N=13 per group). FIG. 19C shows reduction of dopamine-induced immobility. Dopamine produces immobility in *C. elegans* after 2-3 hours of exposure. Antipsychotic drugs, such as haloperidol, that potently block D2 dopamine receptors largely counteract the effects of dopamine, i.e., more animals continue to move on plates that include dopamine plus drug. Wild-type animals were incubated on 60 agar plates with bacteria and diluted DMSO (Control) or J54 or haloperidol at 160 μM final concentrations. After 1 hour on these plates, they were transferred to 60 mm agar plates with bacteria that also contained dopamine (final concentration 25 mM) plus diluted DMSO (Control) or else J-54 or haloperidol at final concentrations of 160 μM. After 3 hours on the dopamine plates, the inventors examined movement and counted animals as moving if they traversed half their body length in either the forward or backward direction during a 5-sec observation period. The inventors then calculated the percentage of animals moving and repeated this experiment three times to confirm the effects of drug. J54 was not toxic to worms even after prolonged exposure.

FIG. 22 is a table listing the chemical structure of J3-50, J3-51, J3-55, J3-65 and J3-66 compounds.

FIG. 23 is a table listing the antibodies used for Western blots and IHC.

FIG. 24 is a table showing cell cycle analysis.

FIG. 25 is a table showing the inhibitory effect of test substances on radioligand binding to two recombinant human dopamine receptors (DR2).

DETAILED DESCRIPTION

Figure 1A:
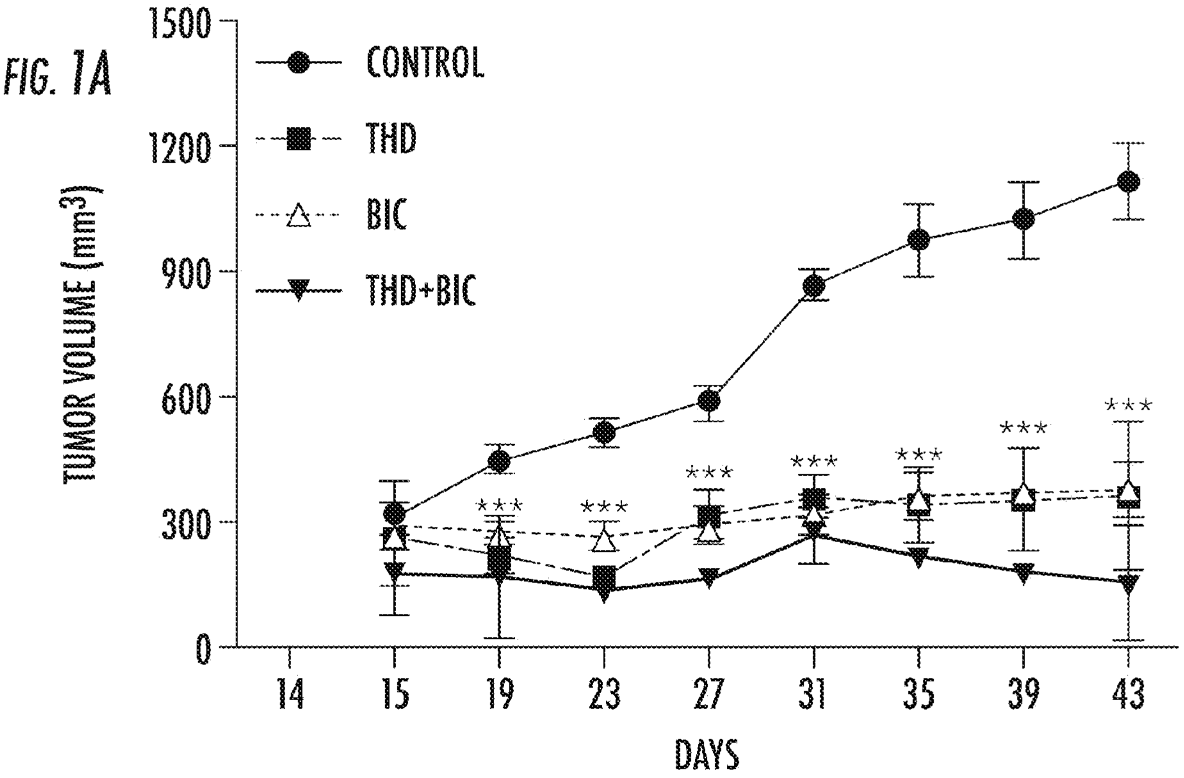
Figure 1B:
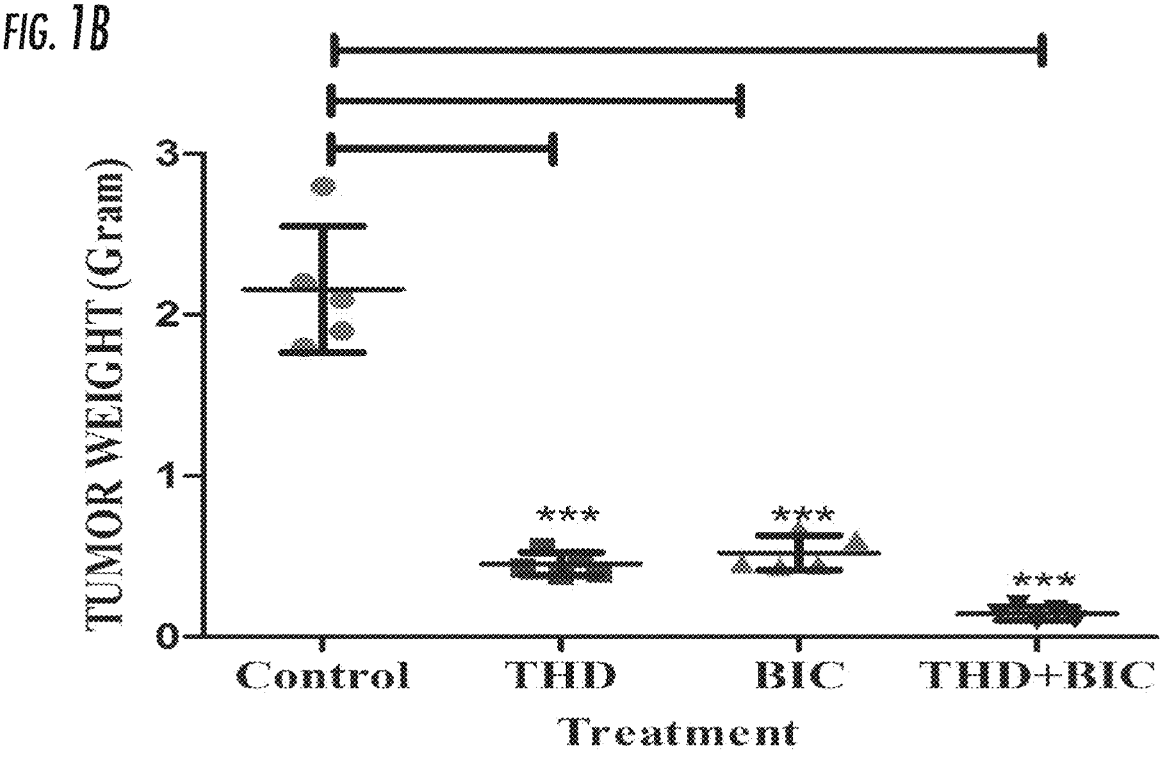
Figure 1C:
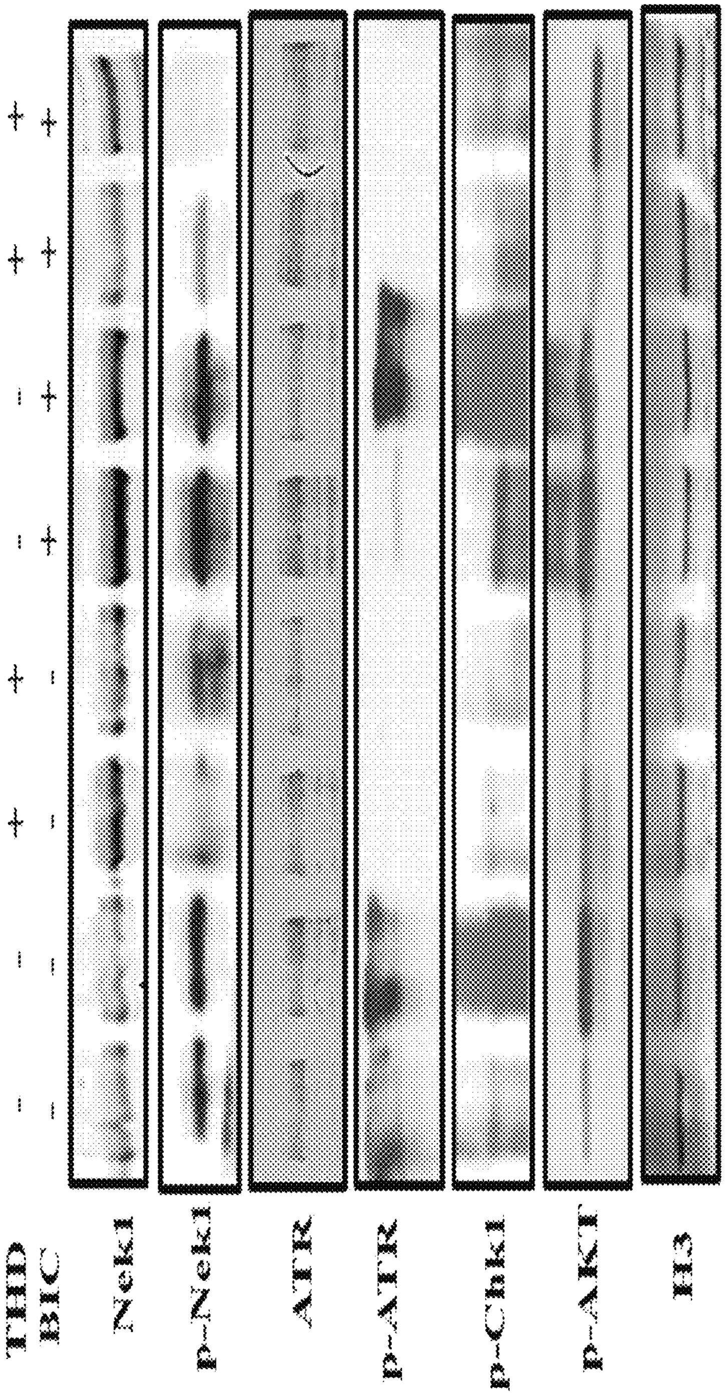
Figure 1D:
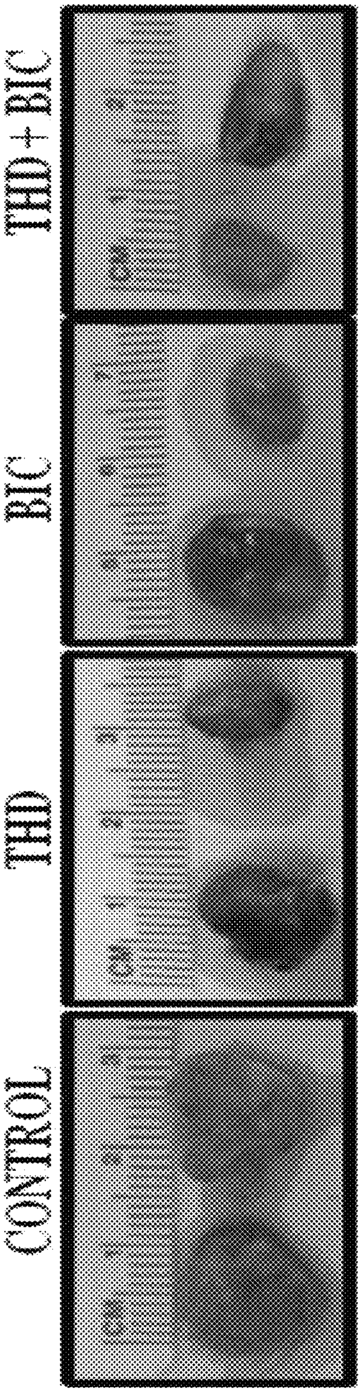

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1A-21, a brief description concerning the various components of the present invention will now be briefly discussed. A first aspect of the present invention is the discovery that targeting the TLK1/NEK1 axis with specific TLK1 inhibitors will be an effective therapy for PCa in combination with standard care, ADT. A second aspect of the present invention is the discovery of key compounds.

The standard therapy for advanced Prostate Cancer (PCa) consists of anti-androgens which provide respite from the disease progression, yet ultimately fail and result in the incurable phase of the disease: mCRPC. Targeting PCa cells before their progression to mCRPC would significantly improve the outcome. Untoward toxicity limits the combination therapies targeting the DNA Damage Response (DDR), and hence the goal of clinical trials is to target the DDR more specifically. Androgen deprivation therapy (ADT) in LNCaP cells results in the increased expression of TLK1B, a critical kinase upstream of NEK1 and ATR, thereby mediating a DDR that typically causes a temporary cell cycle arrest of androgen-responsive PCa cells. Following the DNA damage, the addition of a TLK1 specific inhibitor, thioridazine (THD), impairs ATR and Chk1 activation, establishing the existence of an ADT>TLK1>NEK1>ATR>Chk1 DDR pathway, while its abrogation, leads to apoptosis. However, THD is a known anti-psychotic and has undesirable side-effects. Hence, there is a compelling need to design and develop next-generation TLK1 inhibitors to circumvent the adverse effects and advance them in the clinic.

Our experimental data revealed that the pATR, pChk1, pNEK1, Ki-67 and PCNA were remarkably inhibited when treated with THD in combination with an anti-androgen drug, Bicalutamide (BIC). Moreover, it also induced apoptosis and increased DNA damage as demonstrated by the cleaved PARP, Caspase 3 and γH2AX levels respectively. The new inhibitor screening assay showed J54 compound to be most potent and inhibitory with a log $IC_{50}$ of 1.1 μM. J54 binds to the protein's allosteric site noncompetitively with ATP and interacts with His504 and Gly630 with a corresponding docking score of −6.736. J54 is found to be non-toxic to normal cells and also suppresses the growth of androgen-dependent colonies of LNCaP cells cultured with BIC.

The inventors' work evidences that targeting the TLK1/NEK1 axis with specific TLK1 inhibitors will be an effective therapy for PCa in combination with standard care, ADT.

The inventors performed immunoblotting of the tumor tissue phosphoproteins (pATR, pChk1 and pNEK1) and immunohistochemistry analysis of the tissue sections from the LNCaP xenograft models. To identify and develop new potent inhibitors against TLK1, the inventors employed an in-silico homology modelling and molecular docking approach. Based on the protein-ligand binding interactions and the docking score, a handful of compounds were shortlisted, synthesized and screened for the TLK1 inhibition potential in-vitro and using cell-based assays.

The Tousled Like kinase 1 (TLK1) is involved in the DNA damage response and repair, and mitotic segregation of chromosomes. The inventors identified TLK1B, a splice variant of TLK1, as an important effector of chemo-resistance that is often overexpressed in PCa cell lines and biopsies, and its expression was identified as a key driver of PCa. The inventors have identified several specific inhibitors of TLK1B and have demonstrated that they sensitize PCa cells to killing by doxorubicin in tissue culture or as mouse xenografts. However, the mechanism of action of TLK1B remained to be largely elucidated, since most of its substrates have not been identified. The inventors have now identified the proteome target of TLK1B, and have identified an important new interaction with NEK1, a member of the NIMA related kinases, which is involved in the DNA Damage Response (DDR) and Chk1 activation. Hence, the inventors hypothesize that TLK1/NEK1 axis is a critical target for therapy, and particularly to enhance response to ADT. The inventors hypothesized that inhibition of the TLK1/NEK1 axis will suppress the DDR and cell cycle arrest elicited by ADT, and result in excess replication-induced DNA damage, leading to death of PCa cells. The inventors have acquired evidence for this by demonstrating that inhibition of TLK1B with thioridazine (a phenothiazine antipsychotic in a class of specific TLK inhibitors) resulted in: (1) complete inhibition of the conversion of LNCaP cells to androgen independent growth after three weeks of culture with bicalutamide (antiandrogen) and (2) inhibition of NEK1 activation that occurs in LNCaP cells cultured in charcoal-stripped serum (CSS) concomitant with increased expression of TLK1B. The inventors also found that expression of the NEK1-T141A mutant that cannot be phosphorylated by TLK1B resulted in loss of Chk1 phosphorylation/activation following DNA damage ($H_2O_2$) and impaired checkpoint establishment, as the inventors had expected.

The inventors identified inhibitors of TLK1 and found several in the class of phenothiazine (PTH) antipsychotics which the inventors propose to repurpose for the treatment of PCa to improve response to ADT. Further delineation of the TLK1/NKE1 axis and its involvement in survival of PCa cells following ADT can lead to the discovery of even more specific PTH inhibitors, which the inventors intend to pursue. The translational potential of this work is immediate since it would not be difficult to reposition an FDA-approved PTH in combination with ADT. This research combines novel basic findings with innovative use of a class of known drugs.

Figure 5A:
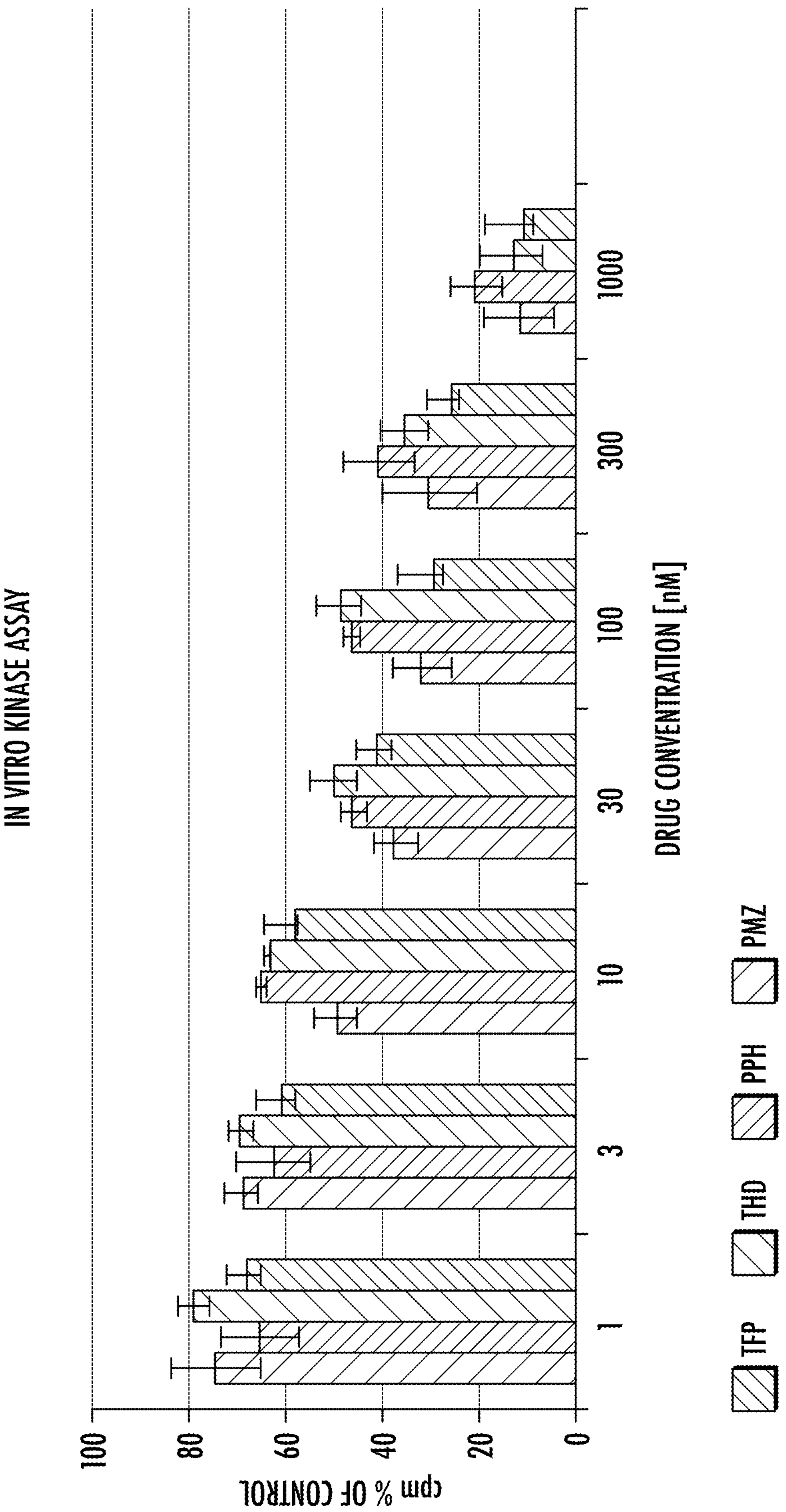
FIGS. 5A and 5B show Inhibition of TLK1/1B autophosphorylation by PTH.
Figure 5B:
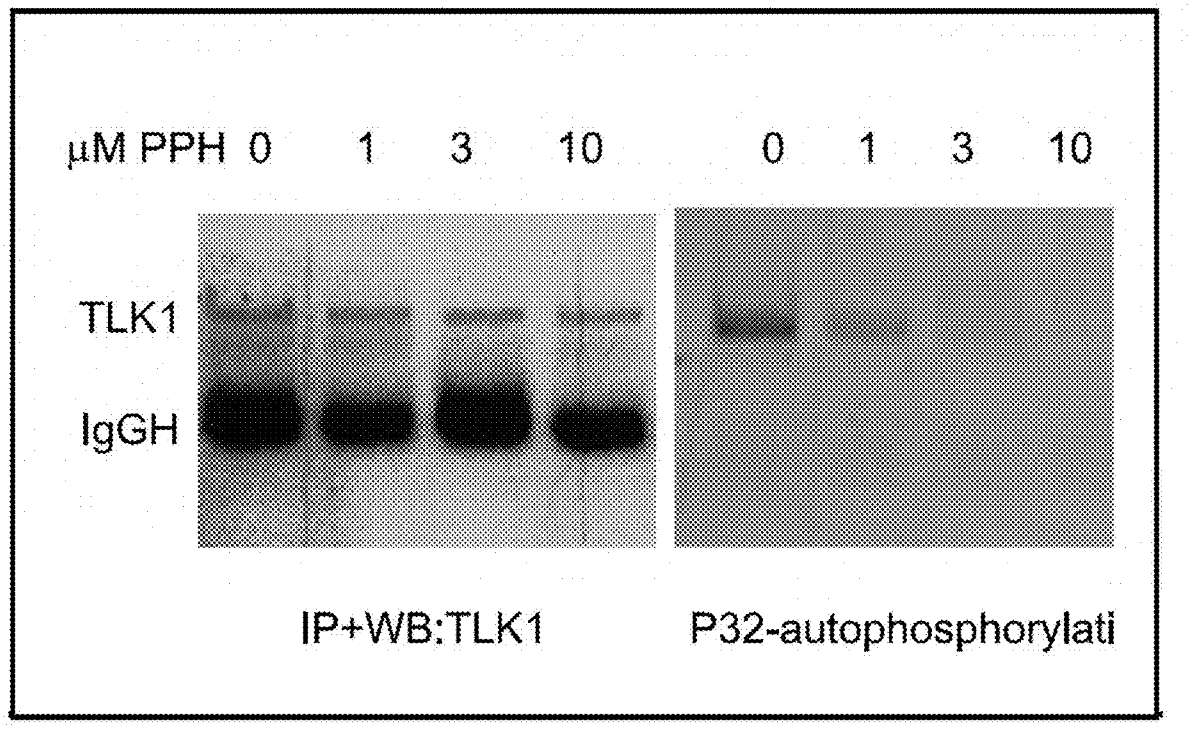

Identification of TLK inhibitors. The inventors have screened the Prestwick Library, partially the ChemDiv, and two proprietary libraries (10,000 compounds) for inhibitors of TLK with a high throughput screen with recombinant TLK1B and a Rad9 peptide substrate. The inventors identified four strong inhibitors in the class of PTH antipsychotics: Thioridazine (THD), Perphenazine (PPH), Trifloroperazine (TFP), and Promazine (PMZ), that block the dopamine D2 receptor in the brain. The inhibition of autokinase activity was confirmed by TCA-precipitable counts with γ32P-ATP (FIG. 5A). The drugs worked specifically at low μM concentration after immunoprecipitation (IP) of TLK1 from cells, and they remained associated with the protein, retaining their inhibition even after removal (after IP the inventors did not add the drugs in the kinase reaction—FIG. 5B).

The inhibitors markedly increased sensitivity to doxorubicin that could be explained by inhibition of NHEJ, as shown by slower regression of DSB repair foci (γH2AX) and delayed repair kinetics of a single DSB generated with HO endonuclease on a reporter system. The specificity of THD was tested on a kinome panel (456 human kinases—KinomeScan-DiscoverX), and no other kinase (except TLK2) in the panel was inhibited, although THD may impact other cellular functions. The inventors also showed that the TLK inhibitors sensitize PCa cells to killing with doxorubicin in vitro and in xenografts. The inventors tested three PTH (THD, PPH, TFP) at 15 μM on a panel of cell lines, including RWPE1 and normal immortalized hTERT-HME1 cells, and the PTH had low toxicity in the absence of doxorubicin.

Figure 6:
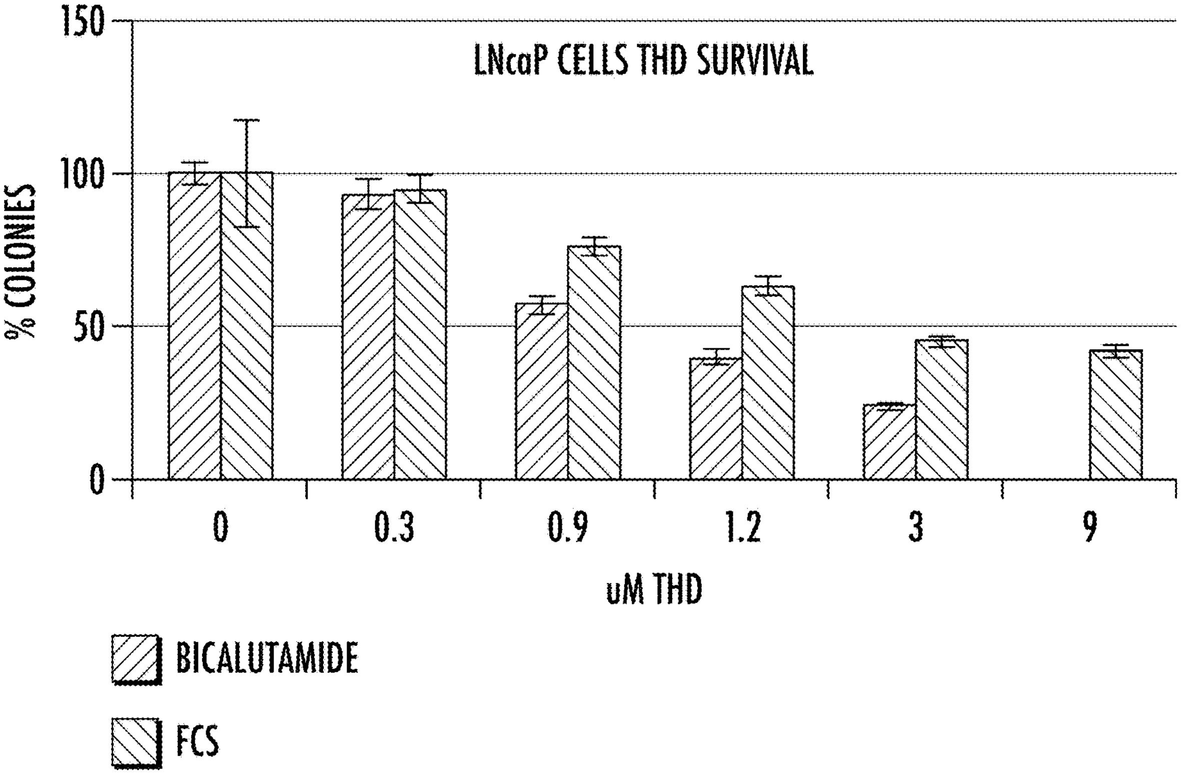
FIG. 6 is a graph showing that A1 colonies do not develop with THD (concentration dependent). LNCap cells were plated in 6-well plates at 4000 cells with bicalutamide (10 nM) to score developing A1 colonies, or 400 cells in control medium to monitor for general clonogenic inhibition by THD.

Inhibition of colony formation of LNCaP cells with combined ADT and Thioridazine (THD). One of the inventors' key hypotheses is that treatment of androgen responsive PCa cells with antiandrogens would result in upregulation of the TLK1/NEK1 axis via activation of mTOR pathway, and that this axis is critical for survival of the cancer cells. The inventors have tested this by monitoring the inhibition of emergence of Androgen Insensitive (AI) colonies following treatment of LNCaP cells with bicalutamide (antiandrogen) and increasing concentrations of THD (TLK inhibitor). A1 colonies were scored after three weeks. At a concentration of 3-9 μM THD, which inhibits growth only 50% in androgen containing medium (FCS), few or no A1 colonies emerged (FIG. 6).

Figure 7A:
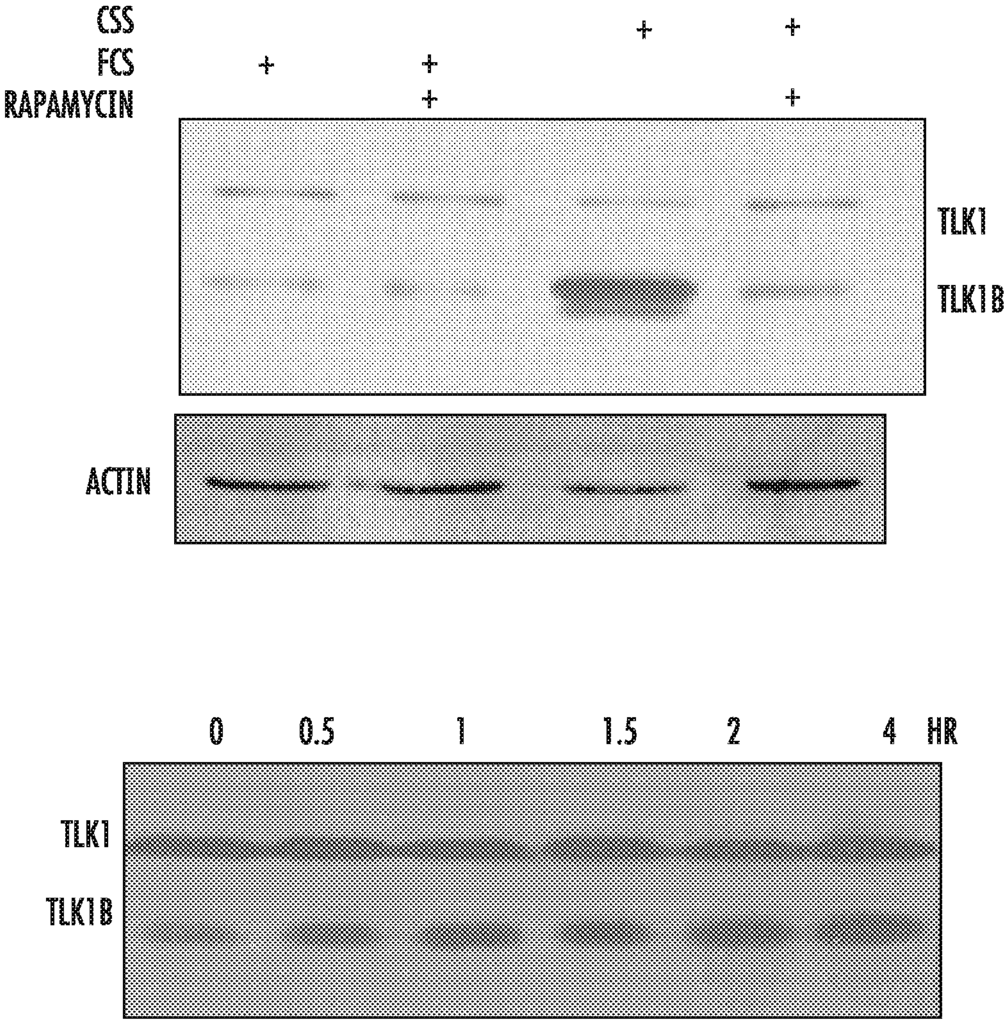
FIGS. 7A and 7B are Western blots.

Expression of the TLK1B splice variant is translationally induced by ADT in LNCaP cells. Prostate cancer is characterized by its dependence on the androgen receptor (AR) and frequent activation of PI3K signaling. PI3K pathway inhibition activates AR signaling and AR inhibition activates mTOR and AKT signaling. Thus, these two oncogenic pathways regulate each other by reciprocal feedback. Inhibition of one activates the other, thereby maintaining tumor cell survival. In FIG. 6 the inventors show that passing LNCaP cells to charcoal-stripped serum (CSS) results in a rapid increase in the expression of the TLK1B splice variant. This is suppressible by rapamycin, strongly suggesting that it is due to the activation of the AKT/mTOR/eIF4E pathway (FIG. 7A).

Figure 7B:
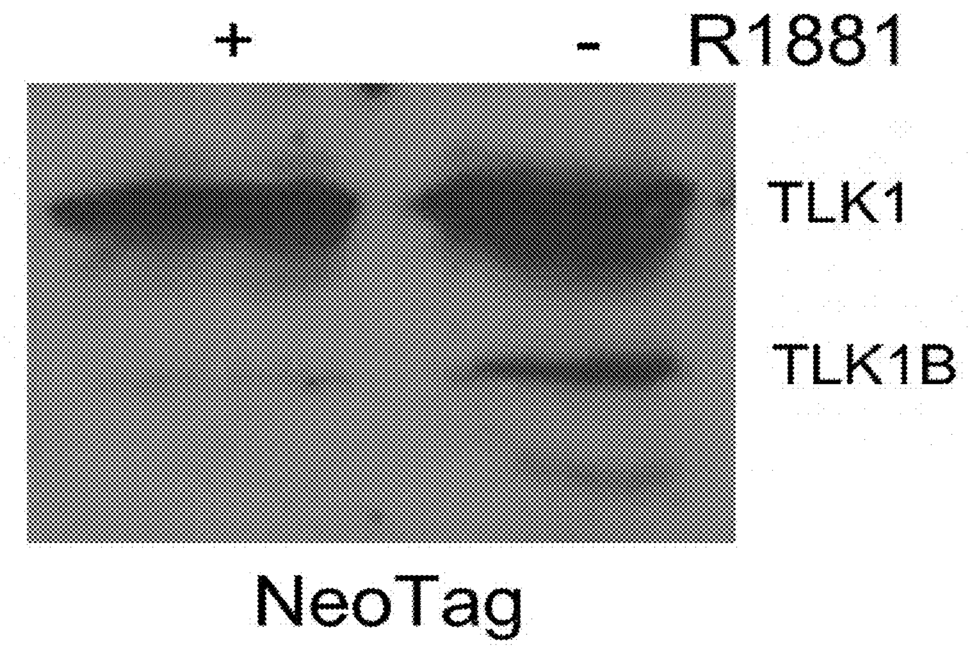

The response to ADT is rapid, suggesting that it is most likely at the level of TLK1B mRNA translation, which likely results in parallel in activation of NEK1. The inventors propose that activation of the TLK1/NEK1 axis following ADT is a very important, early pro-survival pathway to cope with the DNA damage that ensues. The mechanism is probably more general since another androgen sensitive cell line (NeoTag) also upregulated the expression of TLK1B in the absence of androgen (FIG. 7B). Targeting the TLK1/NEK1 axis could result in suppression of CRPC emergence.

A medicinal product of one embodiment of the present invention is in composition of matter whereby treatment with ADT (standard of care for advanced prostate cancer) is combined with an inhibitor of the TLK1/NEK1 axis, which is critical for survival of cancer cells before progression to CRPC. The combination therapy may include repurposing of phenothiazine antipsychotic inhibitors of TLK1 for the treatment of androgen-responsive PCa.

A competitive advantage of some embodiments of the present invention include that DNA damage response (DDR) includes the activation of numerous cellular activities that prevent duplication of DNA lesions and maintain genomic integrity, which is critical for the survival of normal and cancer cells. Specific genes involved in the DDR such as BRCA½ and P53 are mutated during prostate cancer progression increasing the genomic instability of cancer cells. These events may render prostate cancer cells particularly sensitive to inhibition of specific DDR pathways, such as PARP in homologous recombination DNA repair and Chk1 (target of Nek1) in cell cycle checkpoint and DNA repair, creating opportunities for synthetic lethality or synergistic cytotoxicity. Recent reports highlight the critical role of androgen receptor (AR) as a regulator of DDR genes, providing a rationale for combining DNA damaging agents or targeted DDR inhibitors with AR inhibition as treatment for aggressive disease. Despite this promise, PARP inhibitors have not been effective for PCa and showed some effect only in tumors with HR deficiency (BRCA½). Targeting the DNA DSB repair machinery (ATM and DNA-PK) has been successful in sensitizing PCa cells to IR and doxorubicin, as the inventors have found by targeting TLK1. This is theoretical support for a drug combination (e.g., bicalutamide or abiraterone in combination with a TLK1B inhibitor) be successful and result in significant competitive advantage over similar DDR-based strategies that have not worked very well.

A further development of the present invention, including the compounds J54 and J56, follow.

Figure 1F:
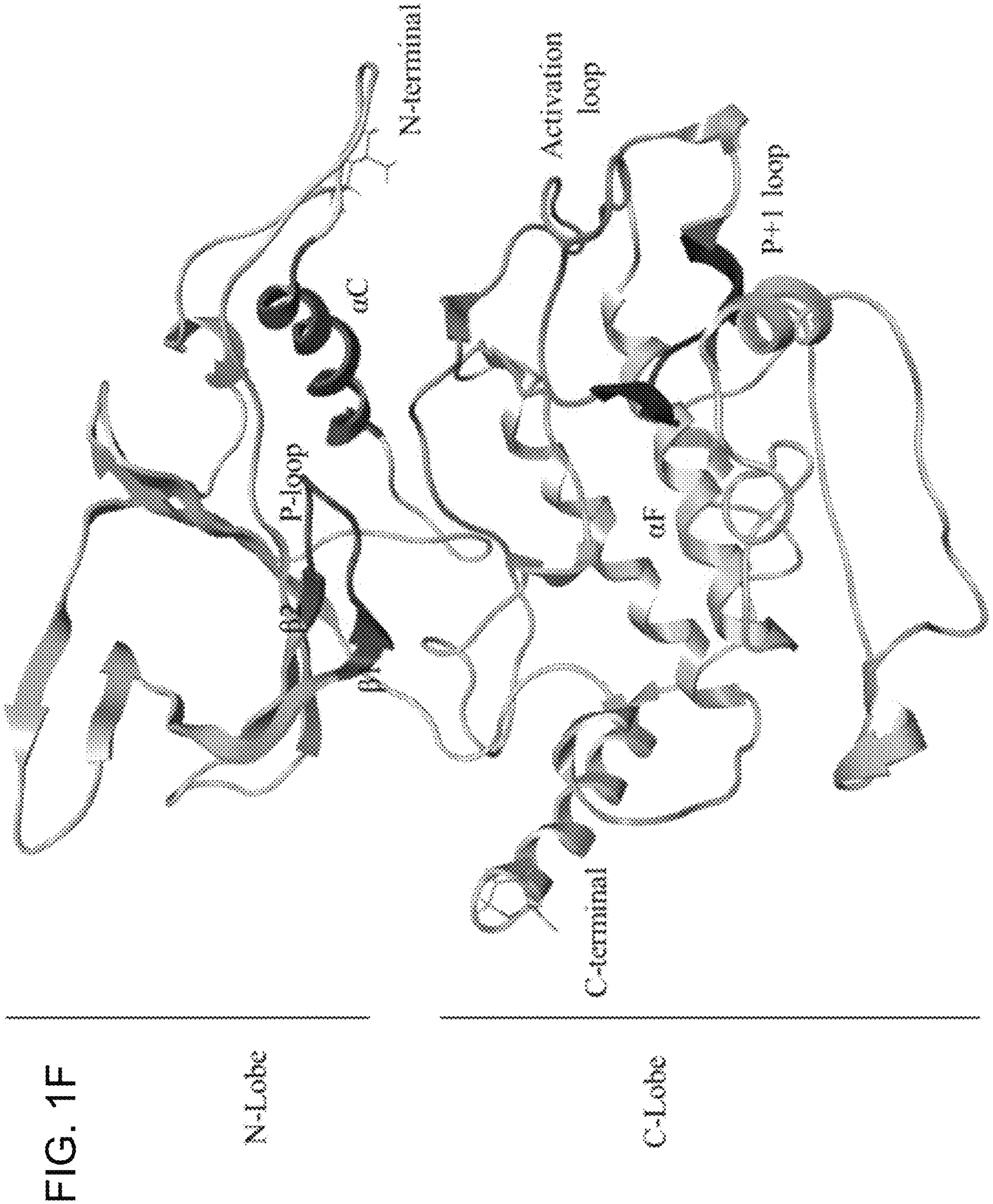
FIG. 1F-1I show detailed views of homology model or Human TLK1 kinase domain.
Figure 1G:
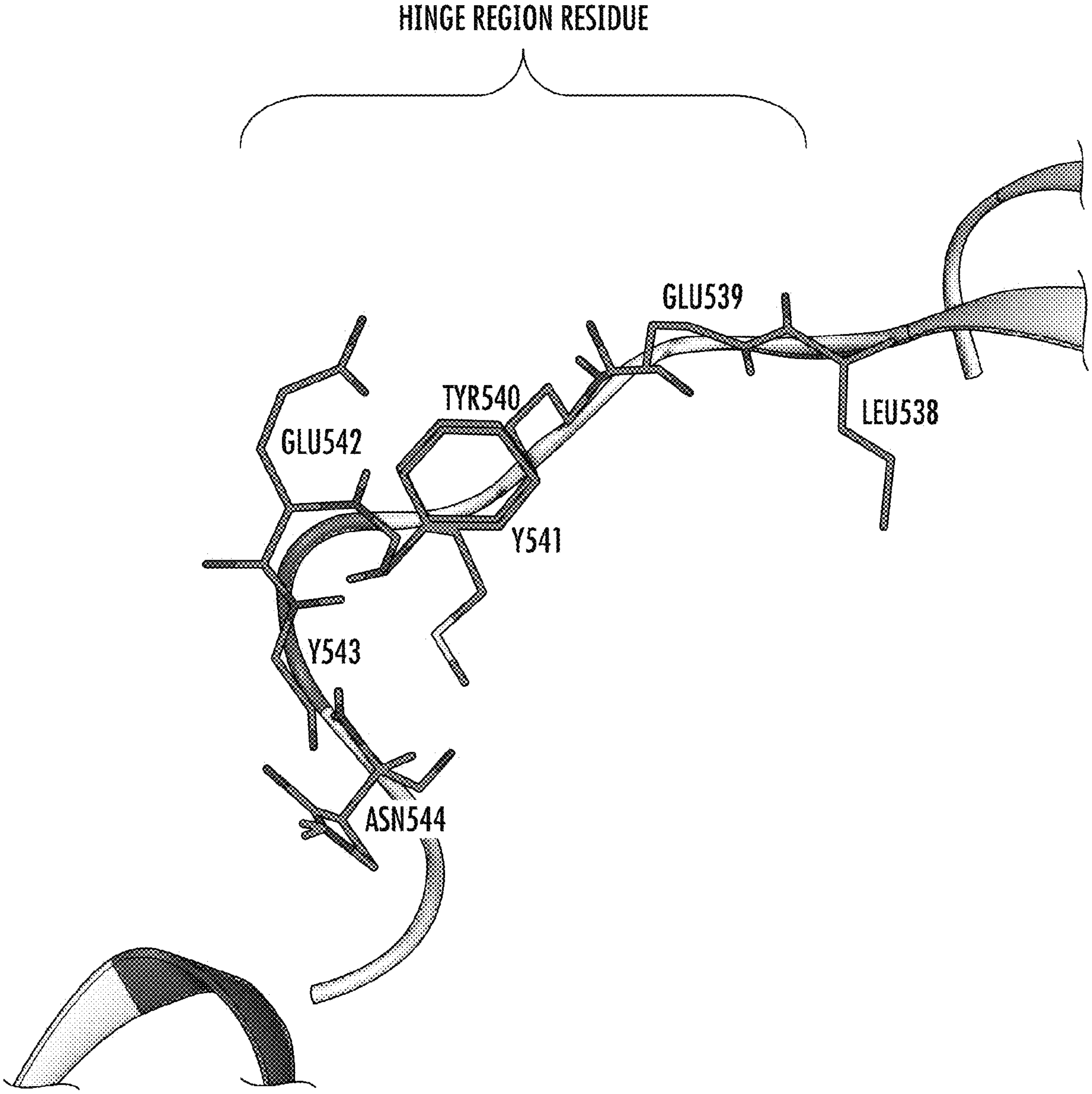
Figure 1H:
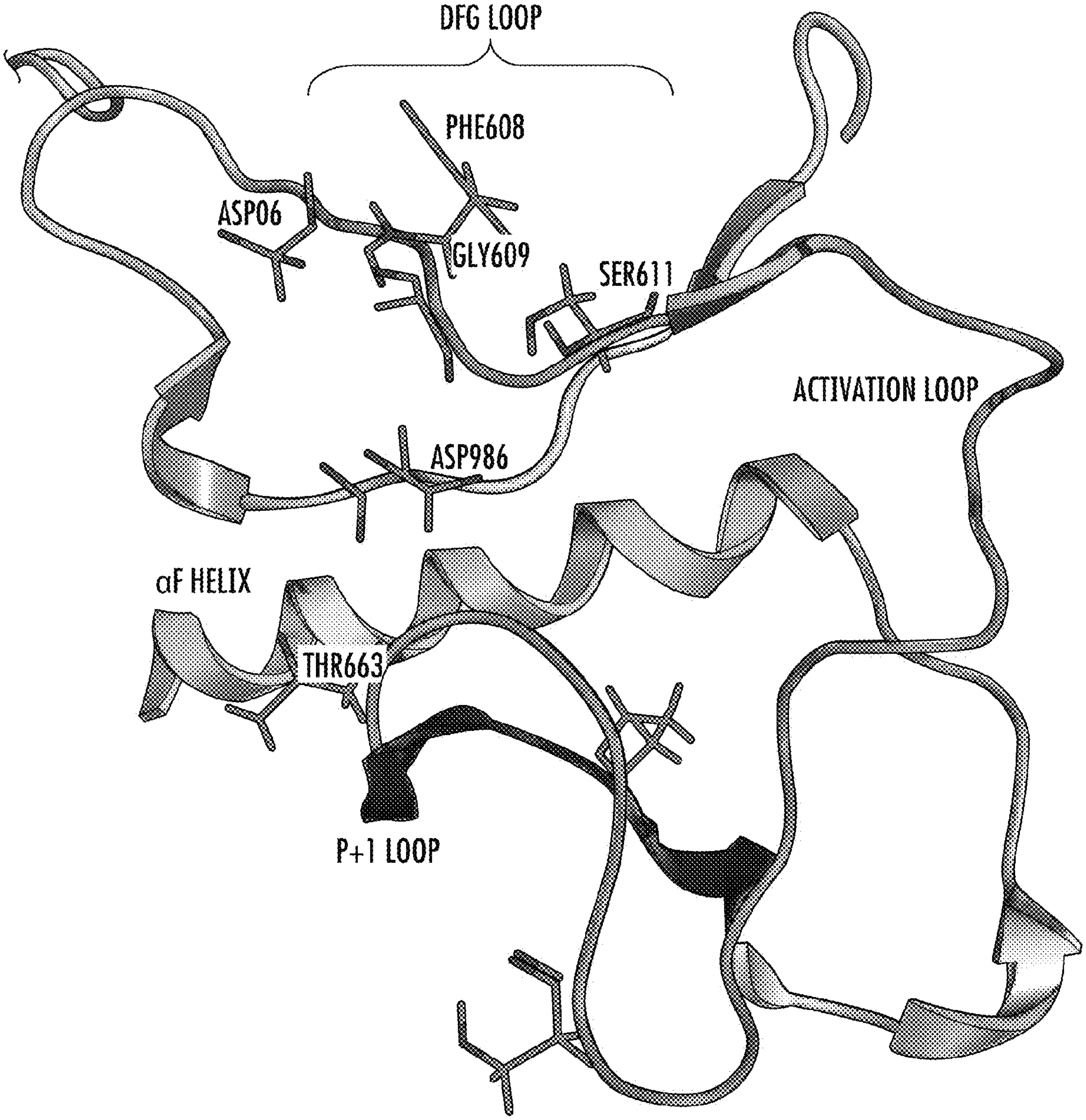
Figure 1I:
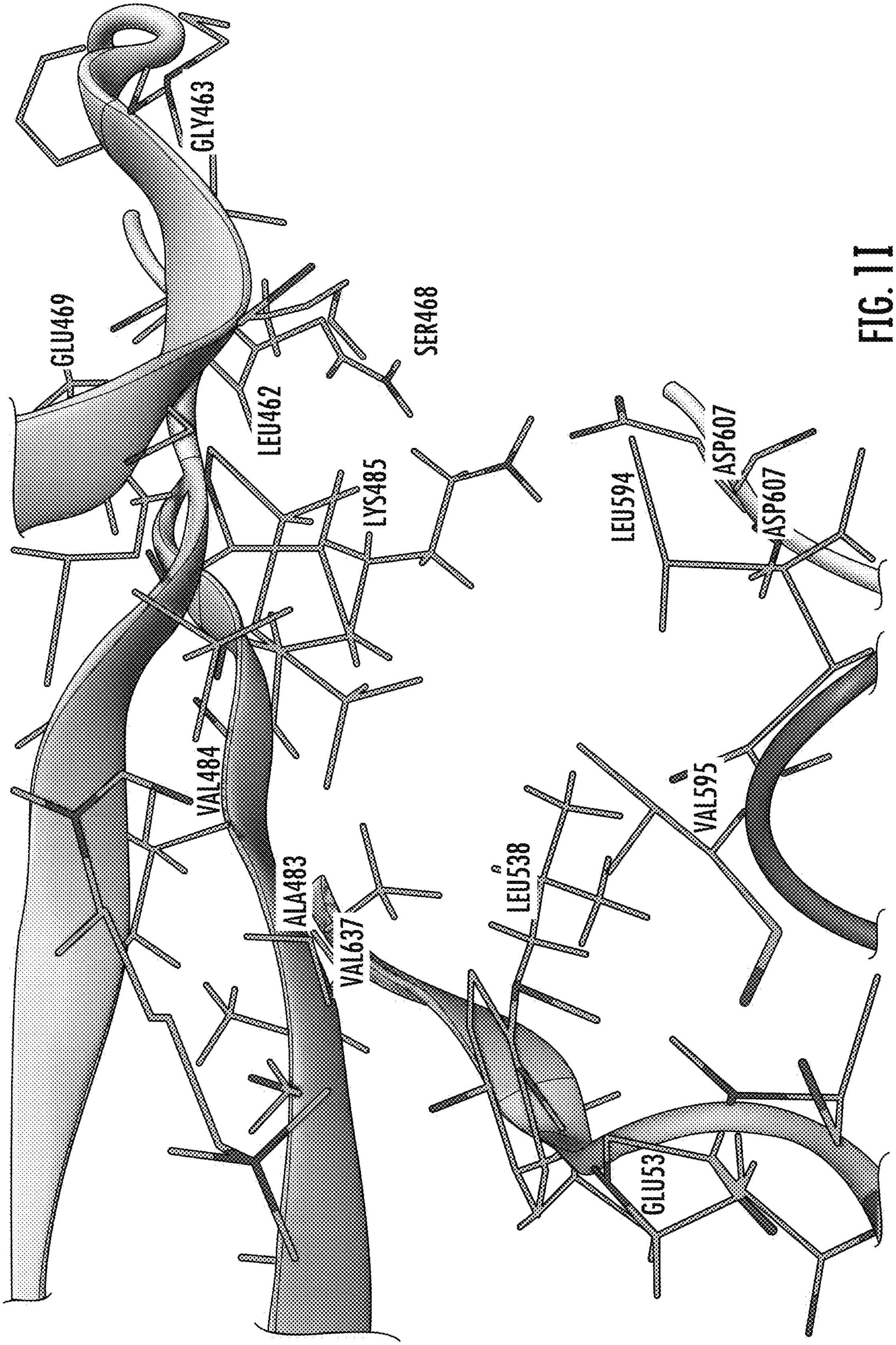

TLK1 Homology Model: Due to unavailability of crystal structure for TLK1, the inventors performed de novo homology modelling and prepared model structure for kinase domain of human TLK1 protein (FIG. 1F). The model shows structural features hallmark to the kinase domain, the R-spine is in correct position and forms a connecting bridge between N and C-lobes. The R-spine is followed by the DFG loop (Asp607, Phe608 and Gly609) in the C-lobe. The hinge region is formed by residues Leu538-Asn544, which allows the slight open and close motion between the two domains. The plausible ATP-binding site lies in the N-lobe and is formed by the residues like Leu462, Gly463, Ala483, Val484, Leu538, Leu594, and Val595 as shown in FIG. 1G. The activation loop is extended continuation of the T-loop located in the C-lobe, it is considered as an important regulatory element in the protein kinase, the T-loop continues to the P+1 loop and the αF-helix (FIG. 1H).

To investigate the stability of the model, the inventors performed a classical molecular dynamics simulation in explicit solvent in 0.1M slat concentration for 500 ns at 300 K. The root-mean-square displacement (RMSD) in heavy atom positions converged to 4.5 Å after 500 ns, maintaining the predicted overall fold of the protein. The final TLK1 structure from the simulation produced good validation scores, with a MolProbilty score of 1.49 and QMEAN score of −1.26. It was found to be highly accurate in the Ramachandran Plot with majority of residues (98%) were found in the favored and allowed region.

Figure 2A:
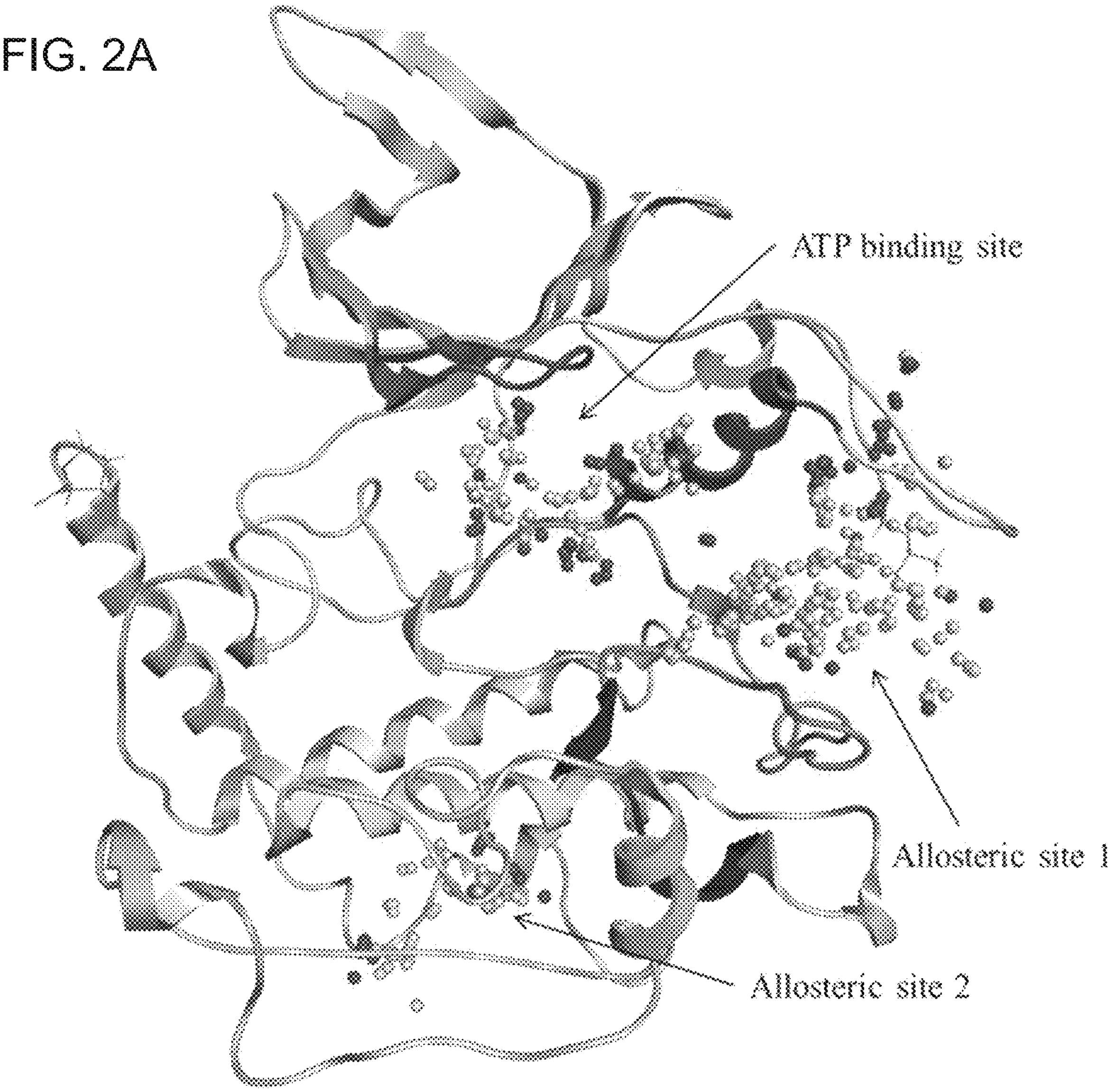
FIGS. 2A-2D show a Homology Model and Molecular Docking studies of new phenothiazine derivative (J54) with the modeled Human TLK1B kinase domain.
Figure 2B:
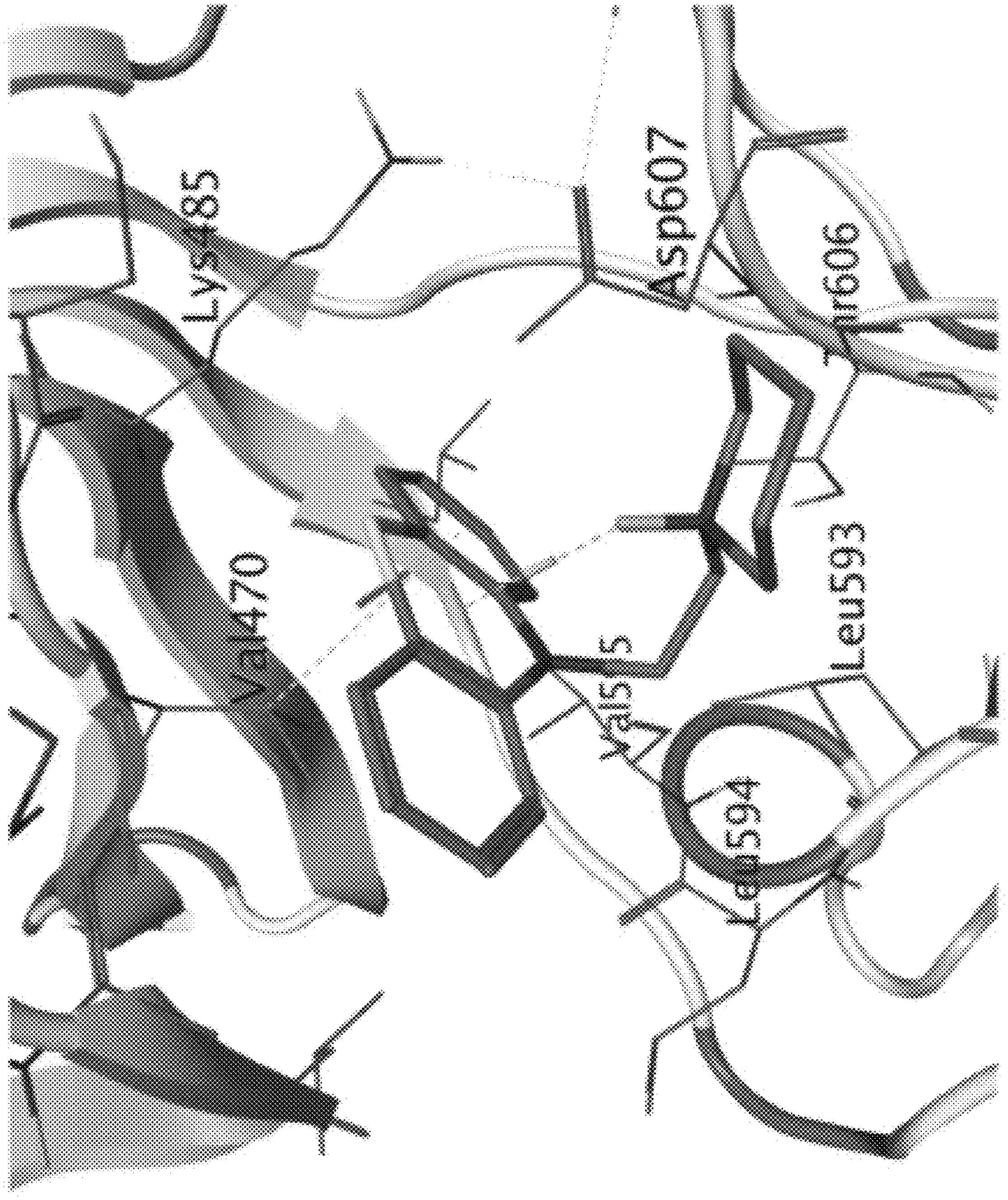
Figure 2C:
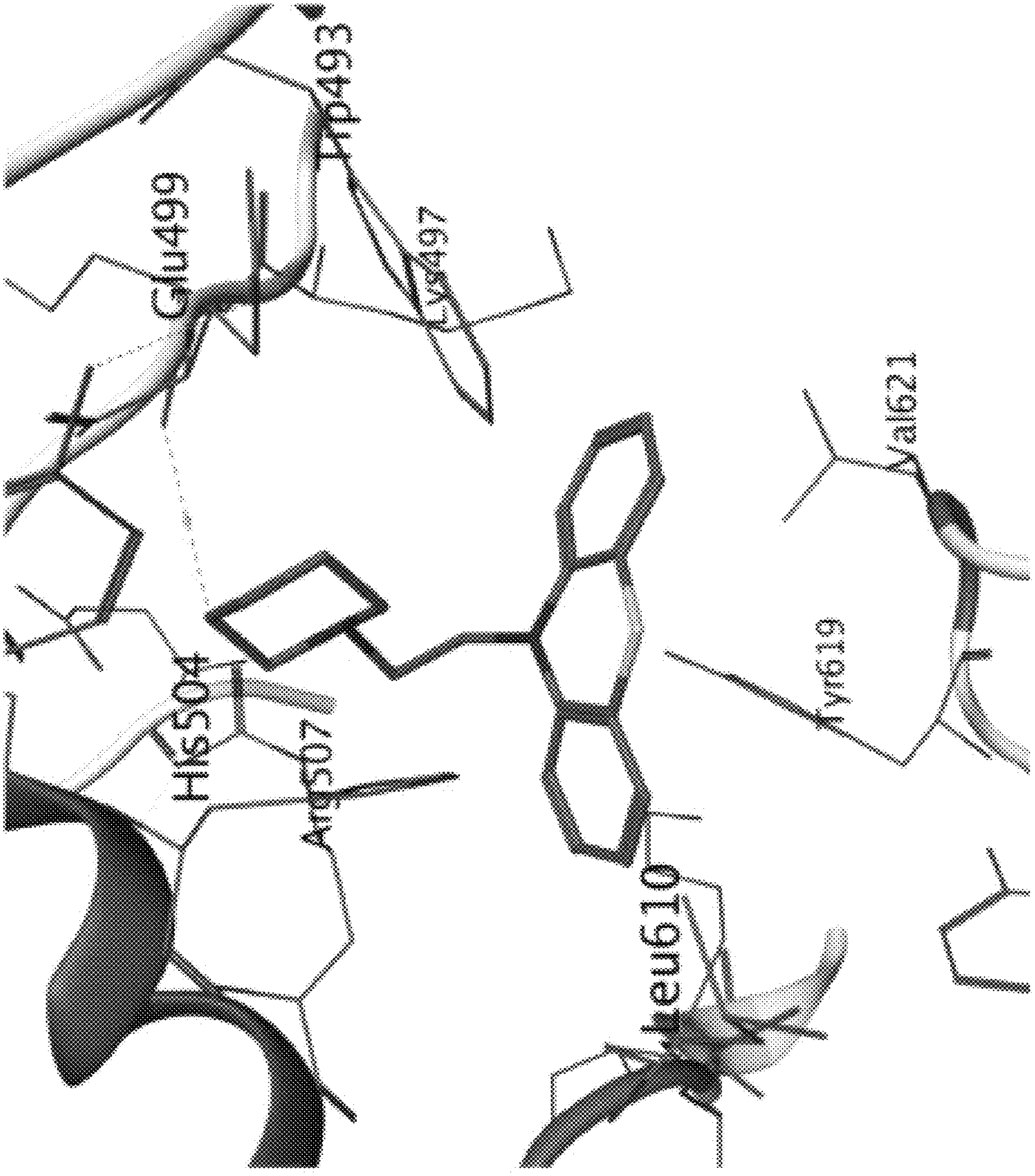
Figure 2D:
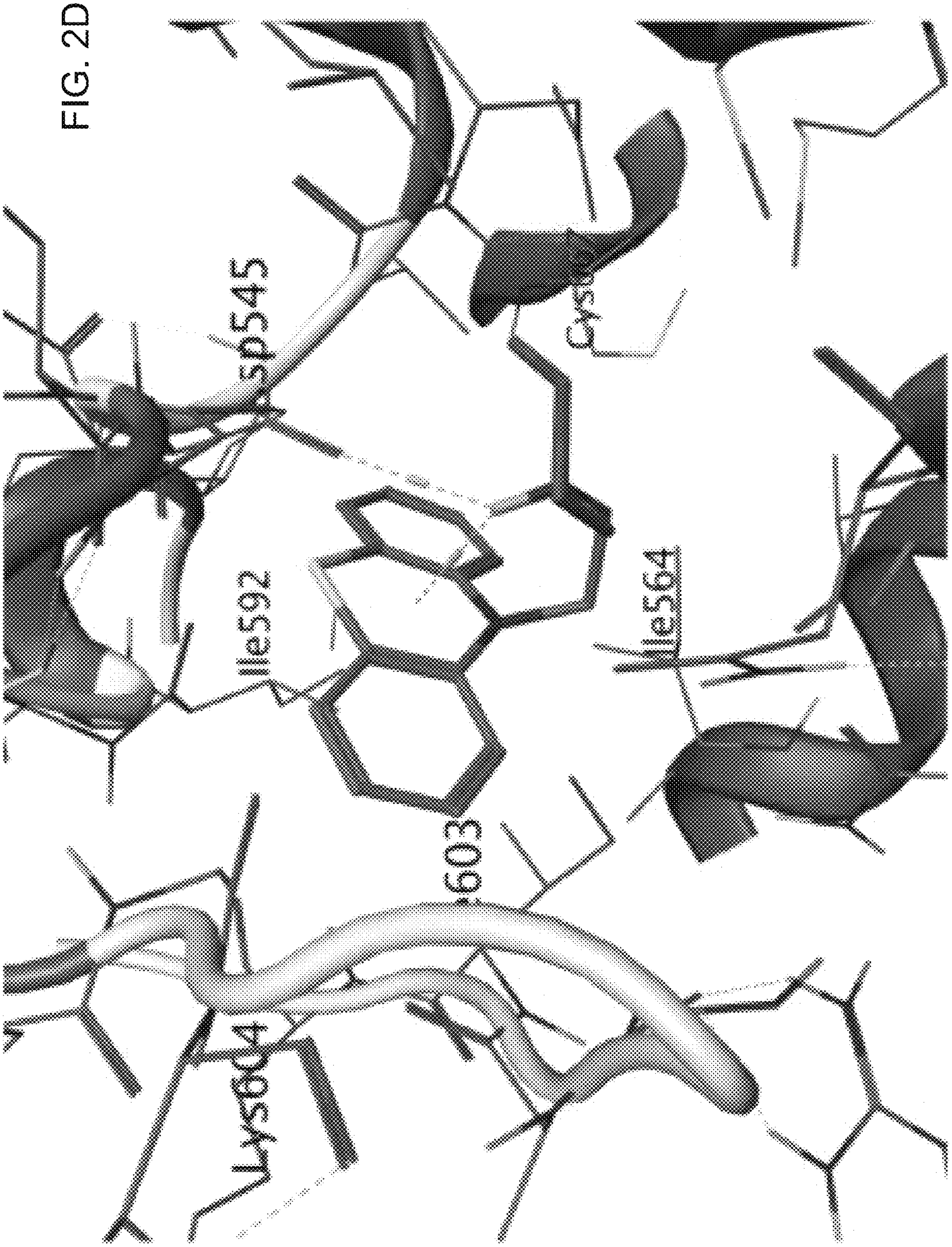
Figure 3B:
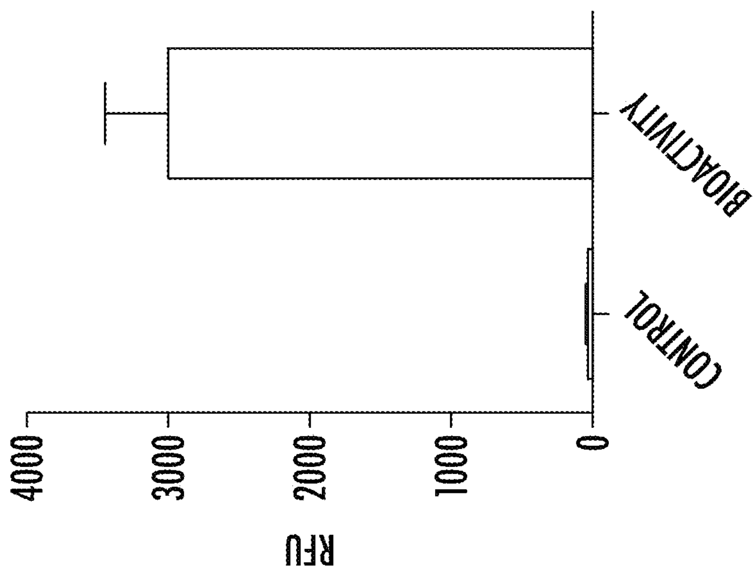
FIGS. 3A-3M show recombinant TLK1B purified to homogeneity.
Figure 3A:
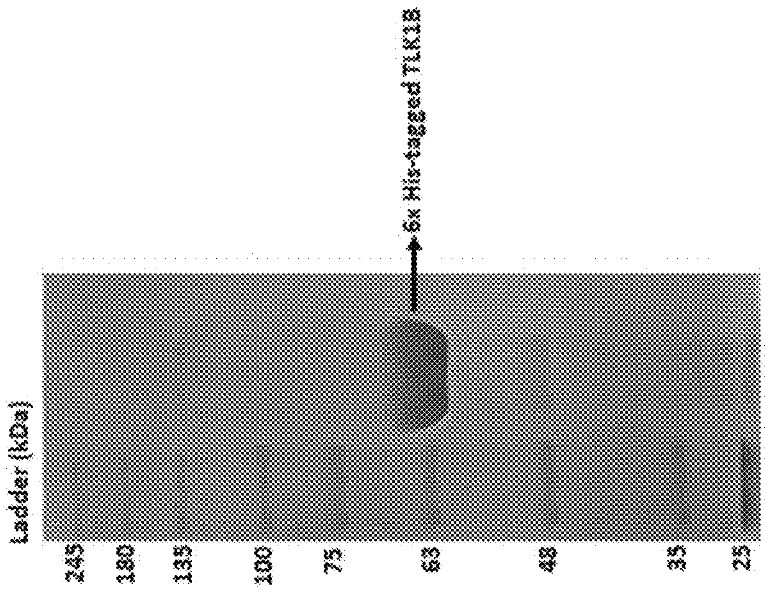
Figure 3C:
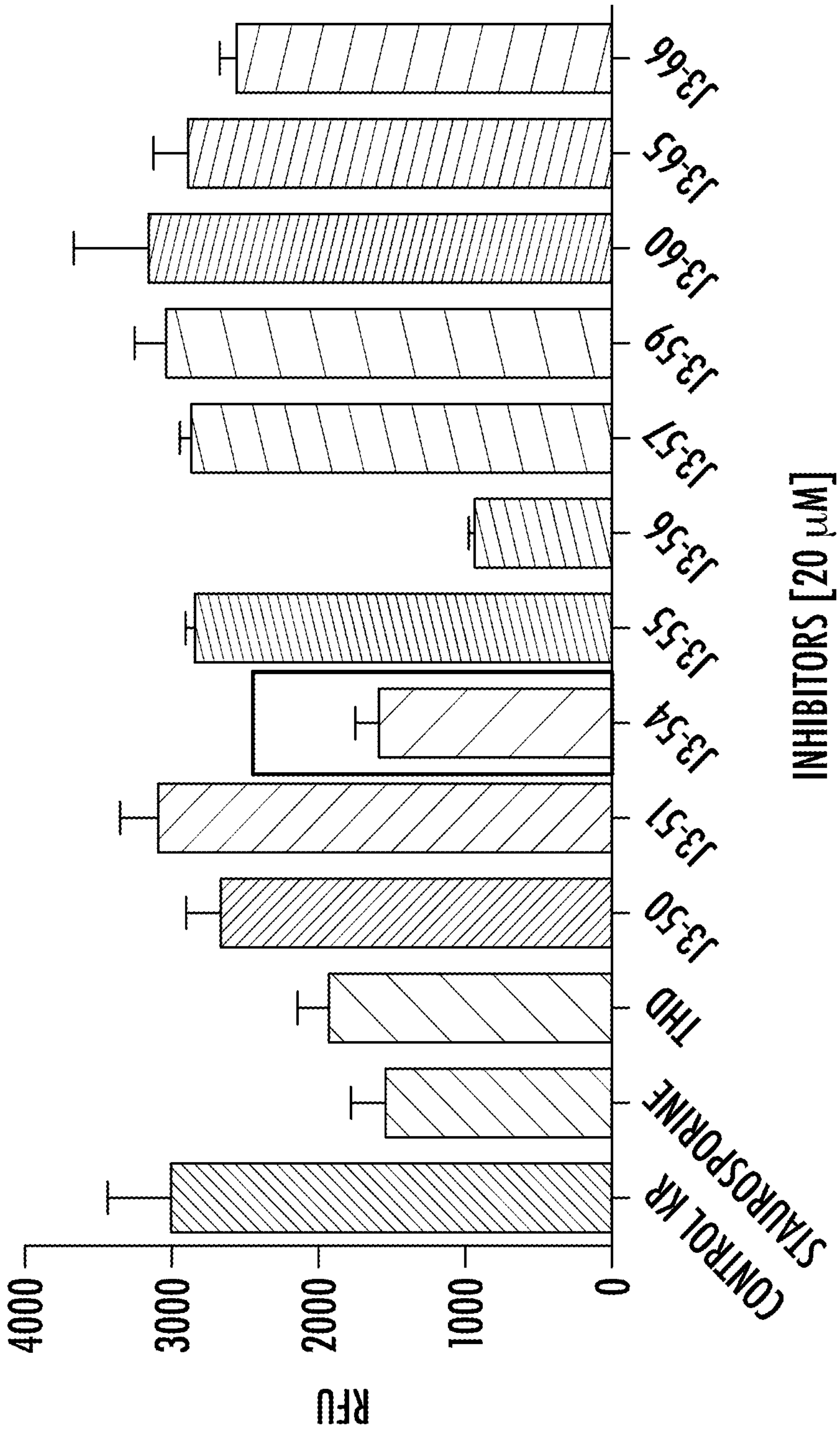
Figure 3D:
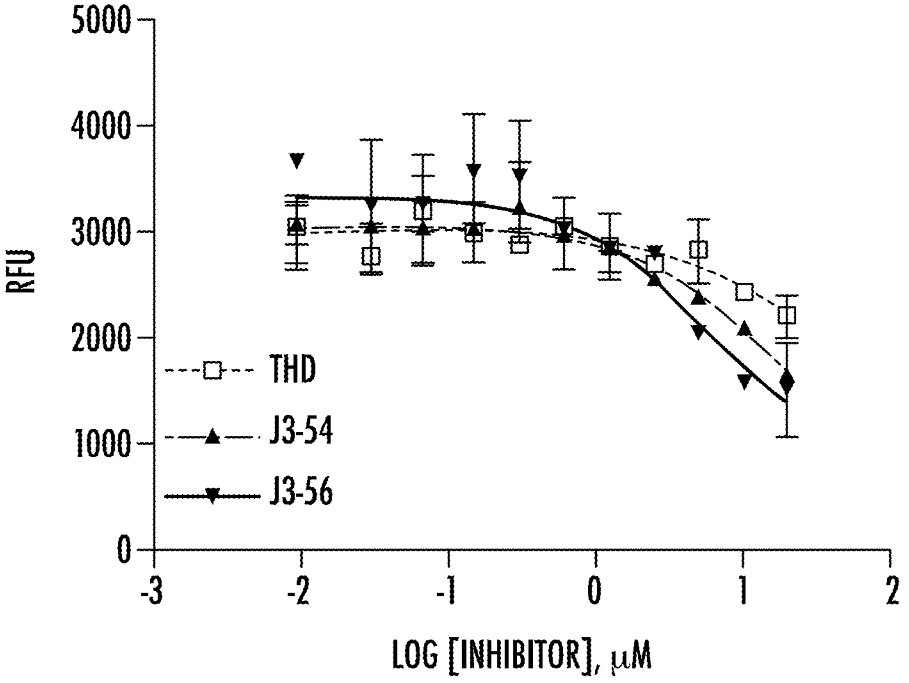
Figure 3E:
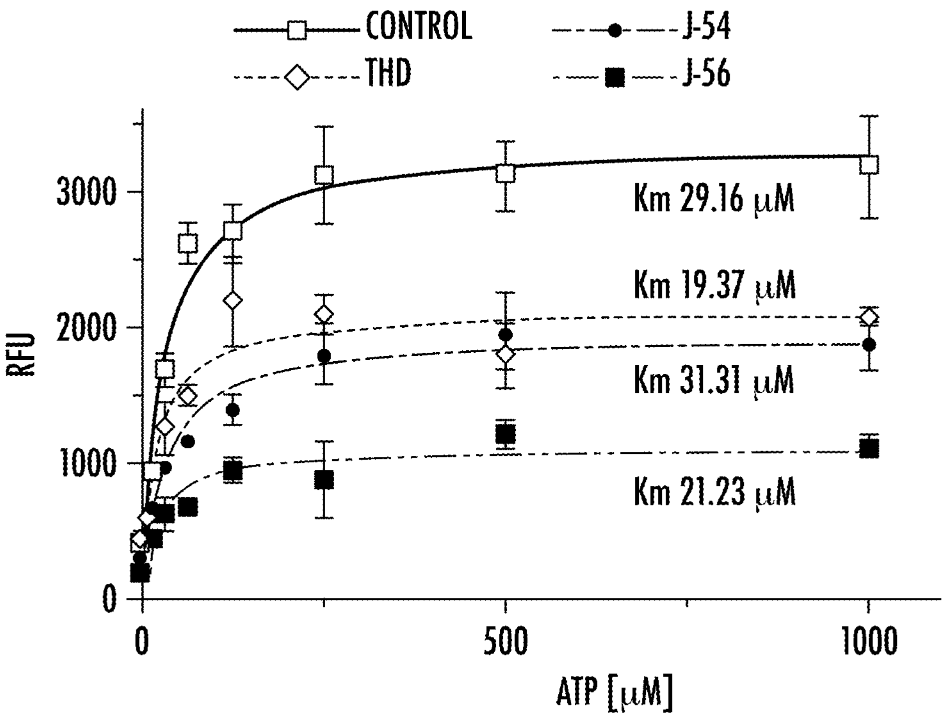
Figure 3F:
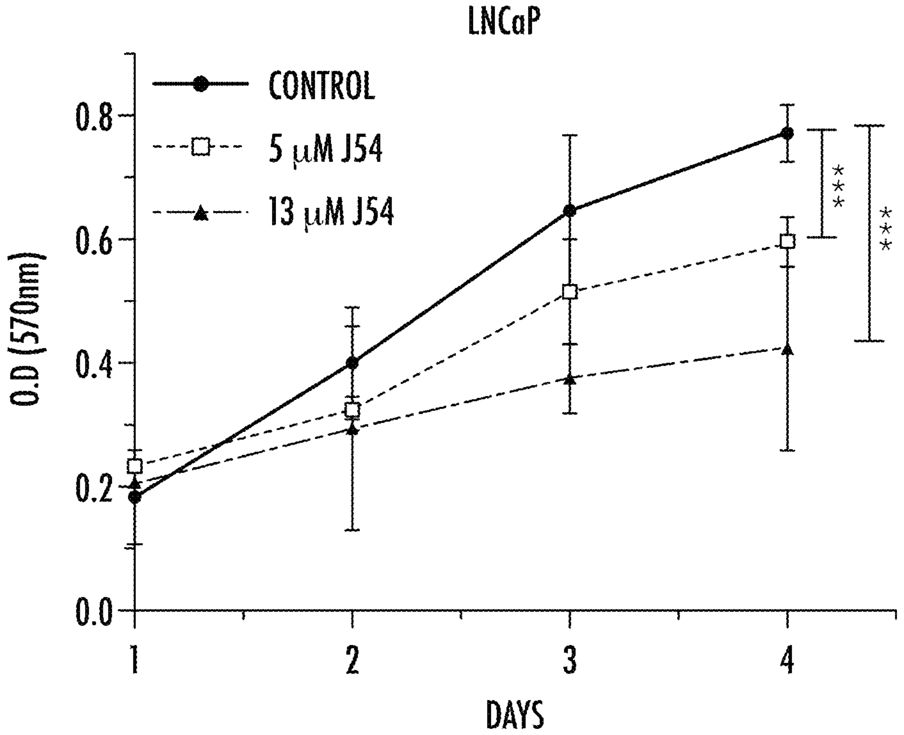
Figure 3G:
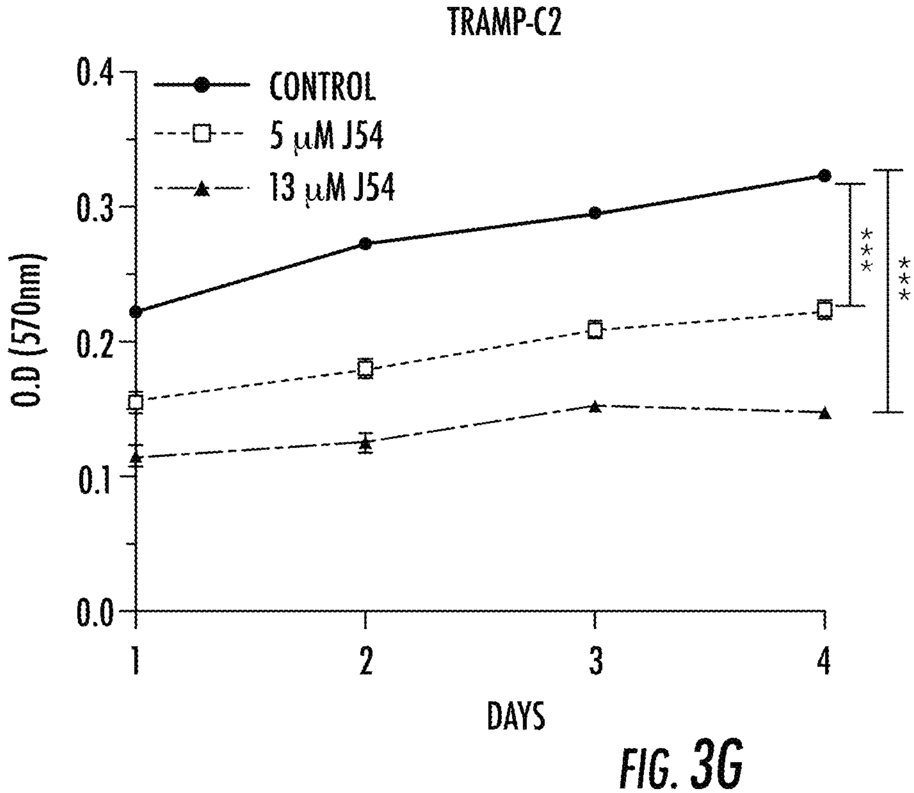
Figure 3H:
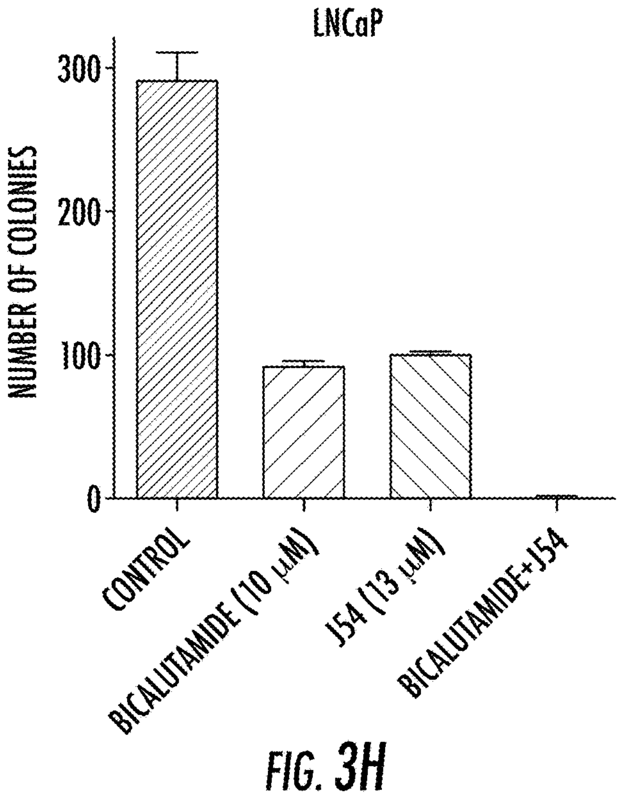
Figure 3I:
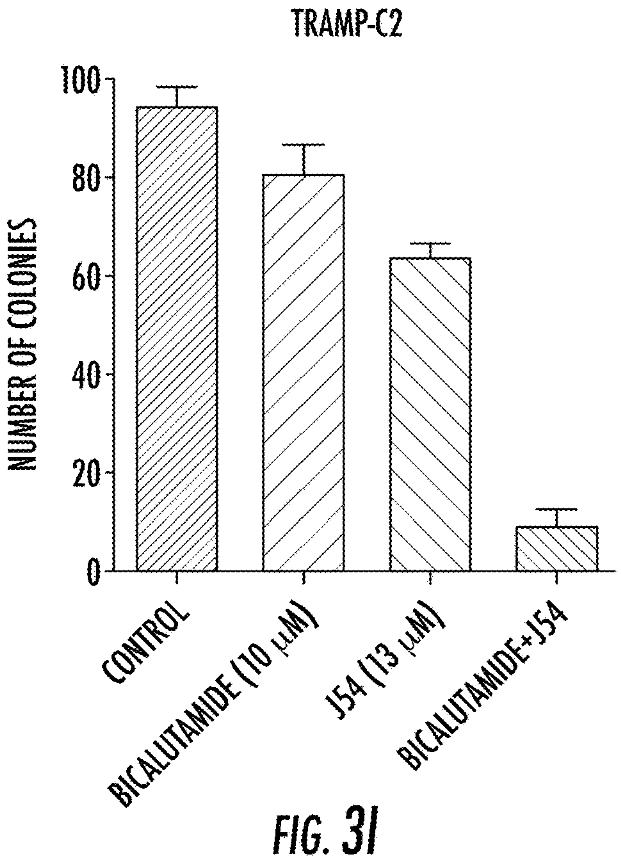
Figure 3J:
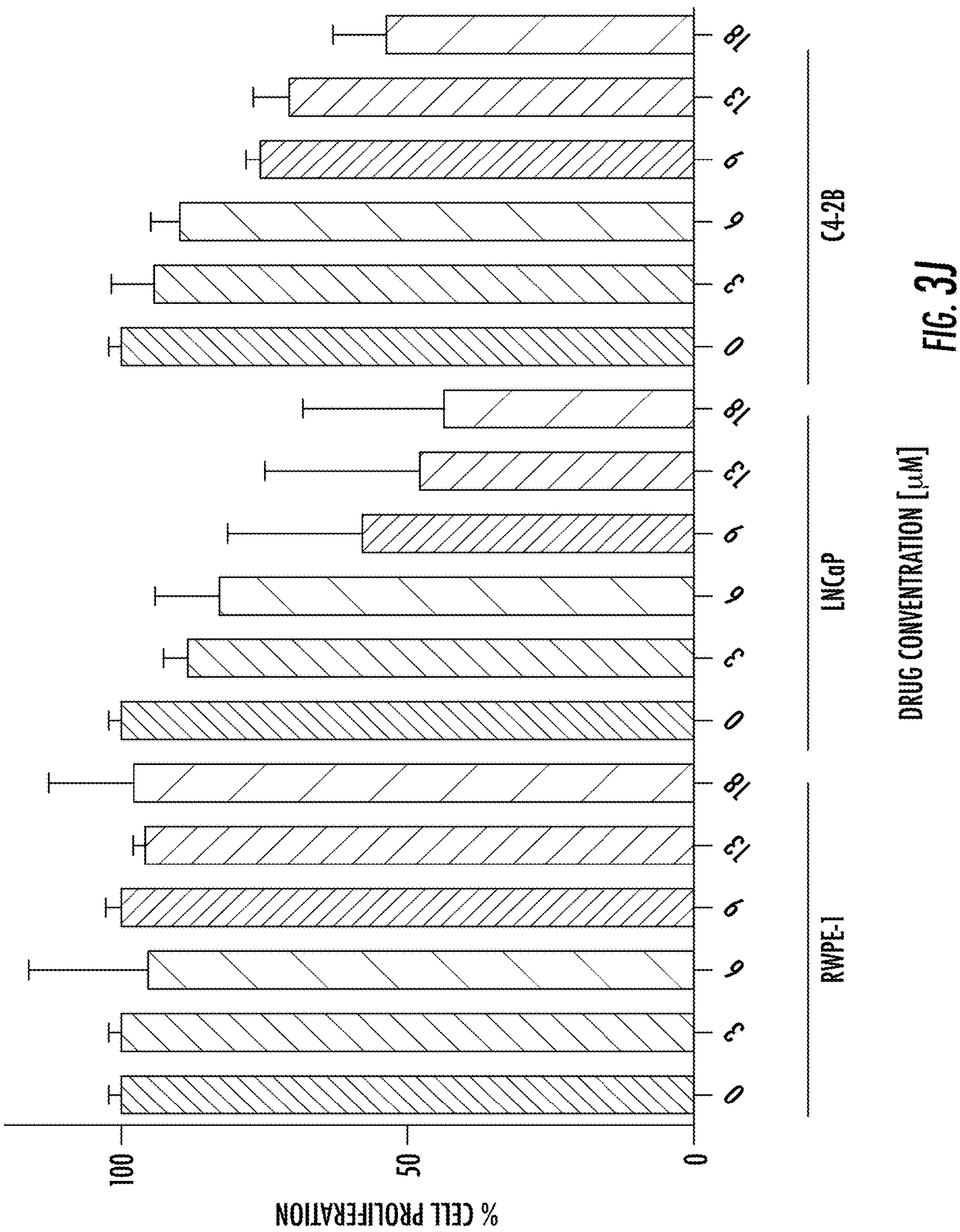
Figure 3K:
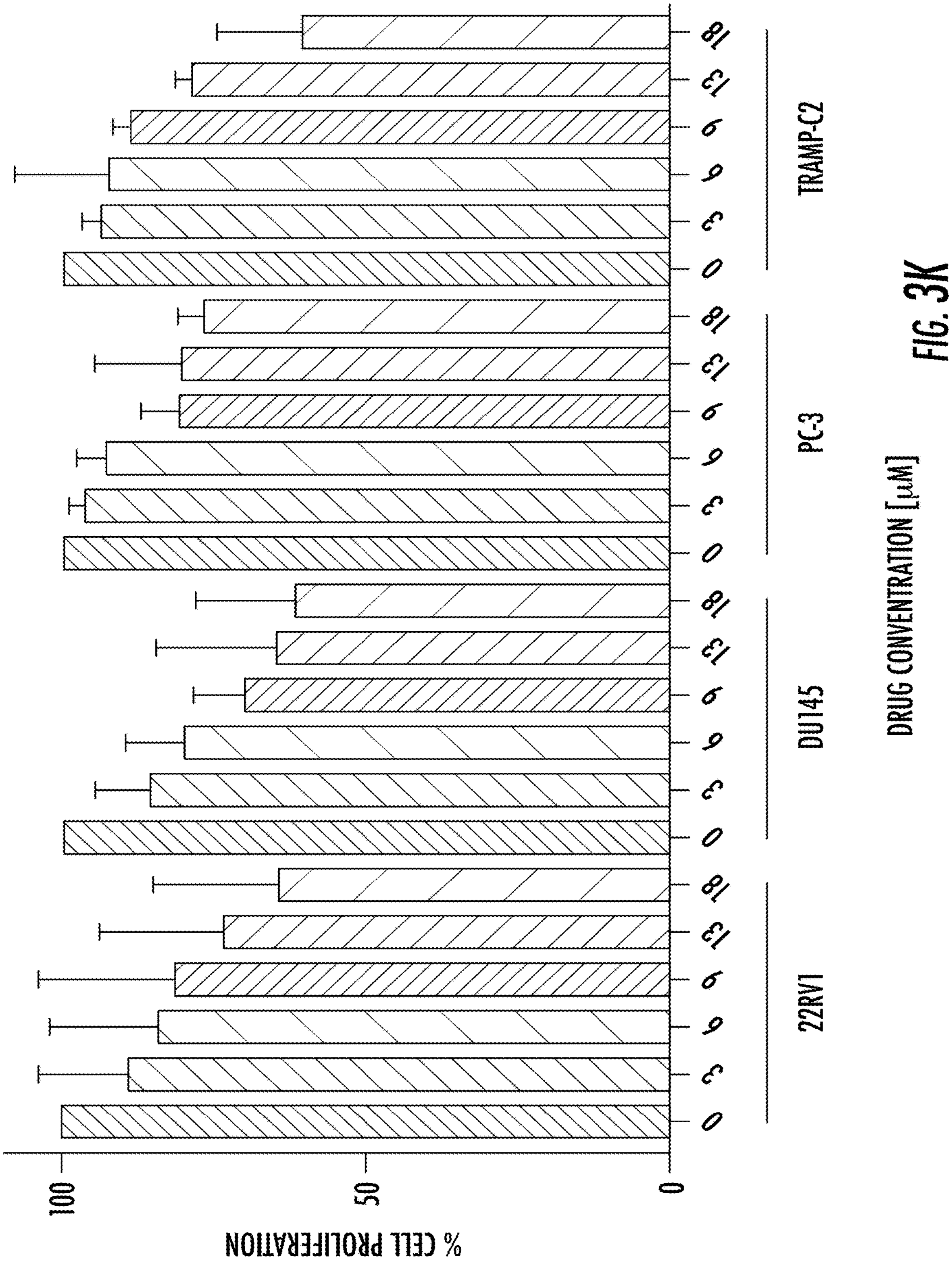
Figure 3L:
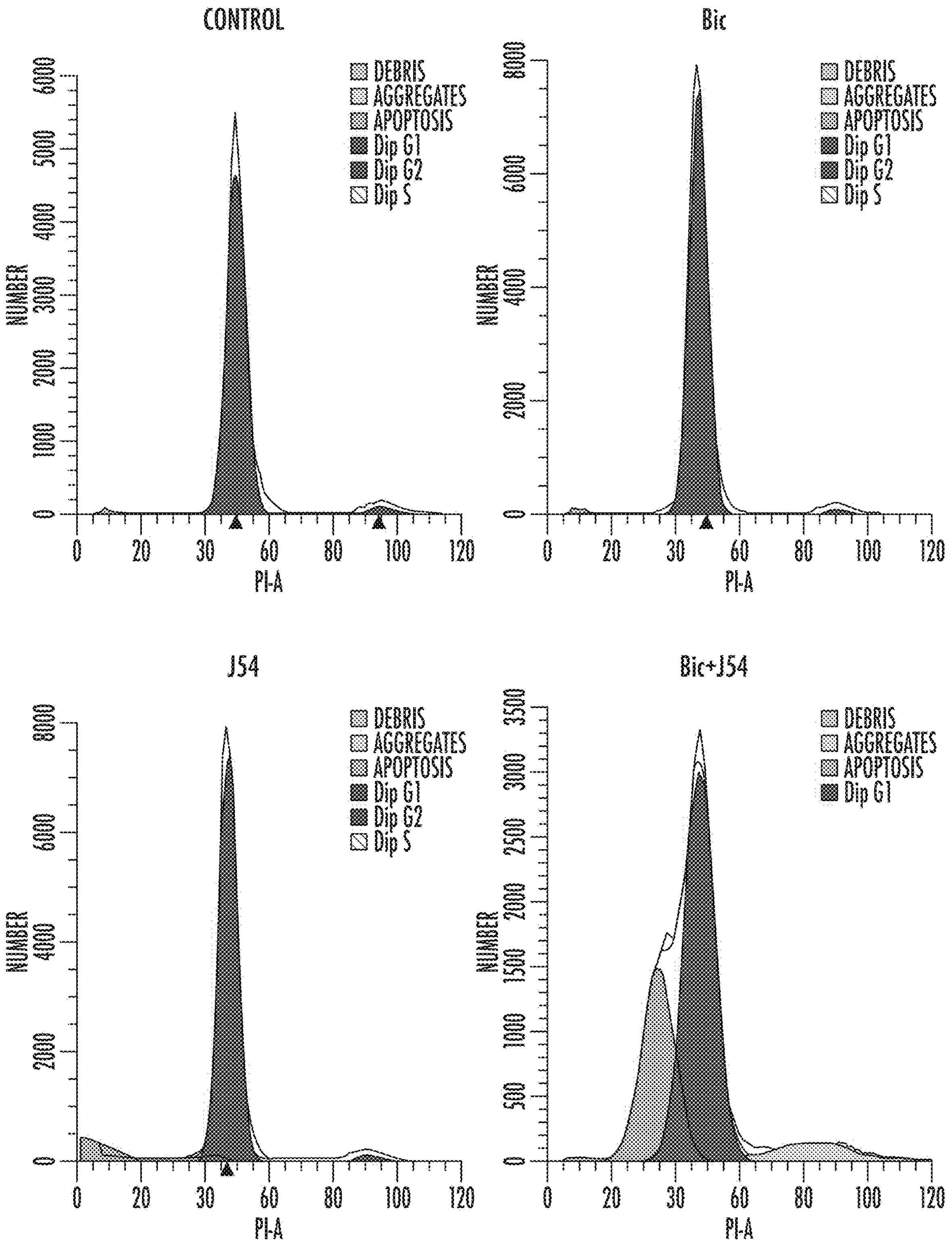
Figure 3M:
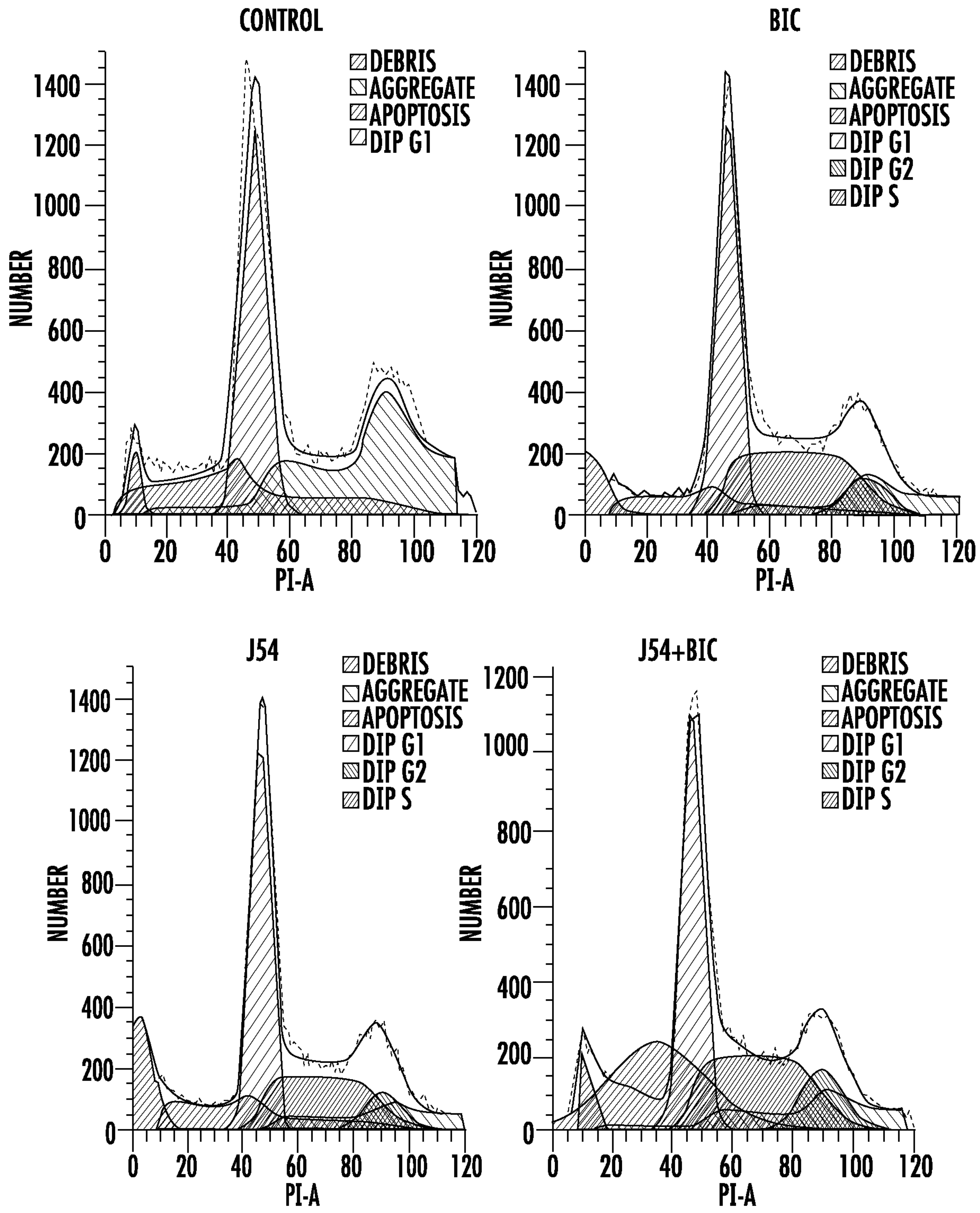
Figure 4A:
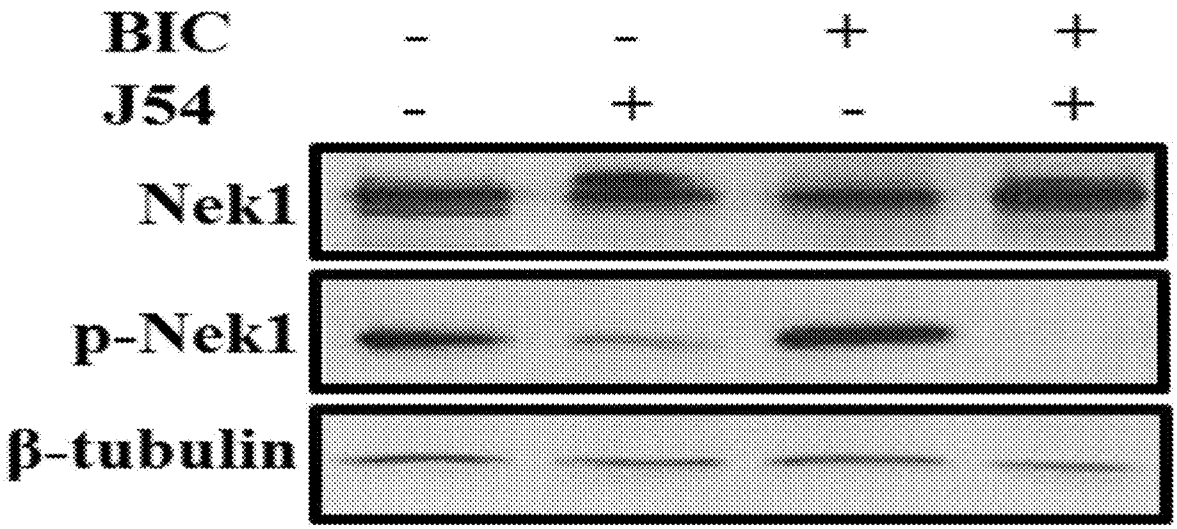
FIGS. 4A-4G show J54 treatment affects the expression of different DNA damage response pathway proteins in combination with Bicalutamide. Shown are Western blots for p-Nek1, TLK1B, p-H2AX, c-PARP, Cleaved Caspase 8, PCNA, p21, p-ATR, and p-Chk1, in the absence of and treated with J54, Bicalutamide, and both J54 and Bicalutamide in LNCaP Cells and TRAMP-C2 cells.
Figure 4B:
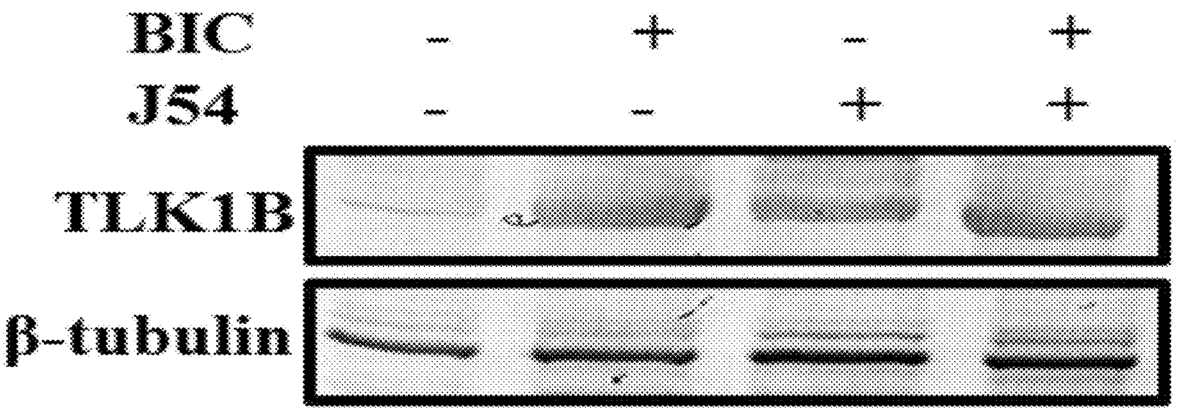
Figure 4C:
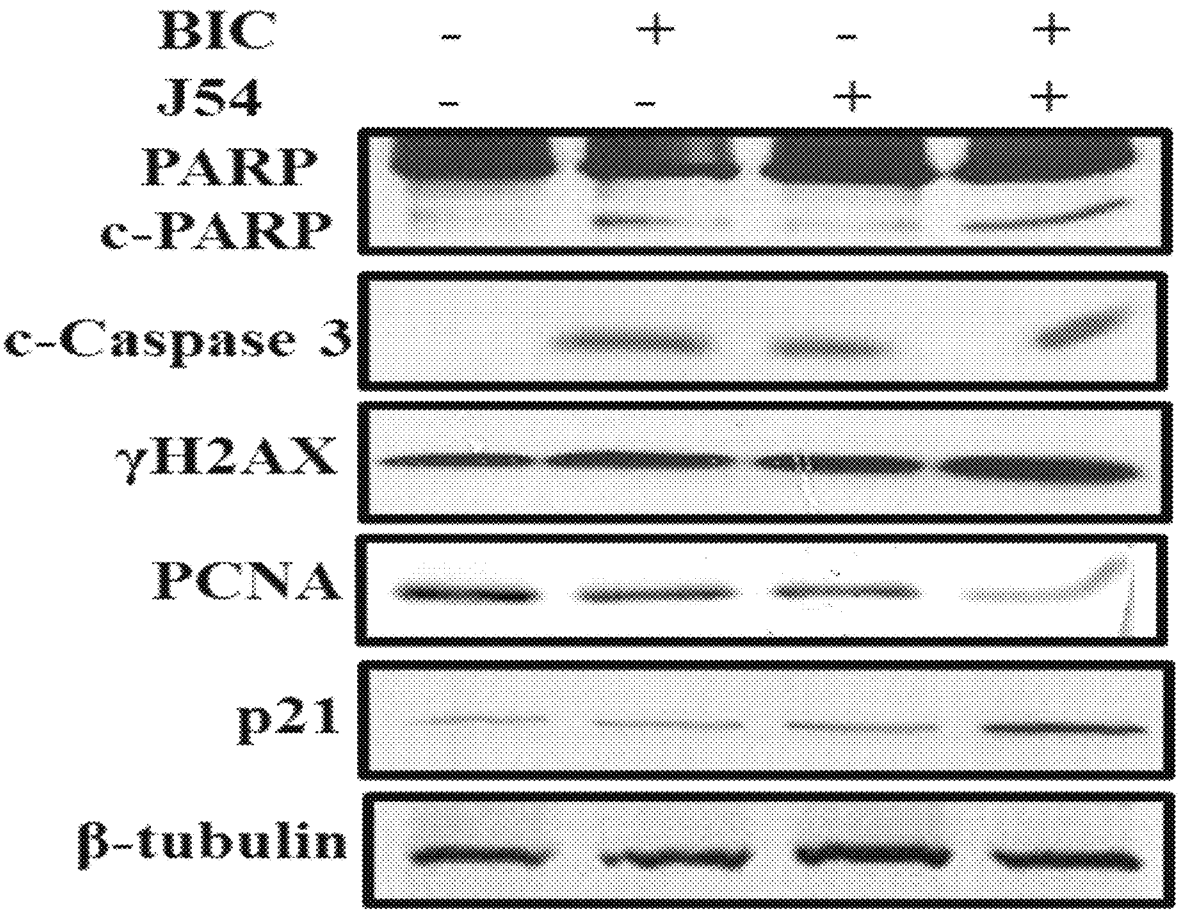
Figure 4D:
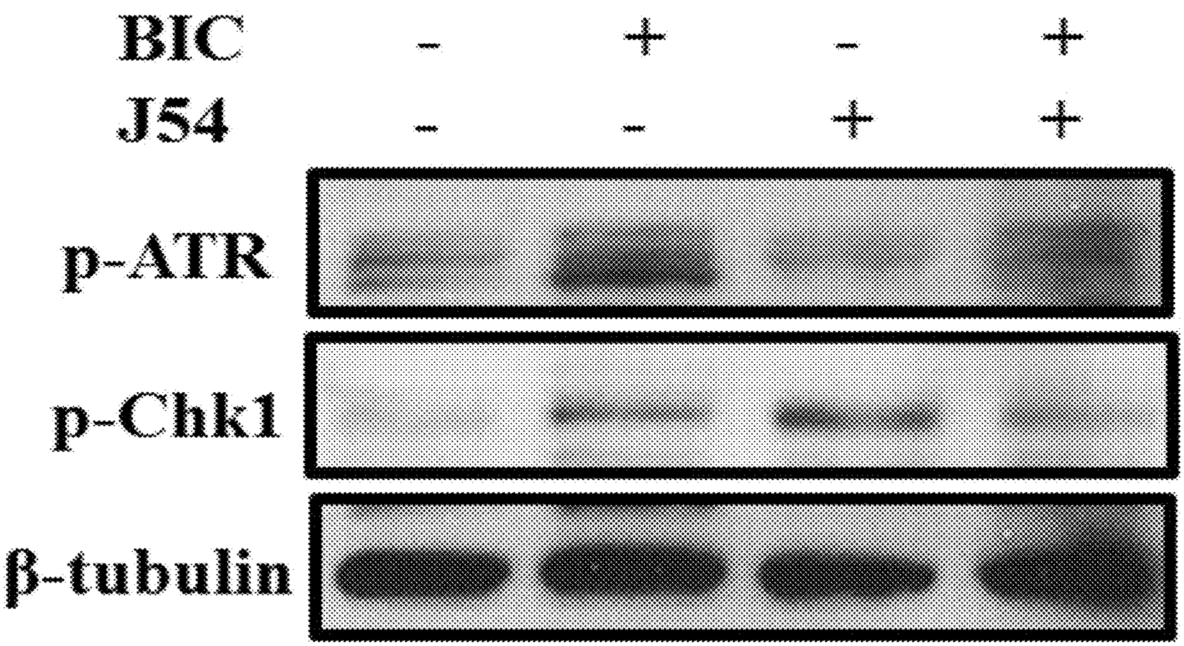
Figure 4E:
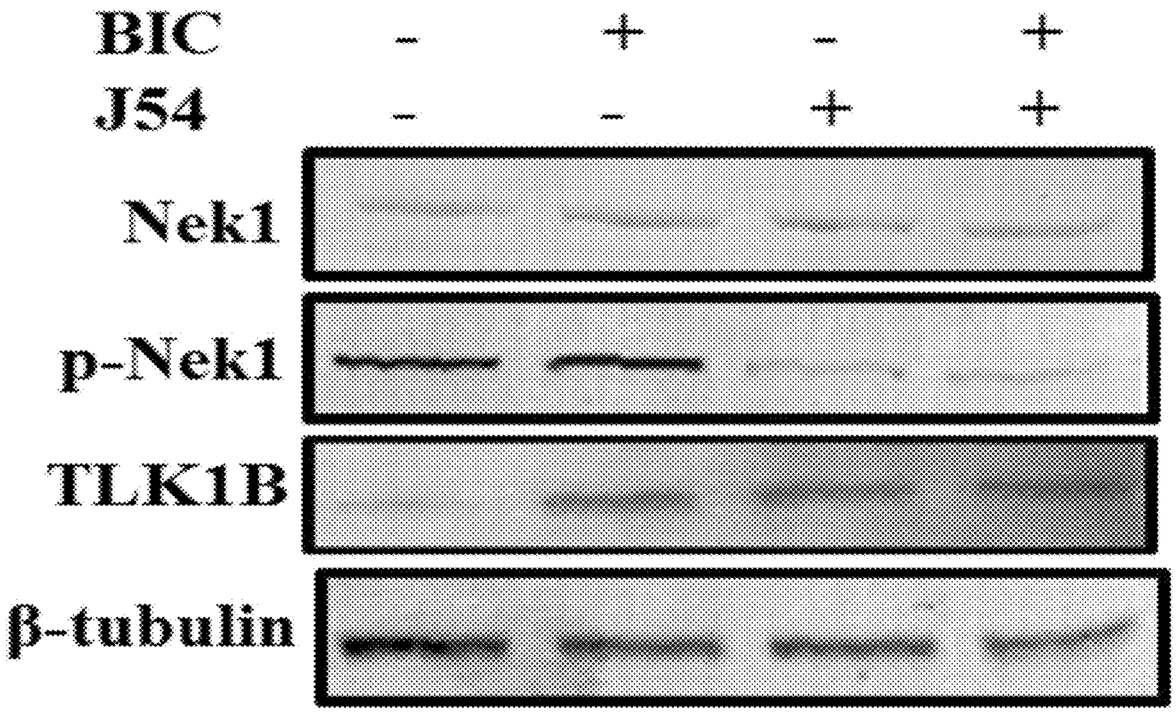
Figure 4F:
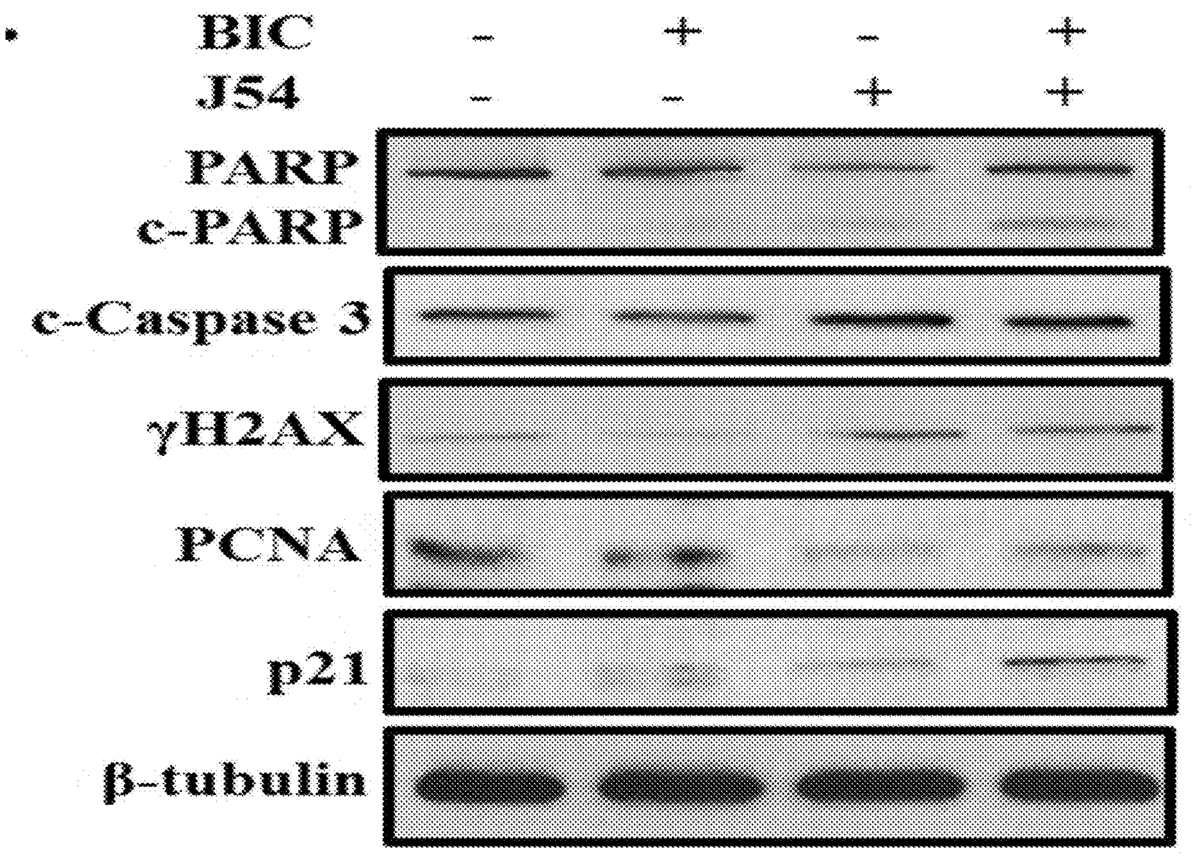
Figure 4G:
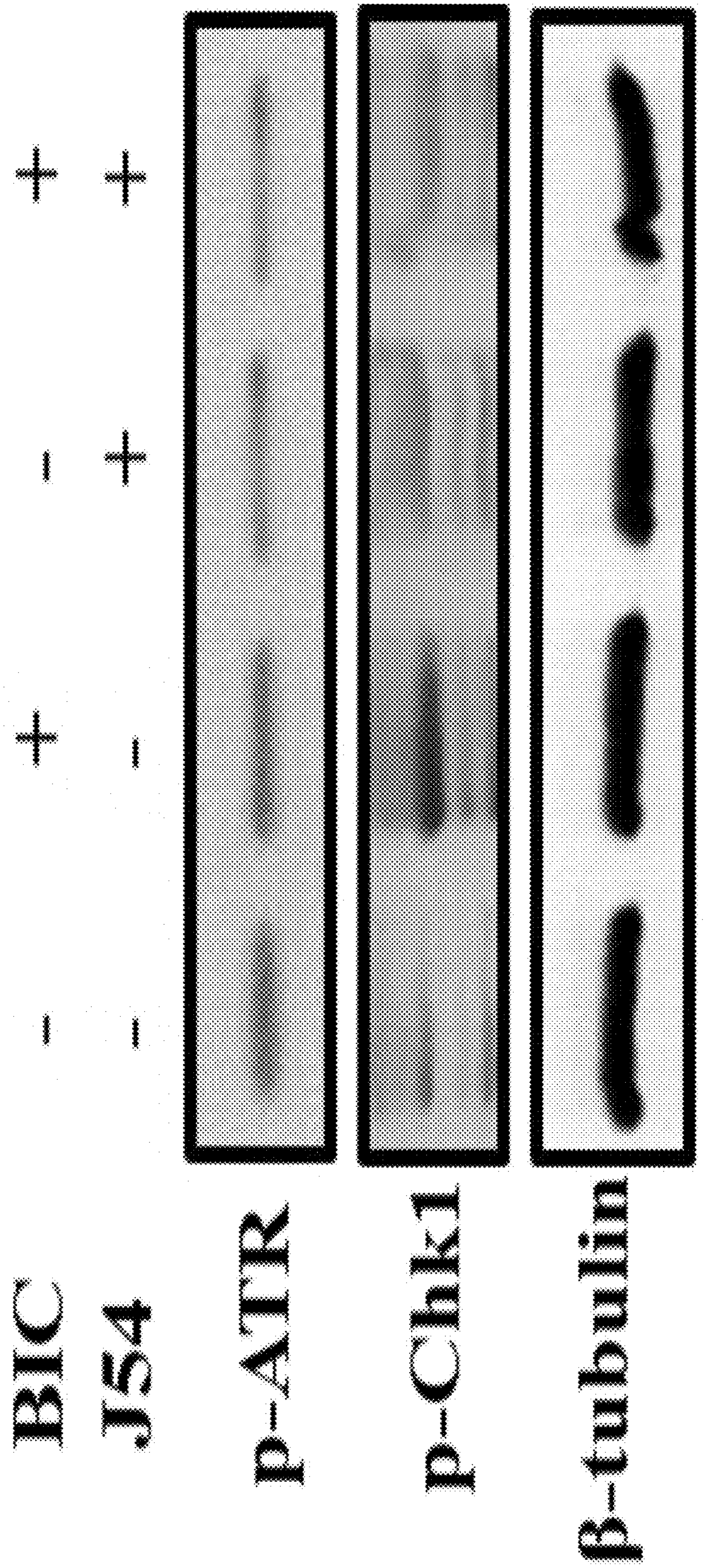

Three distinct active sites were identified by the SiteFinder and favorable pockets in MD-refined structure for performing molecular docking studies (FIG. 2A). The first site was obviously the ATP binding site, remaining two are identified as the allosteric site 1 and 2. The allosteric site 1 is adjacent to the ATP binding site in the N-lobe, whereas the second allosteric site is found buried in the C-lobe.

The favorable pockets in the MD-refined TLK1 structure are shown in FIG. 2A. The allosteric pocket 2 contained 198 spheres with a propensity for ligand binding (PLB) score of 2.75. The active site 1 contained 108 spheres with a PLB score of 2.43 and the allosteric site 3 contained 72 spheres with PLB score of 1.80. The inventors note that a score of greater than 1.00 is considered highly druggable. Molecular docking studies were performed on all the three active sites. It was found that compound J3-54 could bind in all the three sites. In site 1 it docks at the ATP binding site and has dock score of −8.2966 (Chemgauss4 scoring function), it also shows ionic interaction with Asp607. In a second case, the compound docks at allosteric site-1 with a better docking score of −10.0381. The morpholine head forming hydrogen bond with Glu499 and ligand nucleus exposed towards solvent. The ligand binds to the second allosteric site but with docking score of 2.4059, the morpholine head form a hydrogen bond with the Asp545. This suggests that the favored site for interaction between the ligand and receptor would be the allosteric region of the TLK1 protein.

Material and Methods: TLK1 homology modelling. Homology modelling was performed de novo via the ROBETTA full chain protein structure predictive server, due to the absence of a template for comparative modelling. The model was constructed by the hierarchical Ginzu screening method. The modelled TLK1 structure was analyzed by a series of validation methods for its reliability and consistency. The model was first analyzed for its stereochemical quality using the MOE software package. It provided with analysis of steric problems within the protein and high-accuracy Ramachandran Plot (RC-plot). The φ/ψ angles were well within the allowed region. The majority of residues (98%) were found in the favored and allowed region. Similar results were obtained on second set of validation of the model using the MolProbity server. The MolProbity score was 1.49, It showed the clash score for all atoms to be 0.51 and six outlier rotamer. The energetic properties of TLK1 homology model was performed on the QMEAN web server. Qualitative Model Energy analysis (QMEAN) was carried out of TLK1 homology model which revealed a QMEAN Value of −1.26.

Docking study. The molecular docking studies were performed on the Openeye and MOE package. The homology model after molecular dynamics simulation for 500 ns was subjected to molecular docking with compounds from the 'J3' series of synthesized molecules. The energy minimized and post-MD processed homology model was analyzed in MOE for determination of active sites. Based on the active sites, the model was subjected to molecular docking in the three different sites: ATP-binding site, allosteric site-1 and allosteric site-2. Docked poses were clustered and analyzed for score and fit.

Molecular dynamics simulation. System preparation: MD simulations were performed using the AMBER16 software package. The TLK1 homology model was immersed in truncated octahedron of TIP3P water giving a total of 10349 water molecules. Na+ and Cl− counter ions were added to neutralize the system and achieve an ionic strength of 0.1 M. The ff14SB force field was used to model the protein.

Unbiased MD simulation: Simulations were performed using the pmemd.cuda module. Simulations were run at 300 K using the Langevin thermostat with a collision frequency of 2 ps-1; and 1 atm using a Monte Carlo barostat with volume exchange attempts every 100 fs. A 2 fs integration step was employed. Covalent bonds involving hydrogen were constrained using SHAKE. A cutoff of 8 A was used for short range nonbonded interactions whilst long range electrostatics were treated using the particle mesh Ewald method. Equilibration consisted of rounds of NVT and NPT equilibration for 10 ns in total. Production MD run was performed for 500 ns.

Continued J54/J56 Investigation

Through in-vitro kinase assays and molecular docking studies, the inventors report the synthesis and biological evaluation of a new phenothiazine with potent TLK1 inhibitory activity as a treatment for Prostate Cancer still responsive to androgen-deprivation therapy. Most PCa deaths result from progressive failure in standard ADT, leading to metastatic castration-resistant PCa. Treatments that can suppress the conversion to mCRPC have the best potential to be rapidly implemented in the clinics. ADT results in increased expression of TLK1B, a key kinase upstream of NEK 1 and ATR and mediating the DDR that typically results in a temporary cell cycle arrest of androgen responsive PCa cells, while its abrogation leads to apoptosis. The inventors now studied J54 as new potent inhibitor of this axis and as mediator of apoptosis in-vitro and in LNCaP xenografts, which has potential for clinical investigation in combination with ADT. J54 has low affinity for the dopamine receptor (DR2) in modelling studies and direct competitive radio-assays, and weak detrimental behavioral effects in mice and *C. elegans*. Thus, J54 does not appear to have DR2 antagonistic side effects that can include cardiac arrhythmia.

J54, a novel potent inhibitor of TLK1, was synthesized based on in silico docking studies and kinase assays.

J54 leads to apoptosis of PCa cells in combination with Androgen Deprivation Therapy in several PCa cells in LNCaP xenografts.

J54 has low affinity for recombinant dopamine receptors and low antidopaminergic activity in animals.

TLK1B is selectively increased upon ADT, thereby providing a specific target for PCa cells rather than generally targeting the DDR, and thus can mediate cancer specificity.

The novelty consists of a new specific inhibitor of TLK1 for PCa therapy without the antidopaminergic side effects of previously studied phenothiazines.

J3-54 (also called "J54"). The compound J54 is properly named 4-(2-(10H-phenothiazin-10-yl) ethyl) morpholine. Description of the synthesis of J54 is in the Appendix. The chemical structure of J54 follows:

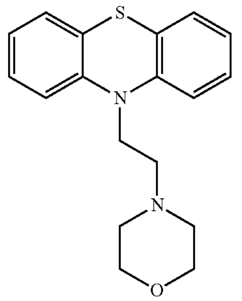 [SMILES: c1ccc2c(c1)Sc1ccccc1N2CCN1CCOCC1]

J3-56 (also called "J56"). The compound J56 is properly named 10-methyl-10H-phenothiazine. Description of the synthesis of J56 is in the Appendix. Its chemical structure of J56 follows.

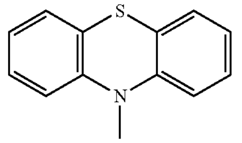

Prostate Cancer (PCa) is a leading cause of morbidity and mortality of men in the western world. The standard of care for advanced PCa after failure of localized treatments is androgen-deprivation therapy (ADT) and anti-androgens, which provides respite from disease progression, but ultimately fails resulting in the incurable phase of the disease: mCRPC. Treatments that can suppress the conversion to mCRPC have the best potential to improve outcome and be rapidly implemented in the clinics; and this requires a clear understanding of the process of PCa cells' mechanisms of adaptation to ADT. This process has been well studied in the LNCaP cell line model, in which the inventors have recently elucidated some missing details. Androgen deprivation of LNCaP cells results in loss of AR function with a compensatory pro-survival activation of mTOR and concomitant implementation of a cell division arrest by activation of the DNA Damage Response (DDR) mediated by ATR-Chk1 or ATM-Chk2. The DDR is likely activated due to the role played by the AR as replication licensing factor in combination with the mTOR dependent increased expression of TLK1B and resulting activation of the Nek1>ATR>Chk1 axis. Additional work from the inventors' lab suggested that this may be a conserved nexus in additional cell models; in the TRAMP mouse; and probably in many patients, since the specific activating phosphorylation of Nek1 by TLK1 correlates with the Gleason score. The resulting cell cycle arrest is a survival mechanism for PCa cells, which remain quiescent until they reprogram and adapt to Androgen Independent (A1) growth. An attractive strategy to prevent this process would be to bypass the cell cycle arrest via inhibition of ATM or ATR, causing the cells to undertake replication with damaged DNA that would cause mitotic catastrophe, a strategy that was in fact implemented in LNCaP treated concomitantly with bicalutamide and ATM inhibition. However, a limitation of this approach is how to make the inhibition of ATM or ATR specific to PCa cells to limit general toxicity. The inventors have recently demonstrated that addition of a relatively specific inhibitor of TLK, thioridazine (THD), which the inventors repurposed for the blockage of the axis, results in fact in apoptosis of LNCaP and TRAMP-C2 cells concomitantly treated with bicalutamide. In addition, it suppresses the late re-growth of PCa in the TRAMP mouse following castration. However, THD is a known anti-psychotic and has undesirable side effects. Here the inventors describe J54, a new TLK1 inhibitor, as an adjuvant to ADT for PCa.

Materials and Methods

Molecular Modelling, Docking, Molecular Dynamics Simulations and Free Energy: Details were explained in details in section A of supplementary material and methods.

Chemical synthesis of J54 and several different Phenothiazines and Protein expression and purification: Details were explained in section B of supplementary of material and methods. The full-length, 65 KDa recombinant human TLK1B (hTLK1B) for the in-vitro experiments was expressed and purified from bacteria as described earlier.

Cell lines: All PCa cell lines were obtained from American Type Culture Collection (ATCC). Cell lines can be identified by Research Resource Identifier (RRID) as available in the ExPASy Cellosaurus database for LNCaP (RRID: CVCL_0395), VCaP (RRID:CVCL_2235), RWPE-1 (RRID:CVCL_3791), LNCaP C4-2B (RRID:CVCL_4784), 22Rv1 (RRID:CVCL_1045), DU145 (RRID:CVCL_0105), PC-3 (RRID:CVCL_0035), TRAMP-C2 (RRID: CVCL_3615)). LNCaP, RWPE-1, LNCaP C4-2B, 22Rv1, DU145 and PC3 cell lines recently authenticated using STR profiling within the last three years and free from mycoplasma, and cultured as per ATCC instructions. VCaP and TRAMP-C2 cell line were purchased recently. All cell line-culture related experiments were performed with mycoplasma-free cells."

Antibodies: Antibodies used for present study is listed as FIG. 23.

LNCaP Xenograft Model and Immunohistochemistry (IHC): All animals used in this study were approved by LSUHSC IACUC and following ARRIVE guidelines. Male NOD/SCID mice (5 per group) were purchased from Jackson labs. LNCaP cells were injected as described earlier. Mice were treated IP biweekly with J54 (5 mg/kg body weight—dose estimation derived from pharmacokinetics study) and/or Bicalutamide (100 mg/kg).

Statistics: Significance between treatment groups (mean values and SDs) was performed by a one-way ANOVA followed by Tukey's multiple comparisons tests using GraphPad Prism6 software (GraphPad Software USA). p-value<0.05 (*p<0.05; p<0.01; *p<0.001) was considered to indicating a statistically significant difference.

Availability of supporting data and material: All data generated or analyzed during this study and its supplementary information files is available upon request. Limited amounts of J54 will be available upon request.

Results

Figure 8A:
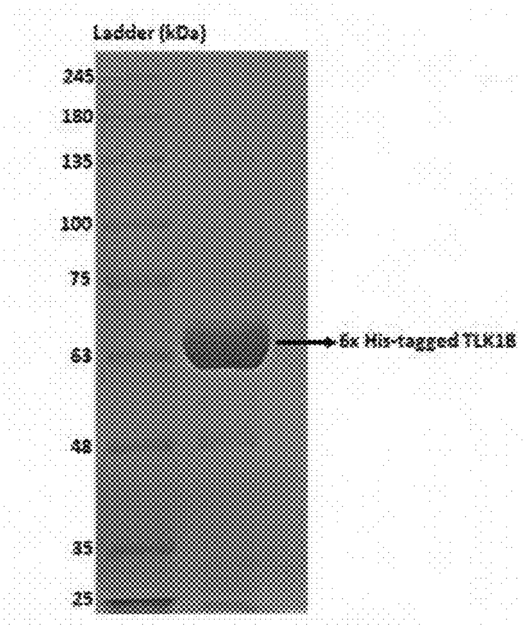
FIG. 8A-8G show further experiments into the present invention, with FIGS. 8A-8G show kinase assays, inhibitor screening, IC50 evaluation and competitive assays. Recombinant TLK1B purified to homogeneity (FIG. 8A) is active in kinase assays (FIG. 8B) and phosphorylates a specific Nek1 peptide (FIG. 8C).
Figure 8B:
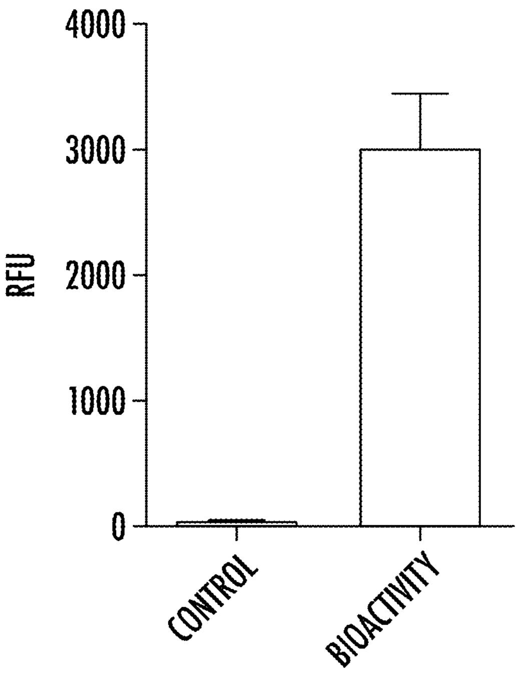
Figure 8C:
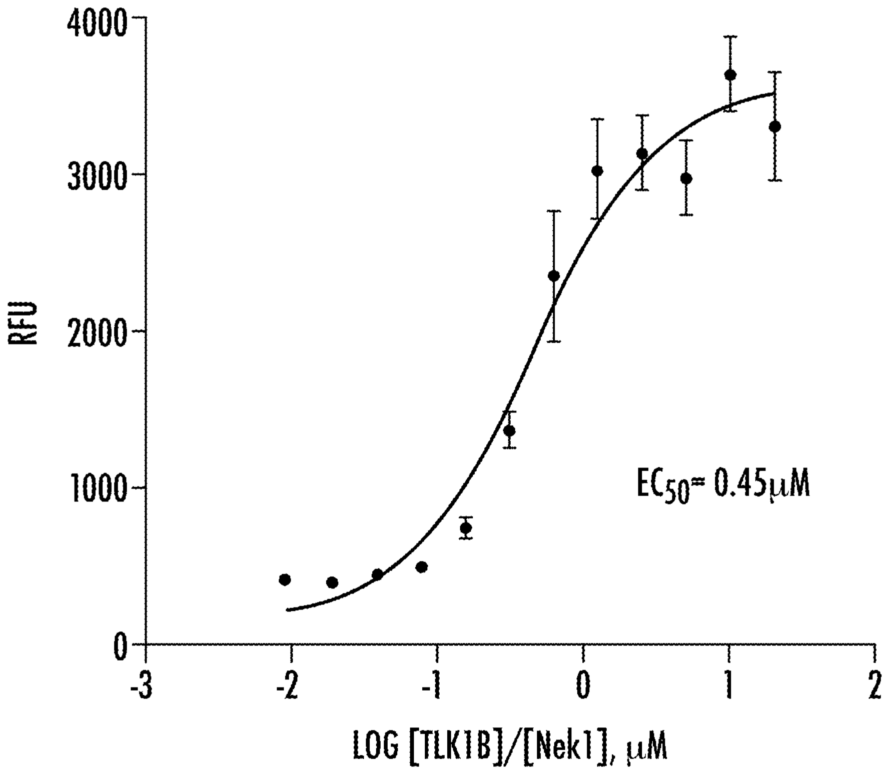
Figure 8D:
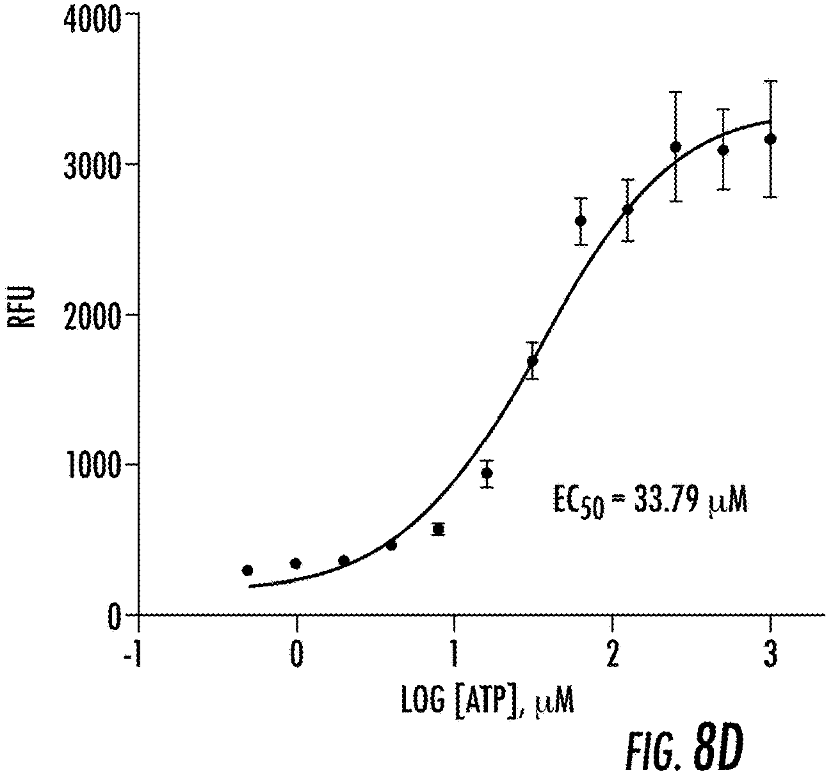
Figure 8E:
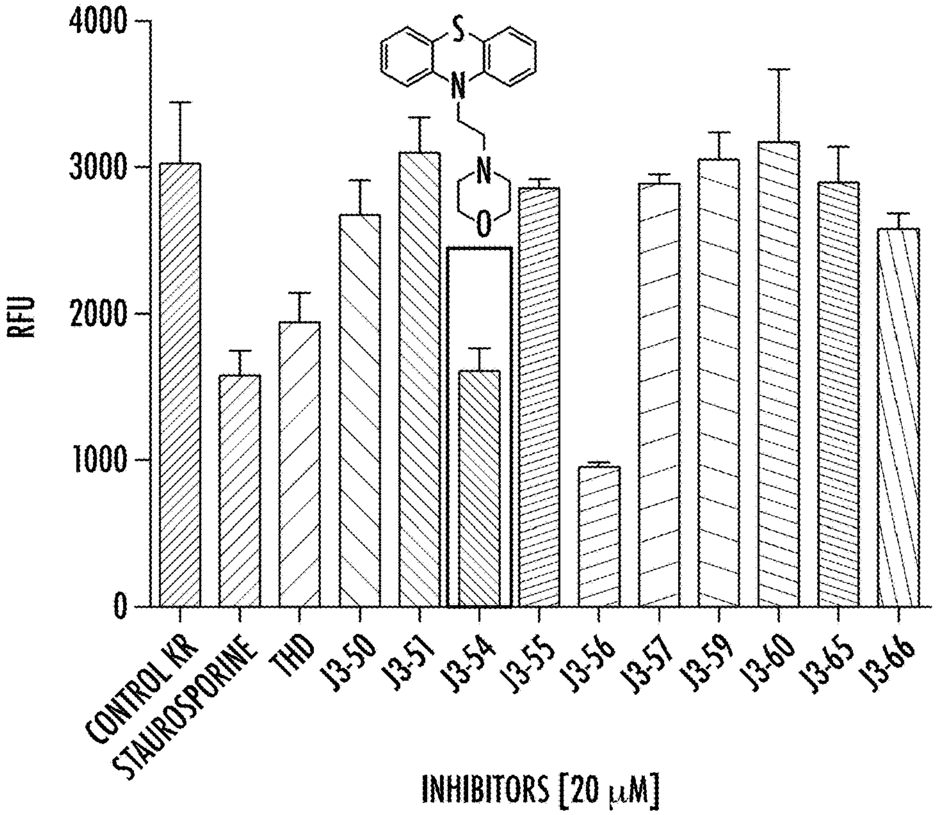
Figure 8F:
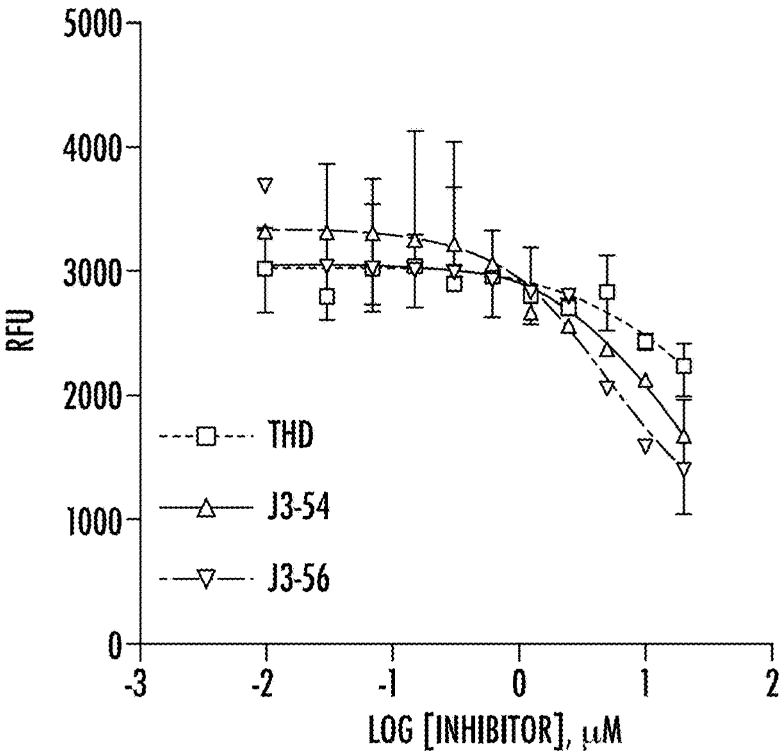
Figure 8G:
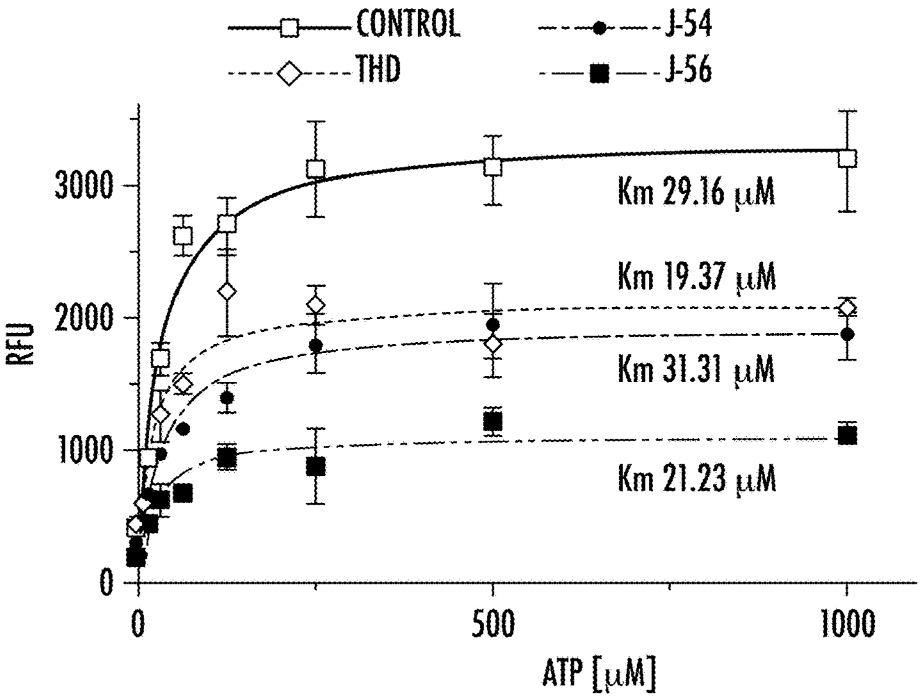

A new PTH potent inhibitor of TLK1B. A few PTH antipsychotics were identified in a screen the inventors conducted from a compounds library as good inhibitors of TLK1. To find additional inhibitors, recombinant TLK1B was purified (FIG. 8A). The enzymatic activity was determined using the ADP-Hunter reagents and a Nek1 peptide containing the T141 target site. Properties of substrate (Nek1 peptide) and ATP dependence were determined (FIG. 8B-D), and in subsequent reactions with inhibitors used at 0.1 mM, which were found to be optimal. Several structurally similar compounds were synthesized as described in the Appendix (and see NMR and MS data FIGS. 10 and 11) and tested at 20 μM (FIGS. 8E and 8F). J3-54 (hereafter "J54") and J3-56 (hereafter "J56"), both being PTH derivatives, were more inhibitory than Staurosporin, which is the standard pan-kinase inhibitor. The inventors continued the inventors' characterization of J54. The other synthesized compounds did not show much inhibition even though several are PTH (FIG. 22). The inventors have carried out some SAR studies and molecular modeling to explain why, and for simplicity, the inventors show below a comparison between THD and J54.

Figure 9B:
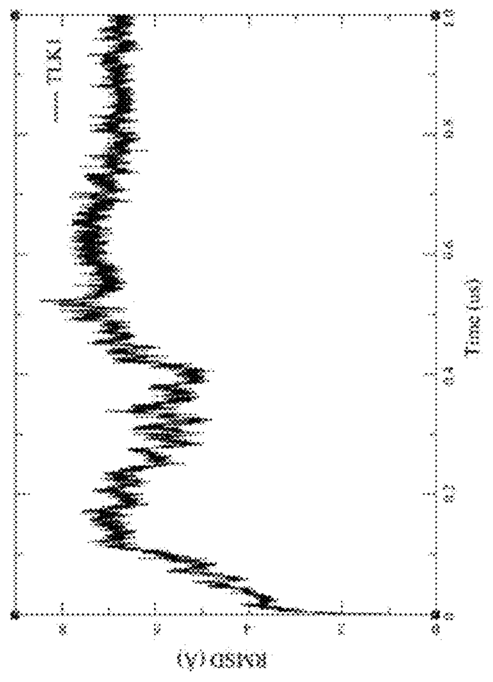
Figure 9C:
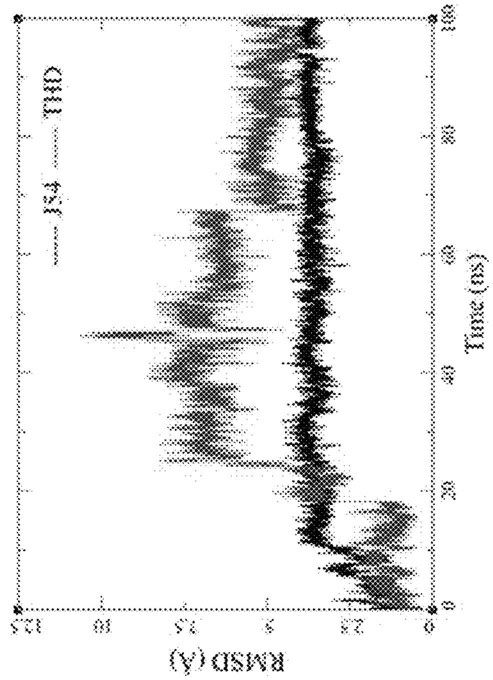
Figure 9A:
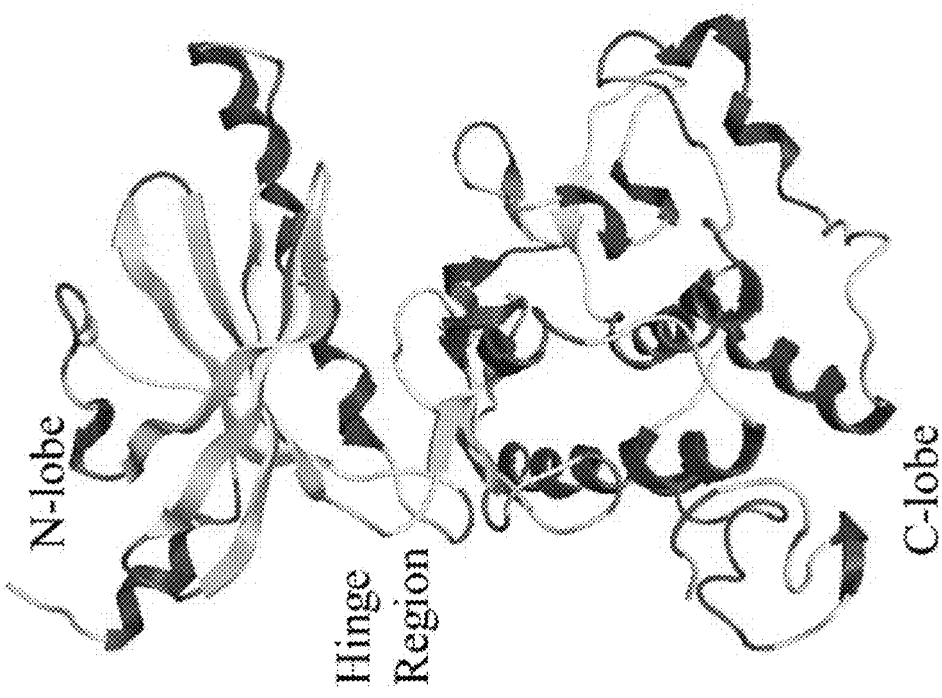
Figure 10A:
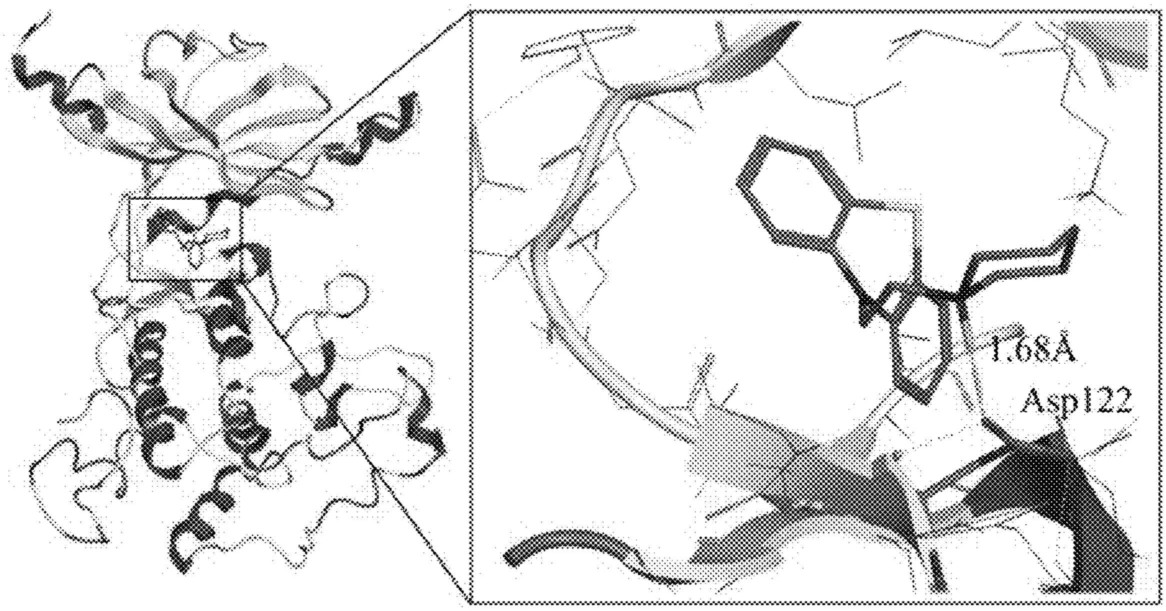
FIGS. 10A and 10B show molecular docking and molecular dynamics studies of J54 and THD with TLK1, with FIG. 10A showing interactions of J54 with the active site of TLK1.
Figure 10B:
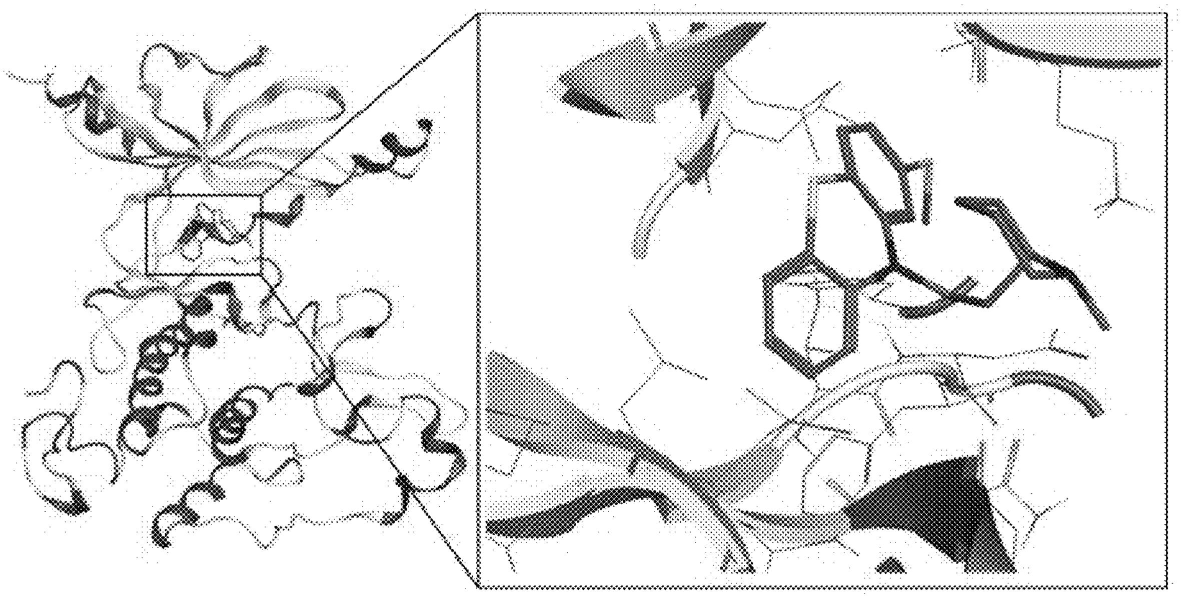
Figure 14:
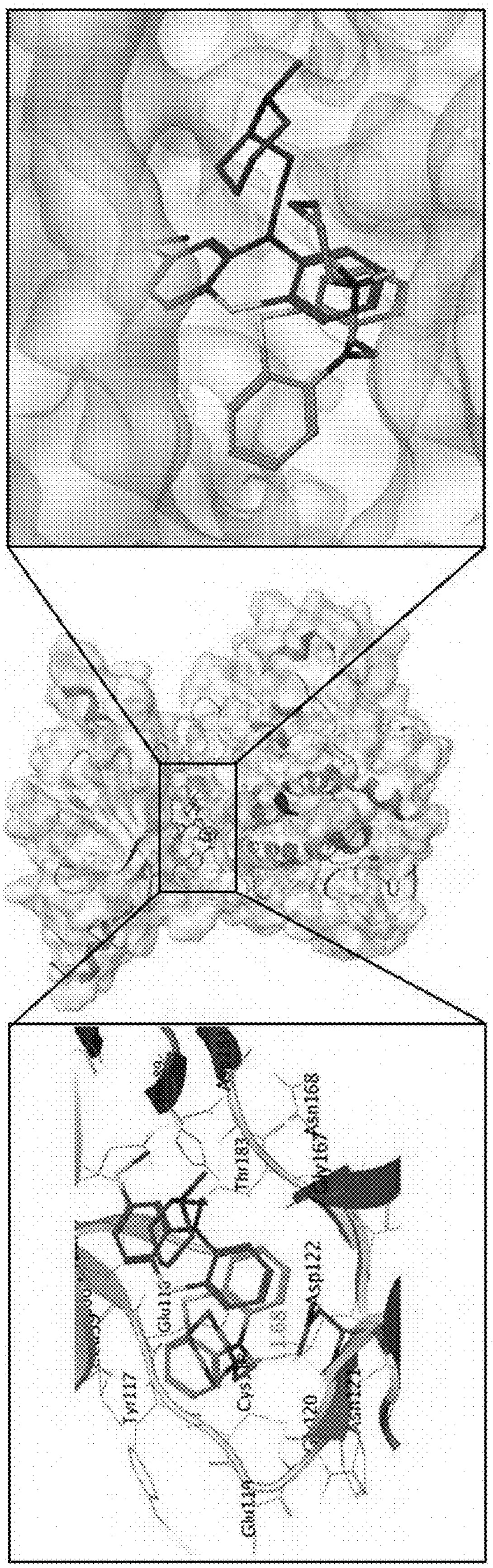
FIG. 14 shows an overlay of J54 and THD ligands within the active site of TLK1, from various viewpoints.
Figure 16A:
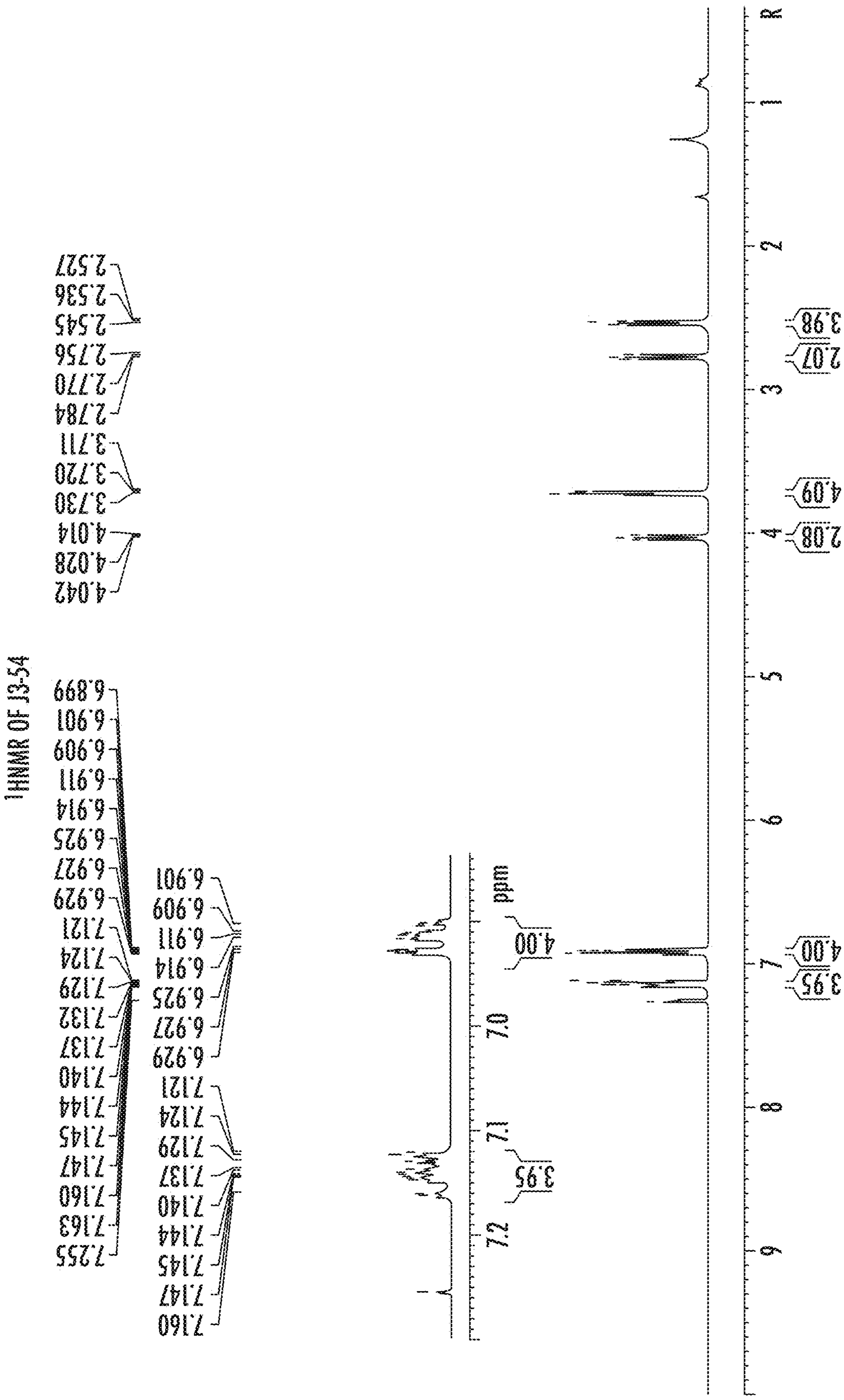
FIGS. 16A-16C show an $H^3$NMR and MS of J54.
Figure 16B:
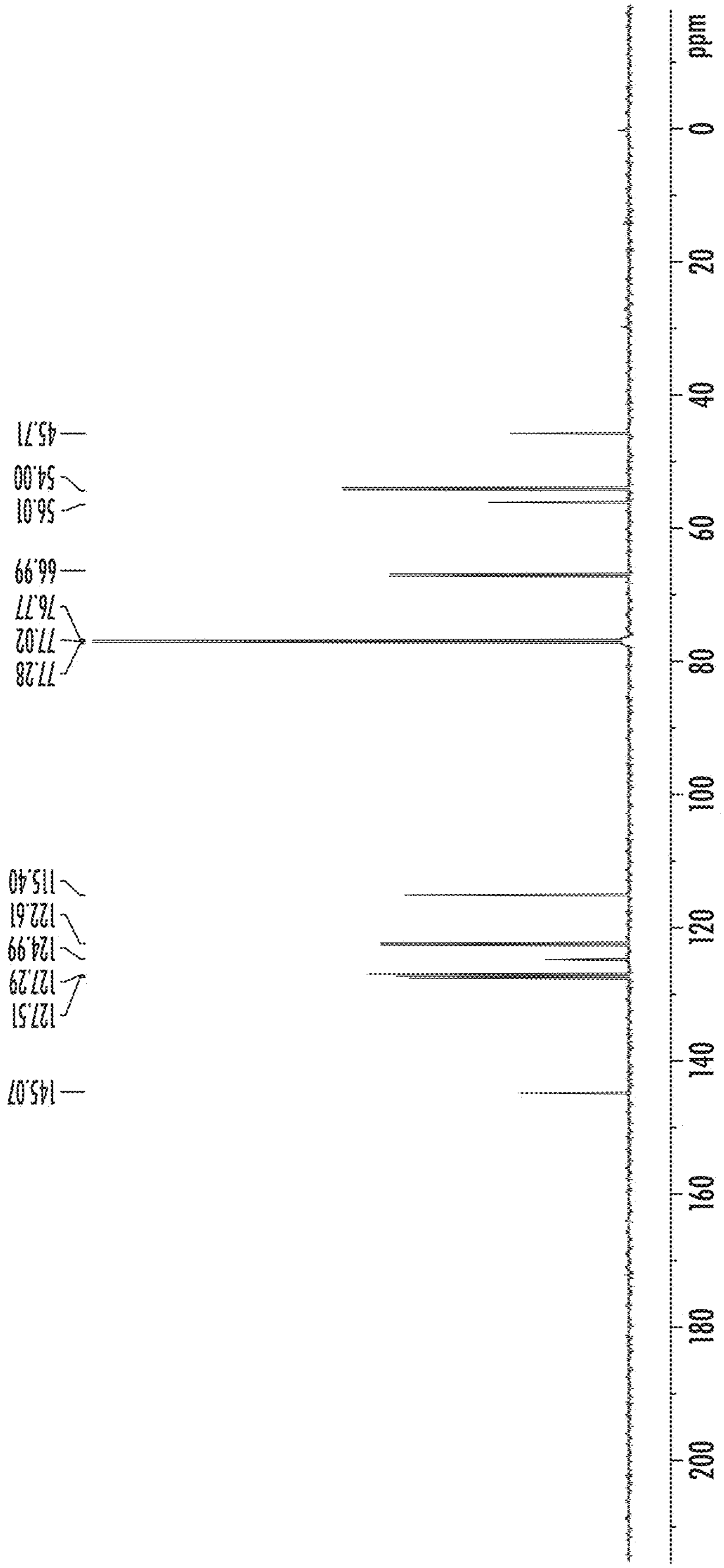
Figure 16C:
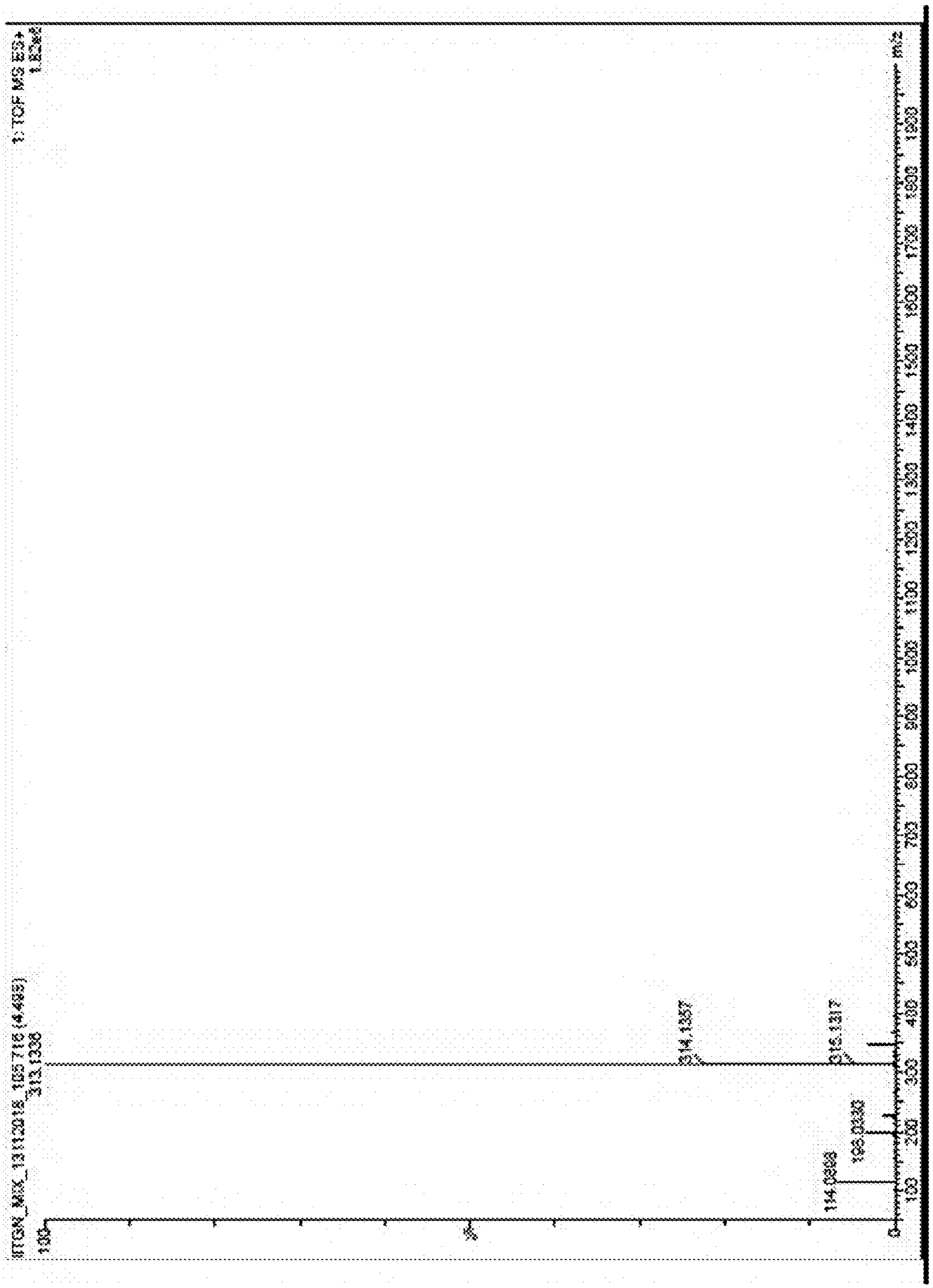
Figure 17A:
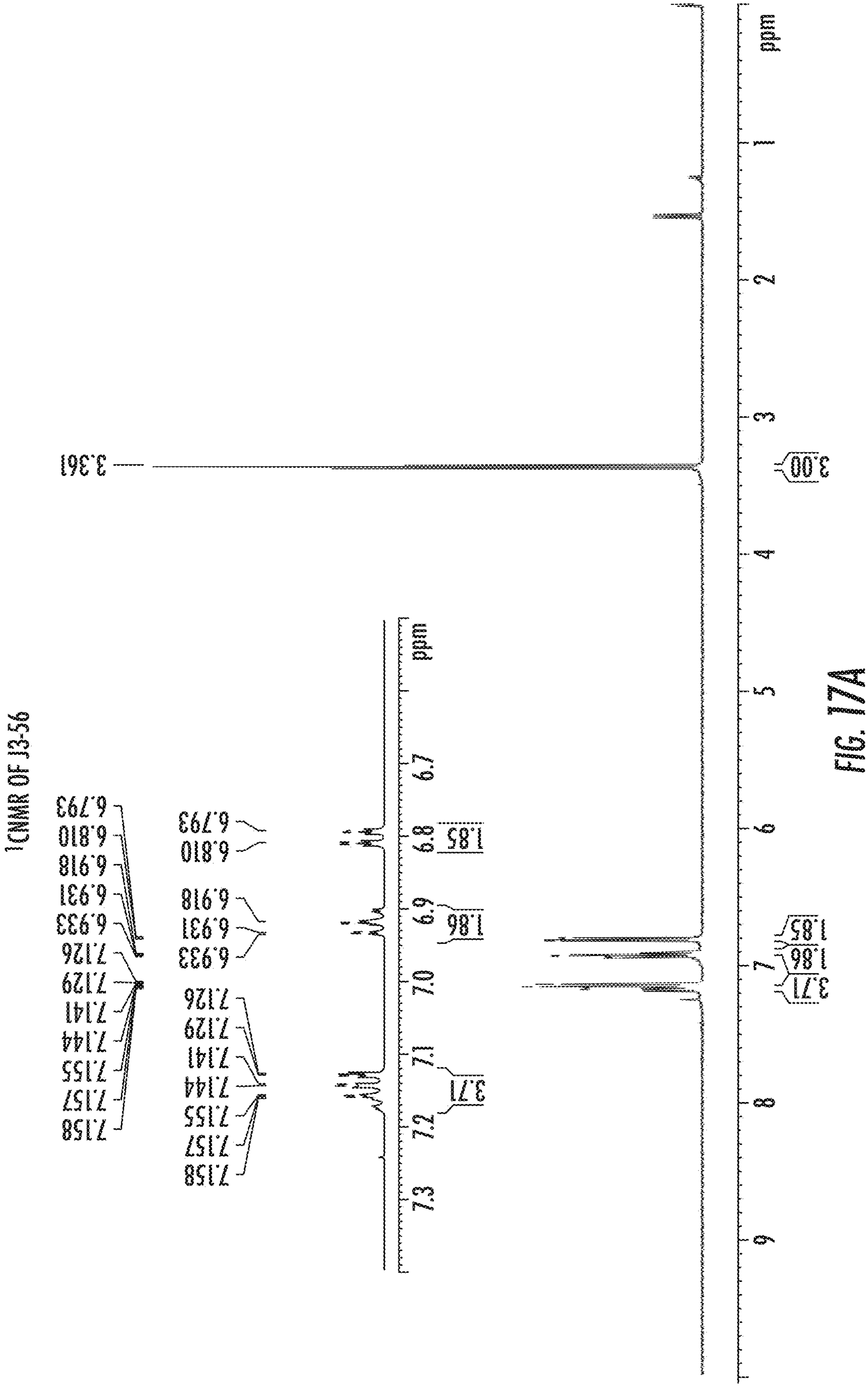
FIGS. 17A-17C show an $H^3$NMR and MS of J3-56.
Figure 17B:
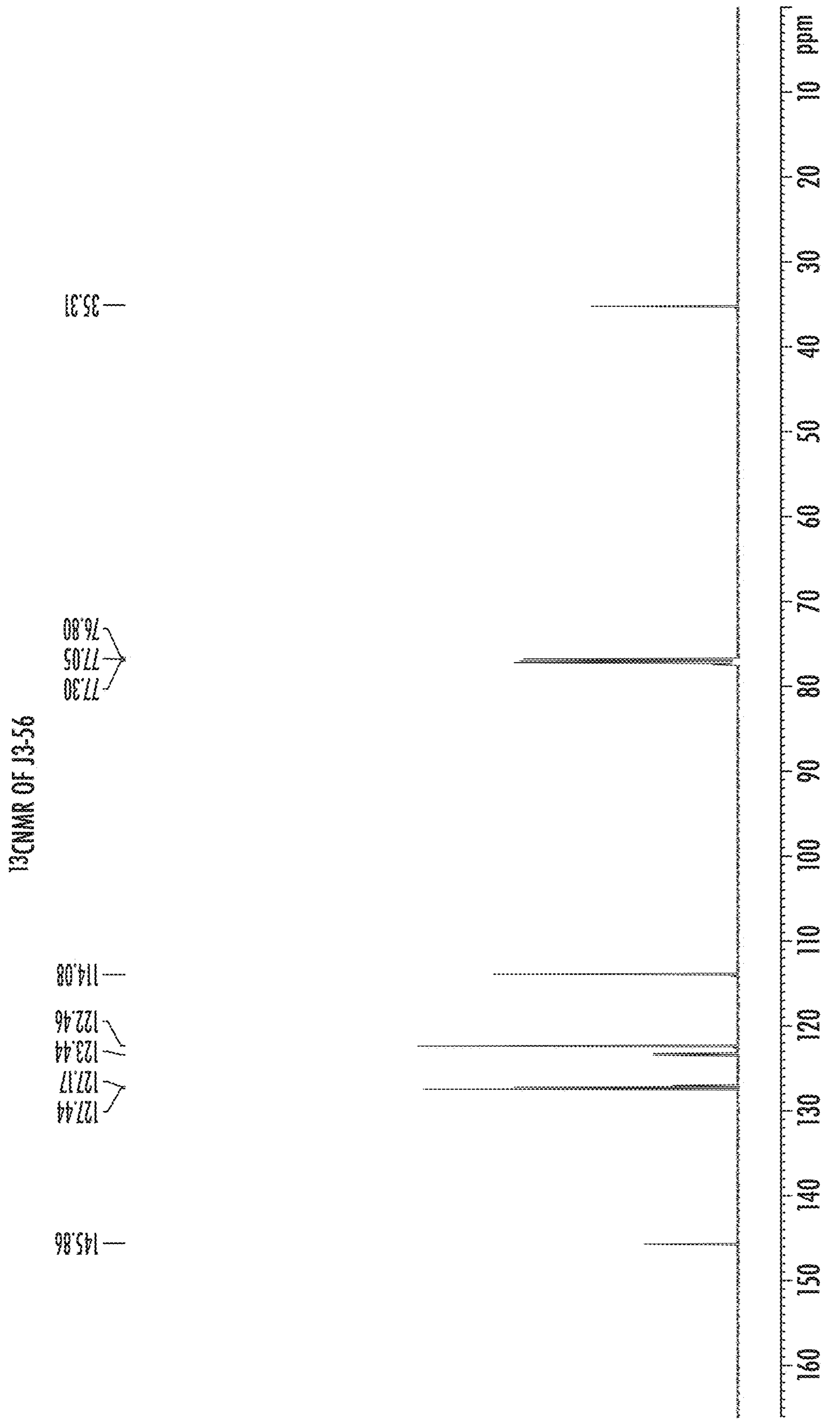
Figure 17C:
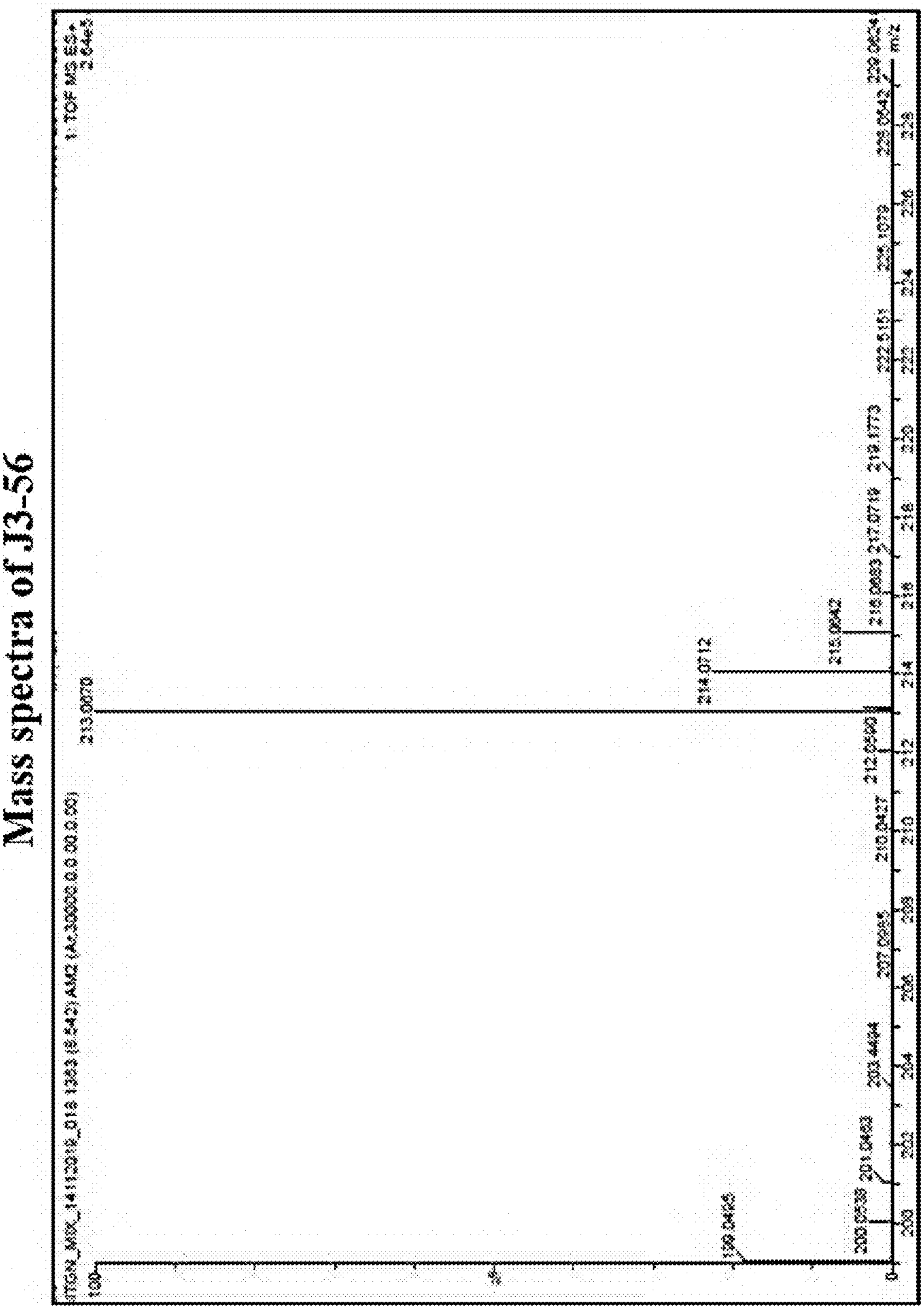

In-silico modeling studies of TLK1B with docked J54 or THD. A model of the TLK1B kinase domain was constructed by homology modeling using the ROBETTA de novo protein structure prediction server. (see Methods in Appendix). The model was further refined by a 1 μs molecular dynamics (MD). The backbone RMSD of the structure stabilized after 100 ns although was subject to periodic RMSD shifts until 600 ns (FIG. 2A). Compounds J54 and THD were docked into the ATP site of the final MD-refined model (FIGS. 9B and 9C). In the docked pose of compound J54, good interactions with the hinge region residues of TLK1 were exhibited; the morpholino head forms hydrogen bonds with Asp122, with a distance of 1.68 Å from the Asp122 carboxylate O□ to the ligand NH group (FIGS. 10A and 9D). A 100 ns MD simulation of this TLK1-J54 complex indicated the pose is stable, further evident from a favorable total binding free energy $\Delta G_{bind}$=−39.7 kcal/mol, computed by the MM/GBSA method (FIG. 9D). THD was docked in the same TLK1 pocket but did not form hydrogen bonds with the protein (FIG. 14). MD of the complex indicated a markedly higher RMSD in ligand atoms, with greater fluctuation, than for the J45 complex (FIG. 9C); the free energy of binding is 9.9 kcal/mol weaker (FIG. 9D). The inventors note that this in part could arise from the methylthio group of THD which prevents it from entering the hinge region to the same extent as J54 (FIG. 14).

Figure 11A:
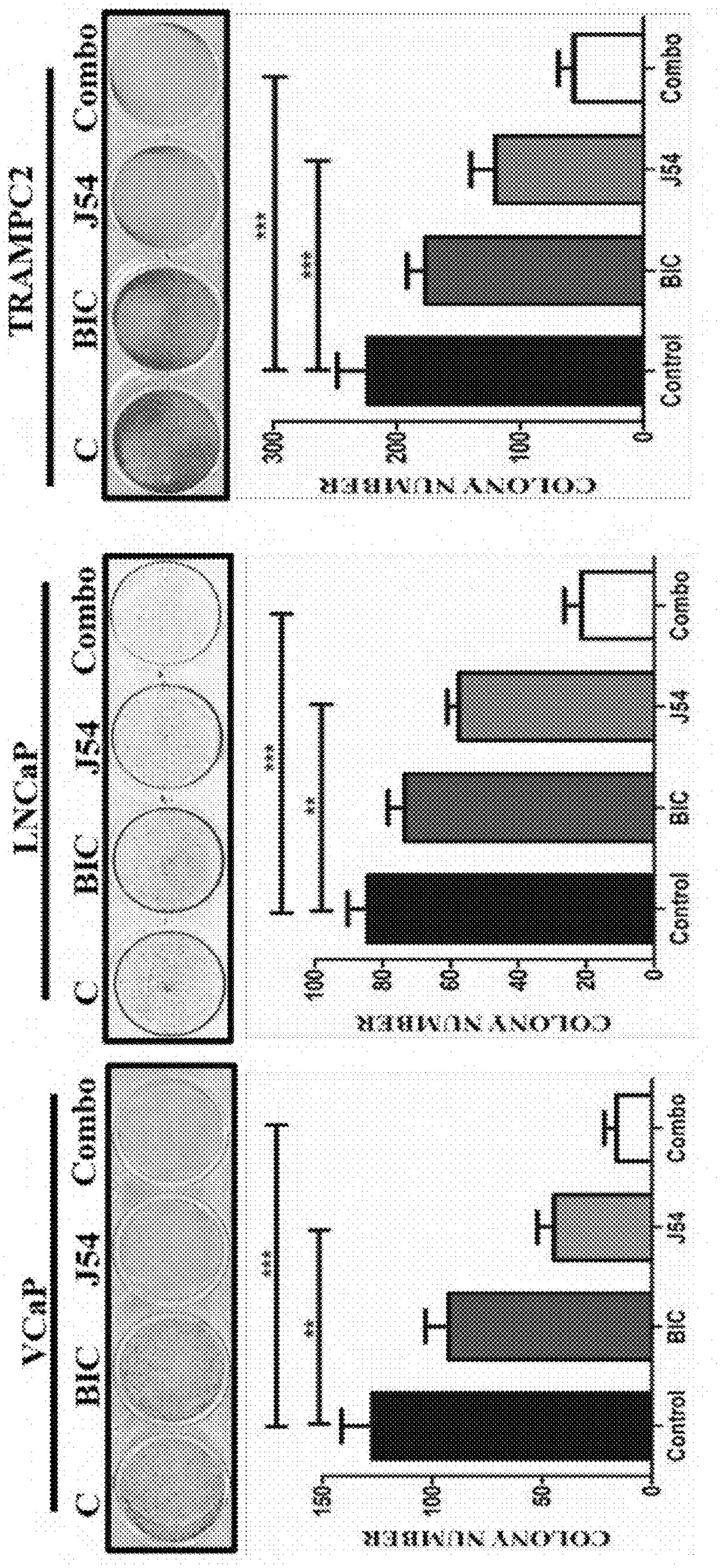
FIGS. 11A-11E shows that J54 in combination with an anti-androgen (Bicalutamide) induces apoptosis in AS PCa cells. All experiments were conducted in triplicates.
Figure 11B:
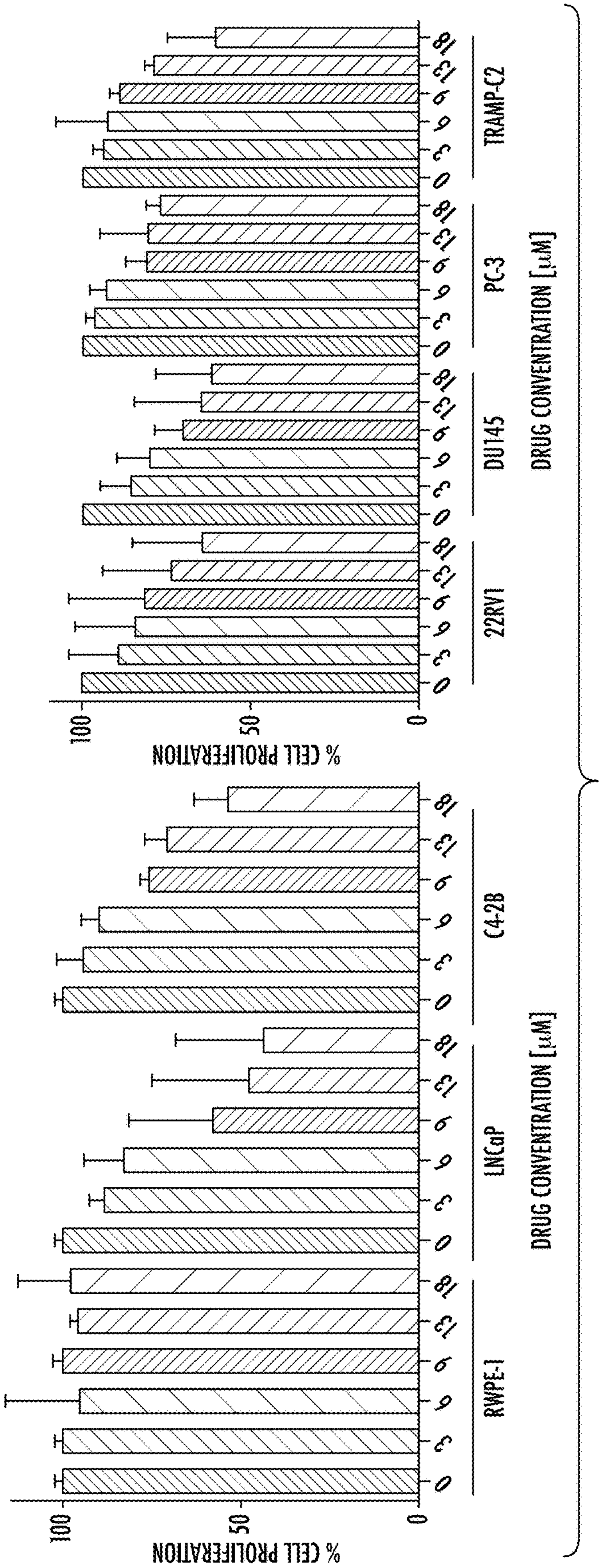
Figure 11C:
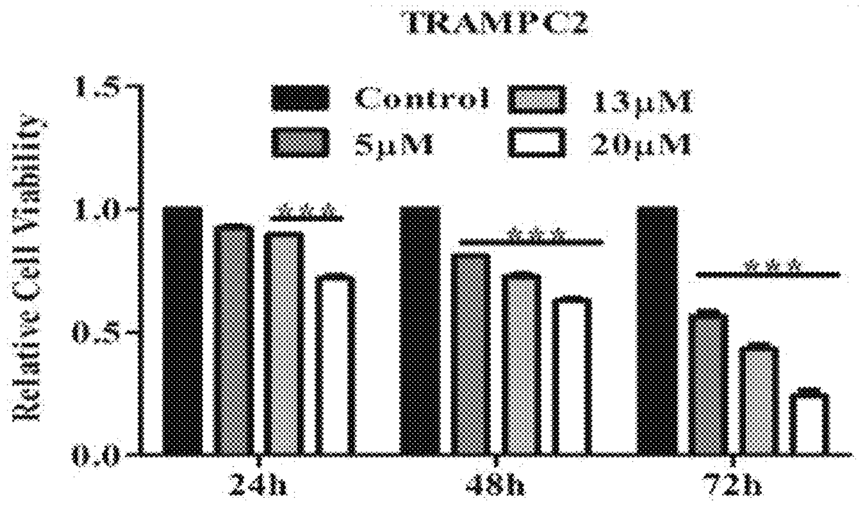
Figure 11D:
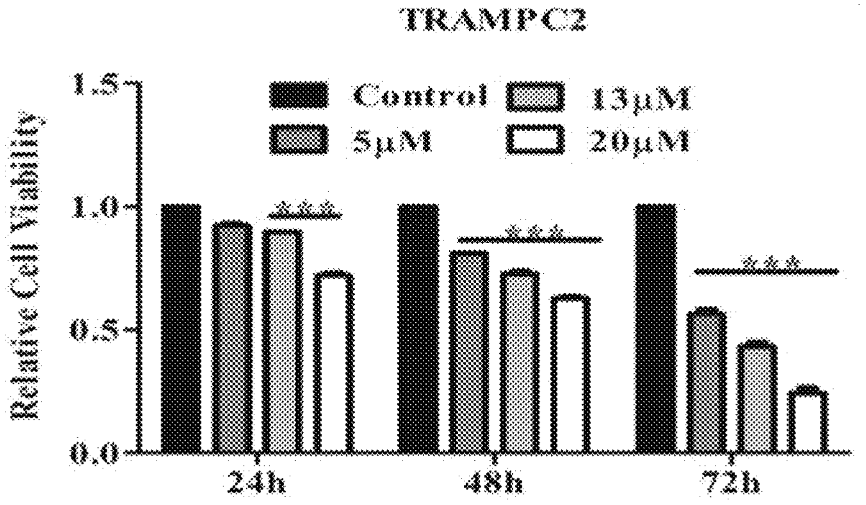
Figure 11E:
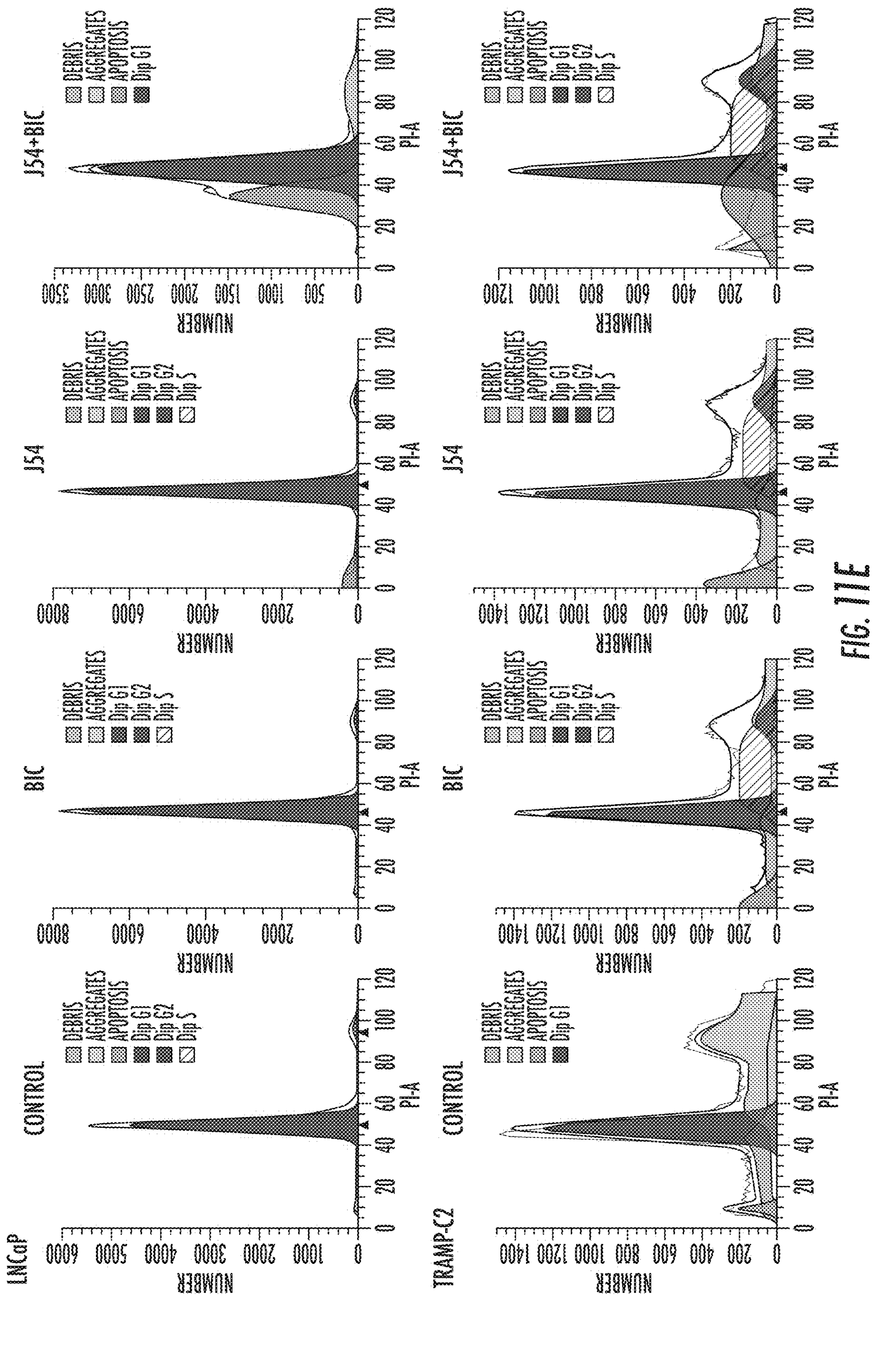

J54 in combination with anti-androgen (Bicalutamide) induces apoptosis in AS PCa cells. The inventors experimentally demonstrated that THD has some growth inhibitory effects for several PCa cells lines, either androgen sensitive (AS) or insensitive (A1). The inventors thus tested the same panel of cells in androgen containing medium (FBS) by proliferation assays. The effect was a weak dose-dependent inhibition with maximal efficacy around 18 μM (FIG. 11B). Note however, that RWPE1 (normal prostate)

cell line was insensitive to J54, suggesting that J54 may be a more targeted anti-cancer agent, or it is possible that the TLK1>Nek1 axis remains critical even for CRPC cells. In contrast to these mild effects, combination treatment of the AS cell lines—LNCaP, VCaP and TRAMP-C2—with bicalutamide (BIC) and J54 resulted in 4-5-fold suppression in colony formation (FIG. 11A, p=0.001). Note that VCaP cells were 60% inhibited by J54 alone, consistent with their elevated replication stress-driven DDR and checkpoint activation (FIG. 12C), which when suppressed with J54 could lead to apoptosis. Clonogenic assays are unable to distinguish the effects of a DNA damaging agent, which can result in either an impaired or delayed resumption of growth (cell division) or loss of viability due to increased killing of the initial population. The inventors thus measured in LNCaP and TRAMP-C2 cells the early change in cell number (MTT assay) over 72 h with J54 alone. The results indicated an actual loss in cell counts in relation to the dose (FIGS. 11C and 11D, p=0.001). These results reinforced the inventors' main thesis that inhibiting the TLK1>Nek1 axis is mostly an effective regimen for AS cells in combination with anti-androgens. Indeed, cell cycle analysis of LNCaP and TRAMP-C2 cells treated with BIC, J54, or combination for 24 h showed a strong increase in the fraction of apoptotic cells only in the combination group (FIG. 11E). Note also that, unlike cells treated with BIC that display an accumulation of cells at G1/S and reduction of the S and G2 populations, cells treated with both BIC and J54 do not display the arrest (particularly no loss of the G2 cells), i.e., bypass of the G1 checkpoint and consequent apoptosis (see FIG. 24).

Figure 12B:
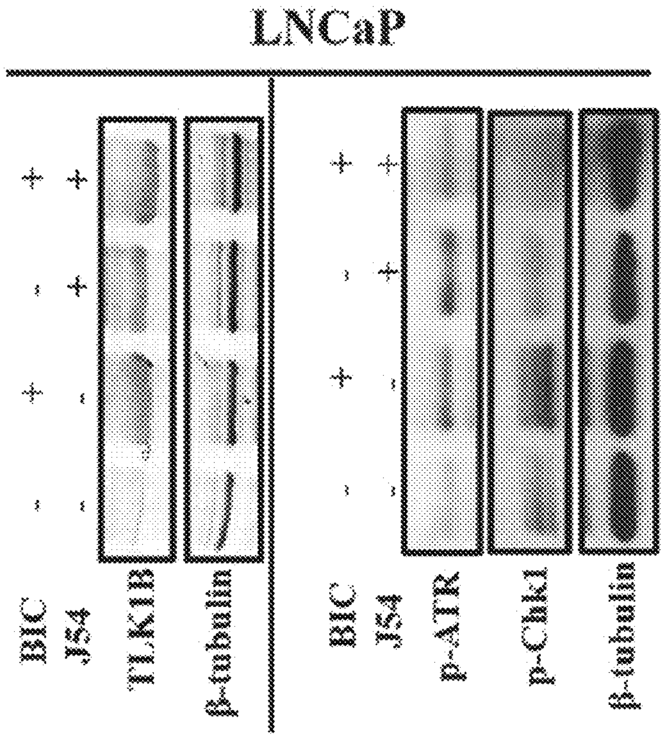
FIGS. 12A-12D are Western Blots of cell cycle and apoptotic indicators, which show that J54 in combination with Bicalutamide suppresses the checkpoint activation markers and induces apoptotic markers. LNCaP (FIG. 12A-12B), VCaP (FIG. 12C), and TRAMP-C2 (FIG. 12D) cells from the four treatment groups as indicated were analyzed by WB for several indicators of DNA damage/apoptosis and mediators of cell cycle arrest. Representative analysis of two independent experiments for each cell line are shown.
Figure 12A:
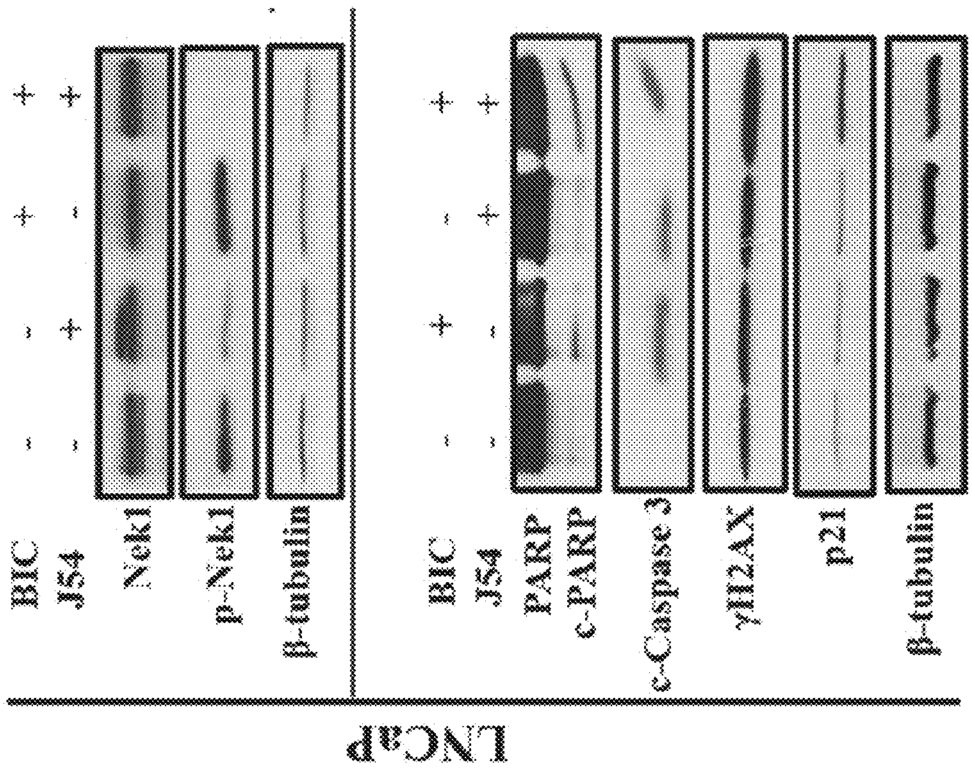
Figure 12D:
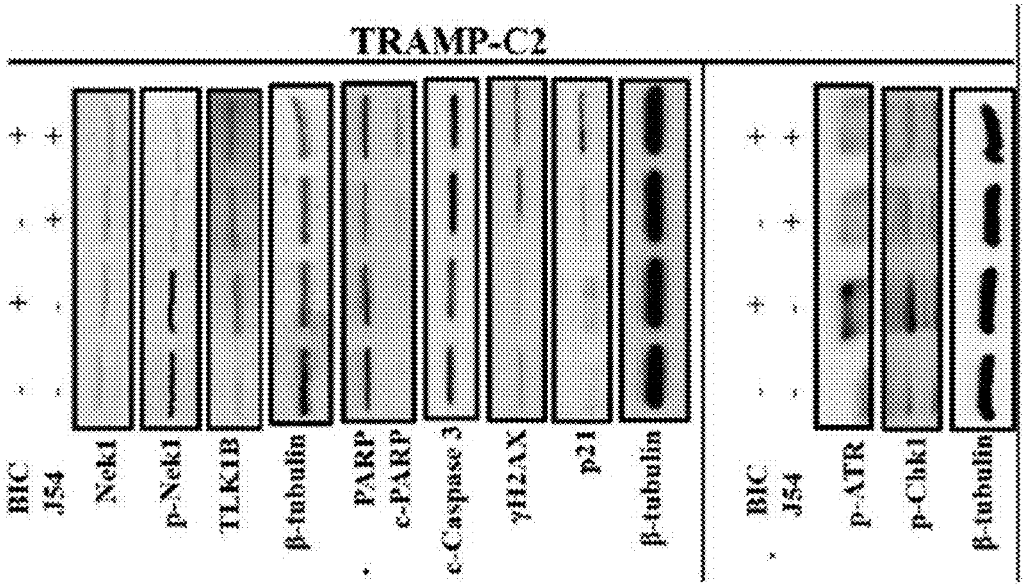
Figure 12C:
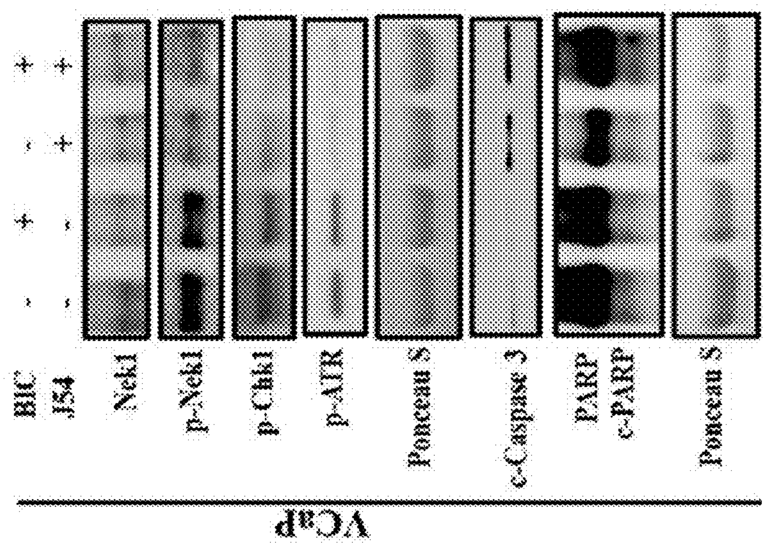
Figure 20A:
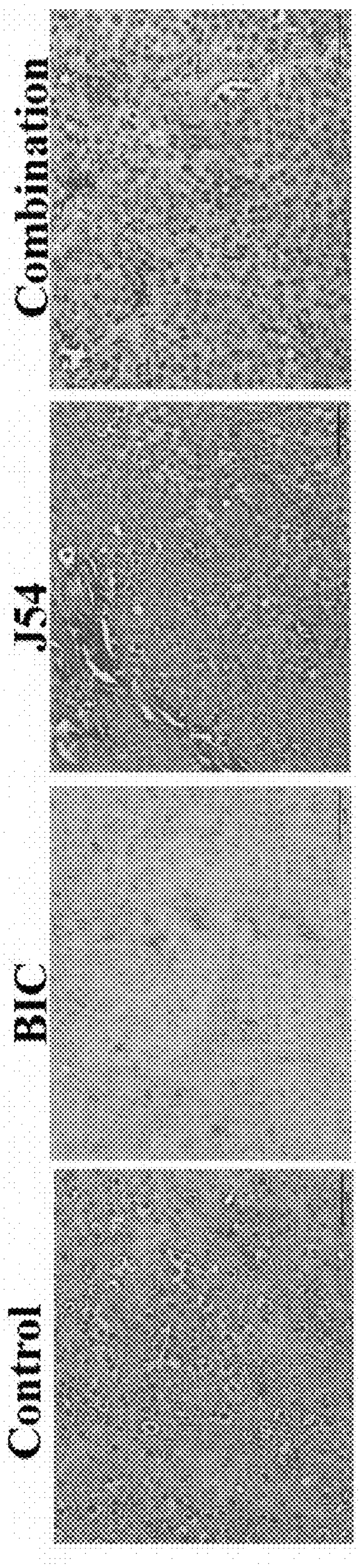
FIG. 20A shows H&E stain of representative LNCaP tumors (from 3 mice)
Figure 20B:
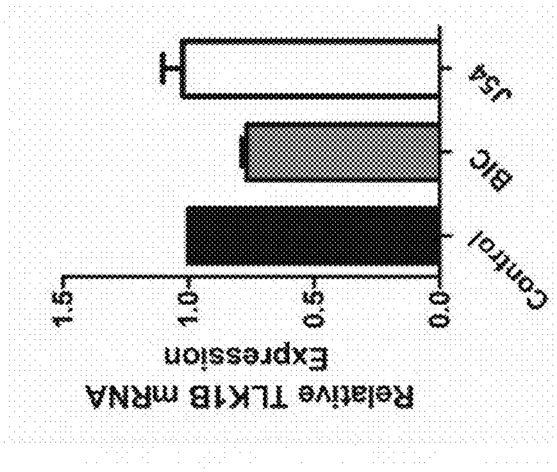
FIG. 20B shows qRT-PCR quantitation of TLK1B mRNA expression (from 3 mice per group in triplicate reactions).
Figure 21:
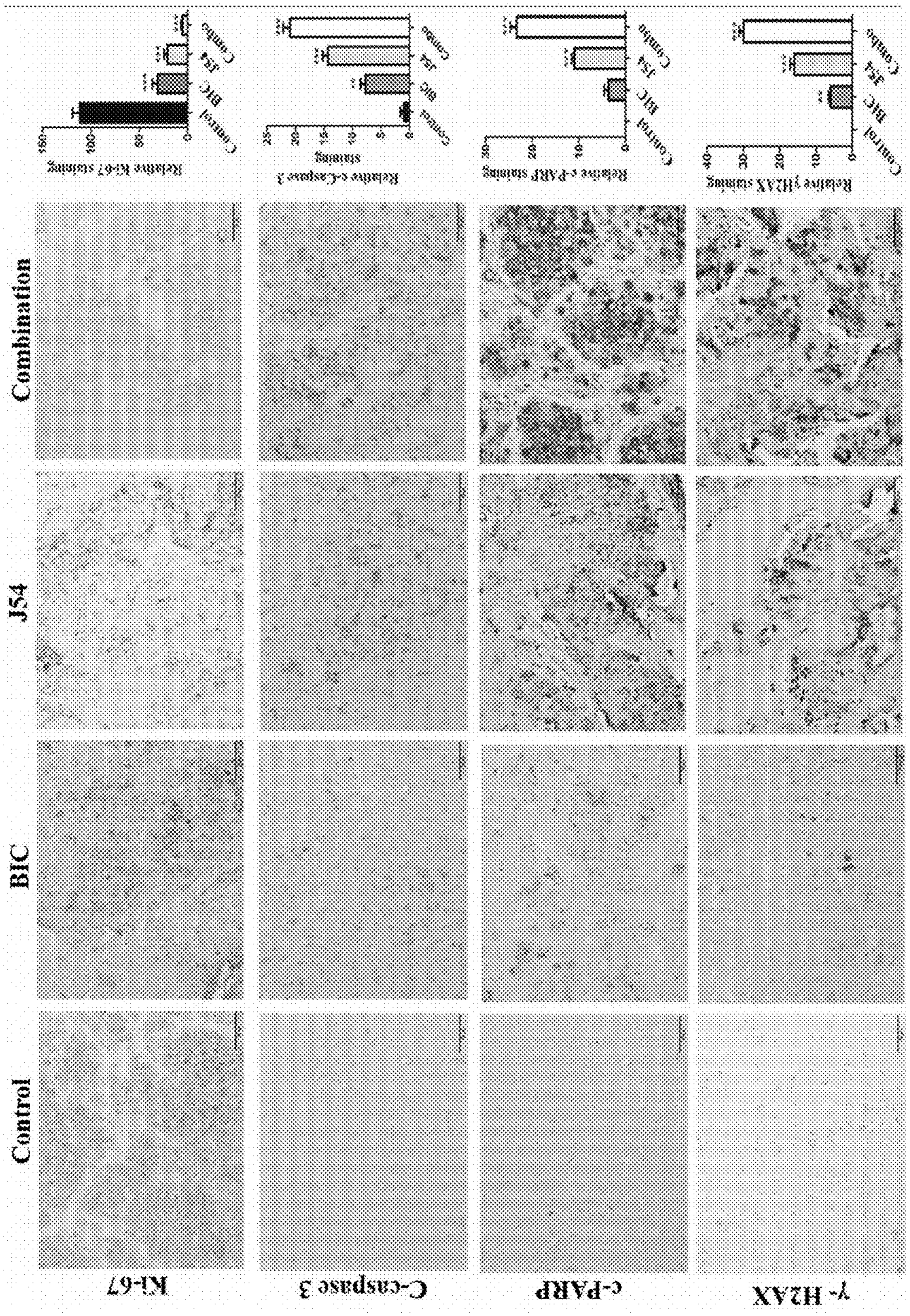
FIG. 21 shows IHC analysis of markers of proliferation (Ki67), apoptosis (Cleaved PARP and Caspase 3), and presence of γH2AX (an indicator of DSBs—Quantitation of the stained sections is shown on the side. Representative section from 3 mice per group are shown.

J54 with Bicalutamide suppresses the checkpoint markers and induces apoptotic markers. LNCaP, VCaP, and TRAMP-C2 are the main examples of established PCa cell lines that are initially AS, but when maintained in ADT condition, recapitulate the conversion to A1 growth observed in patients, and start growing again. In the initial phase of ADT, they arrest cell division, primarily at the G1/S transition, and become quiescent, which is a protective effect from undergoing replication forks collapse upon inhibition of the licensing function of the AR. Since inhibition of the TLK1B>Nek1>ATR>Chk1 axis with THD results in bypass of the DDR and apoptosis, the inventors have tested the same process with J54. First, the inventors confirmed that J54 (with or without BIC) causes a reduction in the p-Nek1-T141, the site of activation that is phosphorylated by TLK1, in all 3 AS cell lines (FIGS. 12A-12D). The inventors were also able to reproduce that the expression of TLK1B was induced in LNCaP and TRAMP-C2 following the addition of BIC. The inventors experimentally showed that this is due to a mRNA translational effect caused by the compensatory increase in mTOR activity following ADT and suppression of AR signaling—note there was no change in the TLK1B mRNA with BIC (FIG. 20B). Treatment with BIC resulted in activation of the DDR, shown as an increase in p-ATR and p-Chk1 in LNCaP and TRAMP-C2. In contrast, suppression of p-Nek1 and its activity with J54 resulted in inhibition of the BIC-induced DDR activation, as manifested by a decrease in p-ATR and p-Chk1 (FIGS. 12A-12D). J54 alone caused a modest increase in p-ATR but not in Chk1 in LNCaP and TRAMP-C2, as was previously observed by the inventors with THD, possibly due to a mild genotoxic effect. The VCaP cells were a little different because even without any BIC, p-ATR and p-Chk1 were already elevated. This has been observed before and attributed to a constitutive DDR activation due to the TMPRSS2-ERG fusion in these cells. Nonetheless, the addition of J54 to VCaP cells resulted in reduction of p-Nek1 and p-Chk1, indicating that it can suppress the DDR checkpoint, whether activated constitutively or after BIC treatment (FIG. 12C). As the inventors previously demonstrated for inhibition of TLK1 with THD, bypass of the BIC-induced checkpoint results in replication forks collapse, generation of DSBs (indicated by the presence of γH2AX), and apoptosis (indicated by increased cleaved caspase 3 and PARP—FIGS. 12A-12D). Likewise, in BIC+J54 treated cells there was an increase in P21 expression: an indicator of the emergency activation of the P53>p21 pathway, and an effect previously observed for BIC+THD.

Figure 13A:
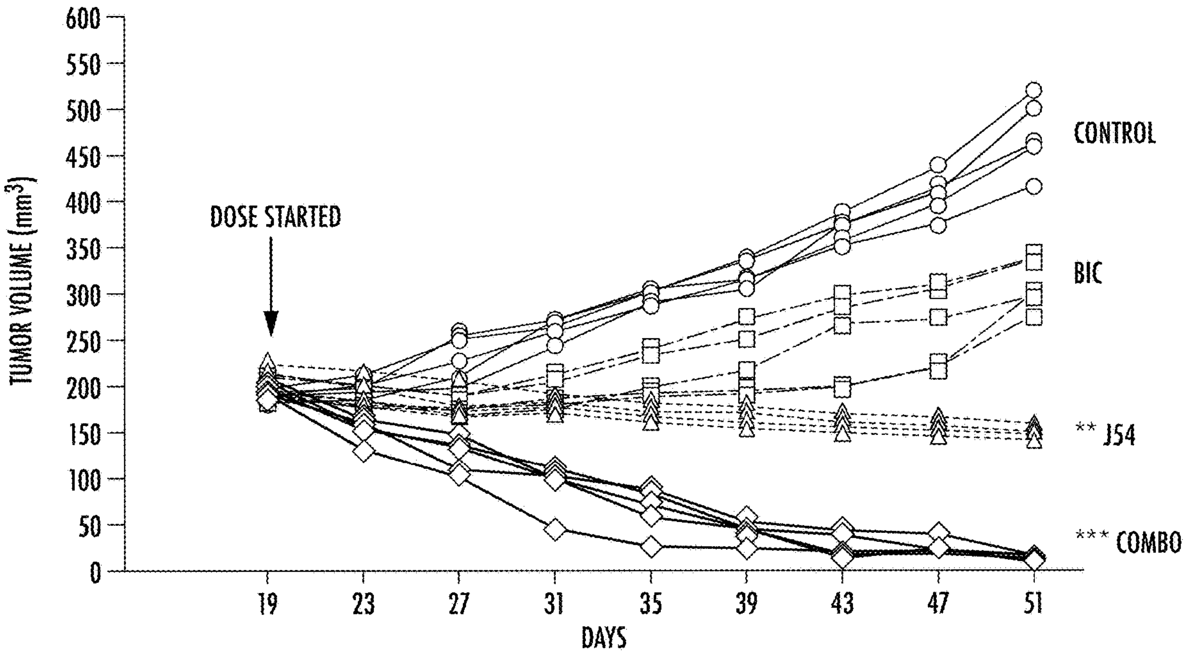
FIGS. 13A-13D show that the combination of bicalutamide and J54 suppresses growth of LNCaP xenografts.
Figure 13B:
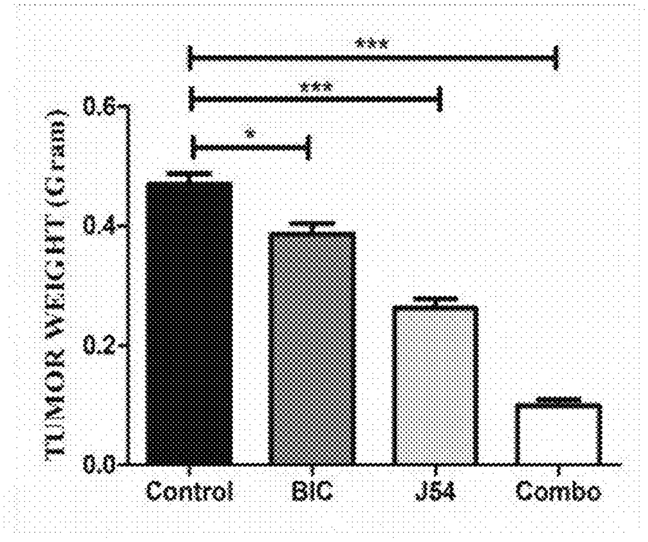
Figure 13C:
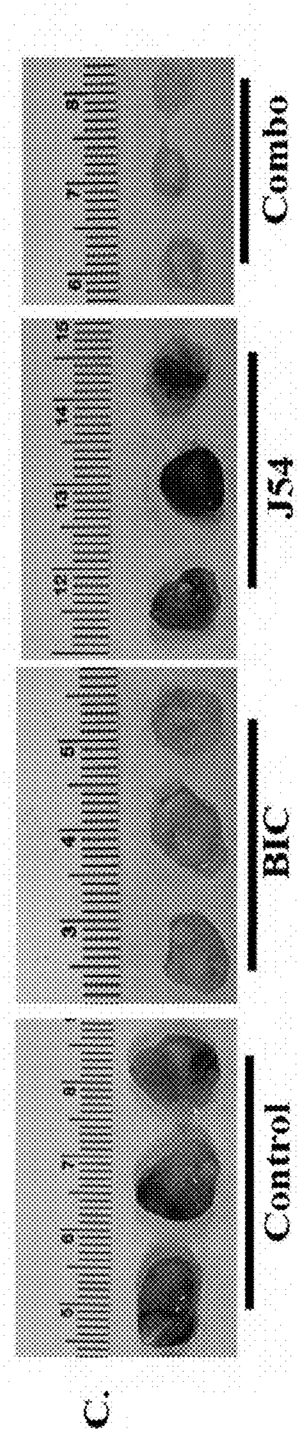
Figure 13D:
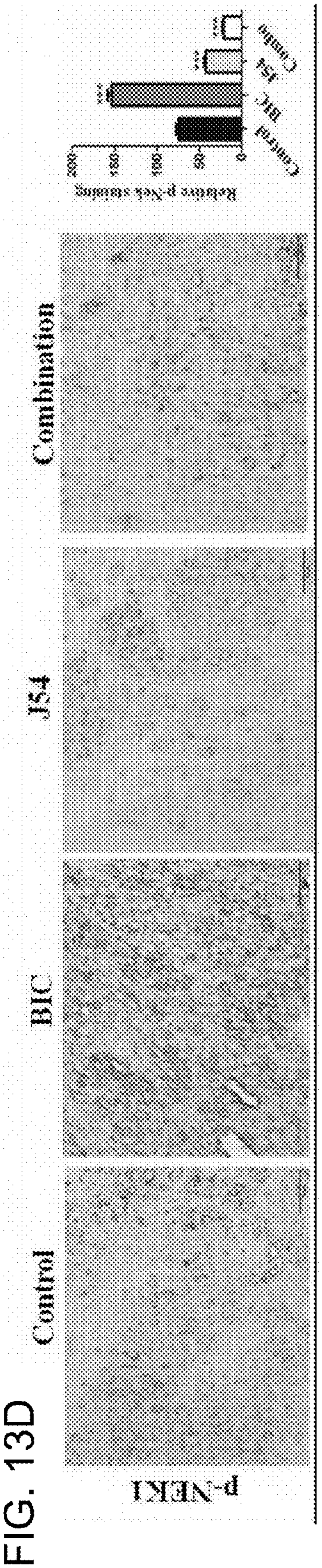
Figure 18A:
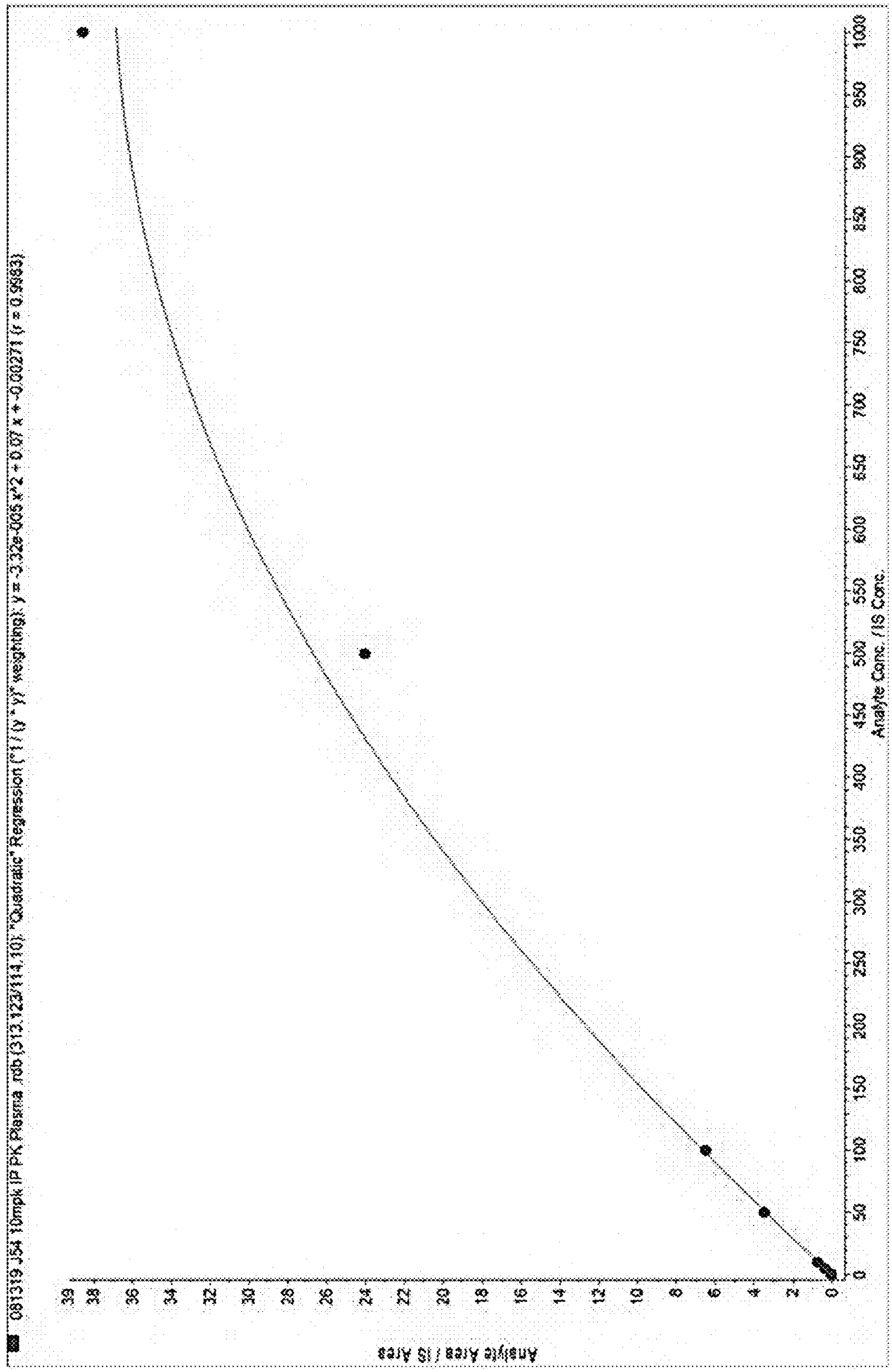
FIGS. 18A-18C show pharmacokinetics plasma distribution of J54.
Figure 18B:
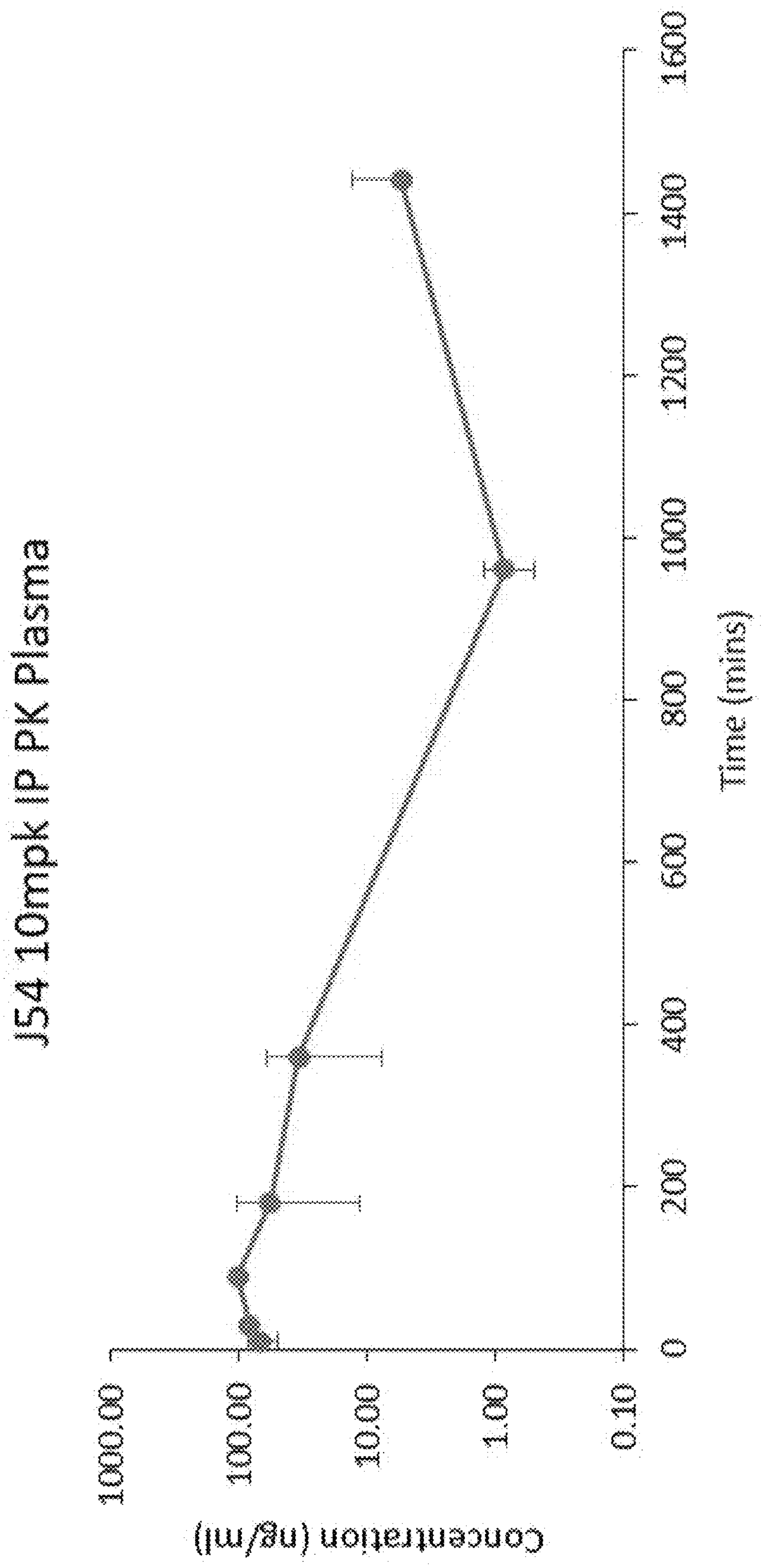
Figure 18C:
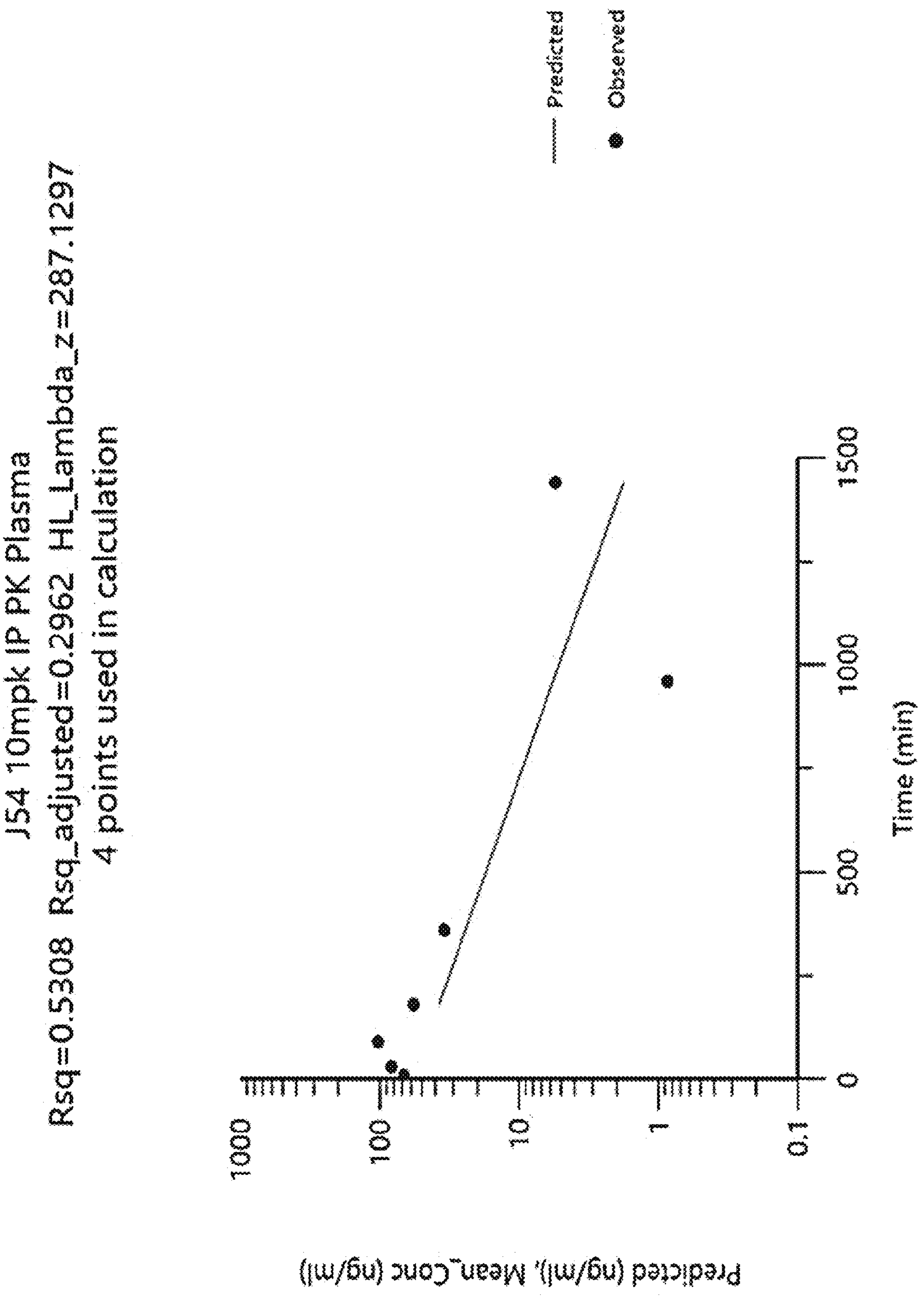

Bicalutamide with J54 suppresses growth of LNCaP xenografts via suppression of the TLK1B>pNek1 DDR pathway and promotes apoptosis. The inventors sought to establish if the addition of J54 could suppress the resurgence of tumor growth of LNCaP xenografts and their latter conversion to CRPC. Following formation of sizeable tumors (~200 mm3), castration or anti-androgens arrest the progression of LNCaP xenografts for some time (2-3 weeks), while subsequently the tumors start growing again at an accelerated rate which is refractory to ADT (A1). Therefore, the inventors injected LNCaP cells in matrigel in both flanks of NOD-SCID mice, and then randomly assigned them to four treatment groups (n=5 per group×2 independent experiments), as shown in FIGS. 13A-13C. The control group showed progressive exponential growth, and so did the BIC group after a 12-day lag following the beginning of BIC administration. Interestingly, treatment with J54 alone showed significant suppression of tumor growth (p=0.01) and tumor weight (p=0.001); whereas the combination (BIC+J54) resulted in complete suppression of tumor growth and weight (p-0.001) and actual regression of the tumors compared to the starting size FIGS. 13A-13C. An IHC analysis of the available excised tumors showed that the phosphorylation of Nek1-T141 was increased in BIC-treated group (FIG. 13D, p=0.001), consistent with a corresponding increase in TLK1B expression; it was suppressed by concomitant administration of J54 (p=0.001), which is expected to result in bypass of the DDR checkpoint and increased apoptosis and corresponding markers. In fact, the combination treatment showed a strong increase in staining for cleaved PARP and Caspase 3, and γH2AX (a marker of DNA damage, p=0.001—FIG. 21). Tumors in the combination also showed a reduction in the number of proliferative cells by Ki67 staining (p=0.001), although this was lower also for the groups singly treated with BIC and J54 (FIG. 21—Note that these tumors were isolated at day 30 when they were still sizeable). The inventors should also point out that the inventors treated the mice with J54 only bi-weekly due to the favorable pharmacokinetics, where maximal plasma concentration of 100 ng/ml (35 μM) were reached 2 h after IP injection and was still present at ~6 ng/ml (6 μM) after 24 h (FIG. 18A-18C).

J54 has low DR2 binding activity and behavioral effects in animal models. THD has strong antitumor effects in combination with ADT for AS-PCa according to the inventors' models. However, after ~30 years of use for schizophrenia, this drug was withdrawn for treatment due to increased risk of cardiac arrhythmia and extrapyramidal toxicity. The repurposing of PTH anti-psychotics for cancer therapy was proposed by the inventors even though their cellular targets have not been identified, as they were generally assumed by the inventors to work largely through inhibition of dopamine receptors. The inventors wondered if J54 has also anti-dopaminergic activity. The inventors thus considered the potential interaction with the D2 dopamine receptor (DR2). Compounds J54, THD and DR2 antagonist risperidone were studied by molecular docking, MD and free energy calculations, based on the risperidone/DR2 crystal structure (PDB code 6CM4). The three ligands were docked in the DR2 pocket (docking was able to reproduce the observed pose of risperidone). The three complexes were solvated and simulated via MD for 100 ns. Compound J54 binds stably in the active site of the DR2, forming a hydrogen bond with Ser159 distance of 2.24 A (FIG. 15A). THD and risperidone also complex with the DR2 via hydrogen bonds (FIGS. 15A and 15C). Interestingly, the binding free energy computed via MM/GBSA ranks J54 as the lowest affinity ligand, with a $\Delta G_{bind}$ value of −29.0 (FIG. 9D). This is followed by THD (−39.0 kcal/mol) and then risperidone (−53.4 kcal/mol). These free energy calculations suggest that J54 binds only weakly and has a lower affinity than risperidone and THD towards DR2. To verify experimentally that J54 is a weak DR2 antagonist, the inventors commissioned a competitive radioassay using 7-Hydroxy DPAT, R-(+)-[3H] as a tracer and two recombinant human dopamine receptors (D1 and D3). Positive control antagonists were included [R(+)-SCH-23390 and (±)-7-Hydroxy-2-(di-n-propylamino) tetralin ((±)-7-OH-DPAT),]. In FIG. 25, the inventors show the results obtained at effective concentrations of 100 nM for J54 compared to THD, which confirmed that J54 is a very weak antagonist for dopamine receptors. Note that in these competitive studies with recombinant receptors, the antagonist (e.g, THD) is typically active in the 10 to 100 nM range (IC50-20 nM for THD), whereas for DR2 antagonism for amelioration of psychotic conditions, circulating concentrations in plasma need to be −100 μM.

Figure 19A:
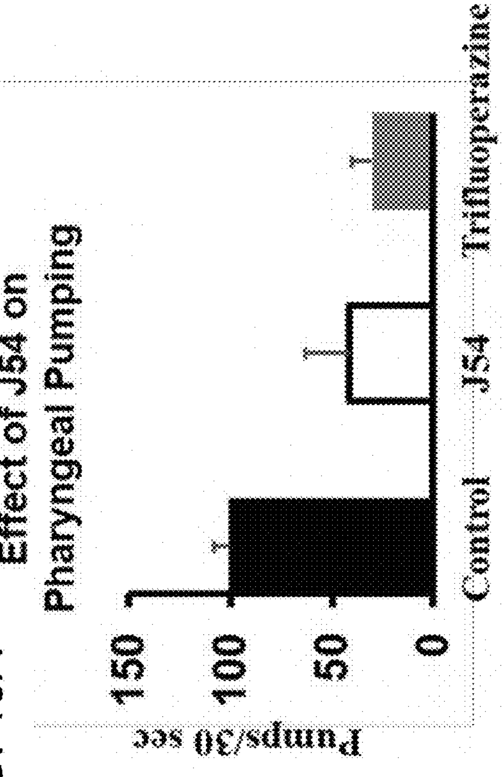
FIGS. 19A-19C show behavioral assays in *C. elegans*.
Figure 19B:
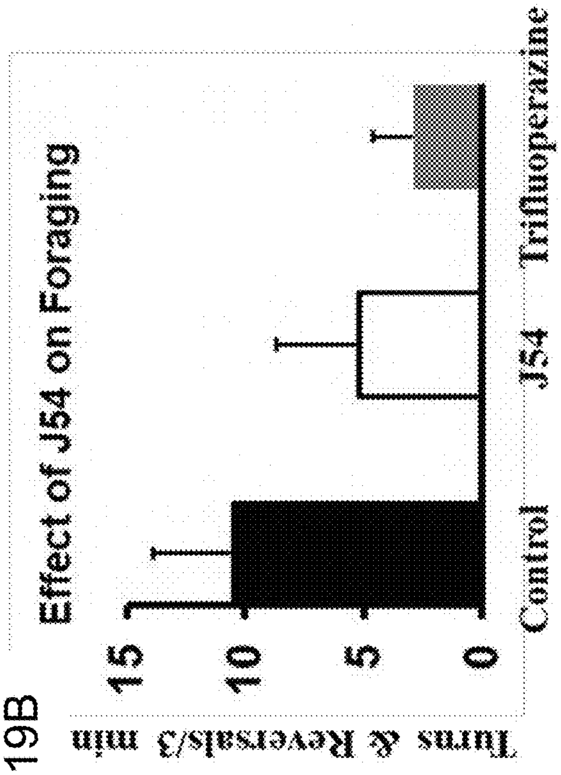
Figure 19C:
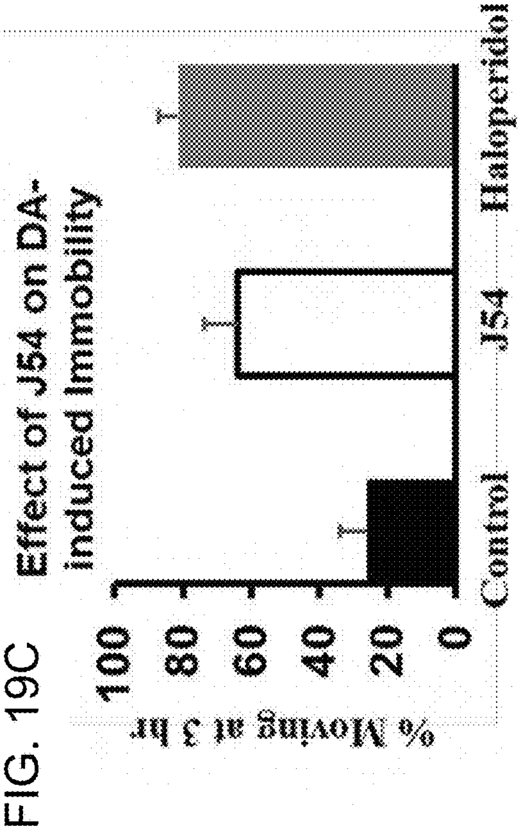

The inventors then did a general assessment of mice following injections of J54. The inventors noticed no toxicity (even after gross inspection of organs at necropsy), no decrease in body weight, and no behavioral changes (no lethargy or extrapyramidal twitches sometime observed with THD). To get a better assessment of the possible behavioral effects of J54, the inventors used *C. elegans* that has a simple but complete nervous system and has been well characterized for its responses to anti-psychotic drugs, including actions at serotonin or dopamine receptors. In three studies, J54 had much weaker behavioral effects then TFP or risperidone, attributable to DR2 activity (FIGS. 19A-19C). Note that the concentration of these drugs on agar plates need to be significantly higher than in tissue culture medium for mammalian cells because of the protective and poorly permeable cuticle in *C. elegans.*

Discussion

Some PTH were found to be potent inhibitors of TLK1, and by inference TLK2 since these proteins must homo- and hetero-dimerize for activation. Since not all PTH are good inhibitors of TLK1, it was critical to first sort out in silico which compounds best fit in modeled binding site. The inventors have now shown that J54 has higher affinity than THD by MD analysis, and hence is more potent and evidence to be more specific for TLK1. The inventors demonstrated that a TLK1 inhibitor, THD, could synergize with ADT in promoting apoptosis on AS PCa cell lines in culture and in xenografts, and in the TRAMP mouse model. This rationale was derived from the inventors' discovery that TLK1 is an upstream activator of the Nek1>Atr>Chk1 axis, in conjunction with an original result that showed that TLK1B is translationally increased following AR suppression and the established compensatory mTOR activation. Abrogation of the TLK1>Nek1>ATR axis was expected to result in bypass of the DDR checkpoint and thus promote mitotic catastrophe. This was also consistent with the known role of AR signaling in regulation of DNA repair in PCa, and synergistic killing with inhibitors of DNA repair.

While it seems clear that certain PTH anti-psychotics correlate with a decreased risk of PCa development, as a downside, the use of THD and some other PTH antipsychotics presents some risks and side effects. Therefore, the inventors have developed a second-generation TLK inhibitor that has lower affinity for the DR2. The potent dopamine antagonist activity of some PTH antipsychotics has been blamed for some of the lethargic and extrapyramidal effects, as well as for the cardiac arrhythmia. In silico, J54 showed much weaker binding to the DR2 than THD or risperidone, and it appeared to have little adverse behavioral effects in mice and worms.

In this work, several PCa cell lines were studied for growth inhibition by J54, and particularly the AS cell lines, LNCaP, VCaP, and TRAMP-C2, were sensitive to apoptosis when combined with an anti-androgen (BIC). The LNCaP model was also tested in xenografts and demonstrated remarkable tumor regression. In conclusion, the inventors suggest the use of J54 as adjuvant therapy for PCa in conjunction with anti-androgens, as a safer and more potent inhibitor of this DDR axis, which the inventors believe is commonly activated during the initial phase of PCa cells' adaptation to ADT.

Conclusions

The regulation of the DDR by TLK1 through the Nek1>ATR>Chk1 axis, and even more importantly its upregulation after ADT is a very novel finding in the field of PCa research and therapy.

While a very large amount of work in PCa therapy has been devoted to the search for better anti-androgens, that is not the case for work devoted to combining ADT with targeting the known role of the AR in controlling the DDR. The inventors' novel approach, which while counter-current to the established views of standard of care for advanced PCa, is to abrogate the ADT-induced DDR checkpoint and cell cycle arrest, thereby forcing apoptosis of PCa cells still responsive to ADT.

While it seems clear that certain PTH anti-psychotics correlate with a decreased risk of PCa development, the use of THD and some other PTH anti-psychotics presents some risks and side effects. In particular an increased risk for cardiac arrhythmia as a result of their anti-dopaminergic activity and inhibition of hERG channels could impede repositioning of some of these PTH for the treatment of PCa due to potential concerns by regulatory agencies. J54 was designed and tested to be a weaker inhibitor of DR2, and the inventors in fact noticed it had no apparent toxicity in mice, with no extrapyramidal twitches or altered breathing after administration, and relatively weak anti-dopaminergic effects in *C. elegans*. Therefore, it is a bona fide, specific inhibitor of TLK1, and not the DR2, with superior efficacy and better side effects profile.

Pharmaceutical Compositions

The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are known. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The methods described herein can include the administration of a therapeutic, or prodrugs or pharmaceutical compositions thereof, or other therapeutic agents. Exemplary therapeutics include those that inhibit TLK1B (including of Thioridazine (THD), Perphenazine (PPH), Trifloroperazine (TFP), and Promazine (PMZ), J54, and J56) in combination with those that are antiandrogenic (including bicalutamide, aminoglutethimide, ketoconazole, abiraterone acetate, enzalutamide, and apalutamide).

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredients (TLK1B inhibitor, antiandrogenic, or both). For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings: The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form.

Parenteral Administration: Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 μm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery: Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery.

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimes: The present methods for treating PCas are carried out by administering a therapeutic for a time and in an amount sufficient to result in decreased tumor weight, decreased tumor growth, or decreased in other incidence of PCa progression or presence.

The amount and frequency of administration of the compositions can vary depending on, for example, what is being administered, the state of the patient, and the manner of administration. In therapeutic applications, compositions can be administered to a patient suffering from PCa in an amount sufficient to relieve or least partially relieve the symptoms of the PCa and its complications. The dosage is likely to depend on such variables as the type and extent of progression of the PCa, the severity of the PCa, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the PCa or slowing its progression.

The amount of therapeutic per dose can vary. For example, a subject can receive from about 0.1 μg/kg to about 10,000 μg/kg. Generally, the therapeutic is administered in an amount such that the peak plasma concentration ranges from 150 nM-250 μM.

Exemplary dosage amounts can fall between 0.1-5000 μg/kg, 100-1500 μg/kg, 100-350 μg/kg, 340-750 μg/kg, or 750-1000 μg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 μmol of therapeutic (e.g., 0.1-25 μmol or 0.4-20 μmol).

The plasma concentration of therapeutic can also be measured according to methods known in the art. Exemplary peak plasma concentrations of therapeutic can range from 0.05-10 μM, 0.1-10 μM, 0.1-5.0 μM, or 0.1-1 μM. Alternatively, the average plasma levels of therapeutic can range from 400-1200 μM (e.g., between 500-1000 μM) or between 50-250 μM (e.g., between 40-200 μM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the PCa.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, we claim:

1. A pharmaceutical composition comprising:

(a) a first therapeutic comprising a TLK1B inhibitor, or a pharmaceutically acceptable salt, solvate, ester, amide, clathrate, stereoisomer, enantiomer, or prodrug thereof, wherein the TLK1B inhibitor is a phenothiazine (PTH) antipsychotic selected from the group consisting of: Thioridazine (THD), Perphenazine (PPH), Trifloroperazine (TFP), Promazine (PMZ), 4-(2-(10H-phenothiazin-10-yl) ethyl) morpholine (154), 10-methyl-10H-phenothiazine (J56), J3-50, J3-51, J3-54, J3-55, JS-56, J3-65, and J3-66; and (b) a second therapeutic including an antiandrogen or a pharmaceutically acceptable salt, solvate, ester, amide, clathrate, stereoisomer, enantiomer, or prodrug thereof.

2. The pharmaceutical composition of claim 1 wherein the antiandrogen is one of bicalutamide, aminoglutethimide, ketoconazole, abiraterone acetate, enzalutamide, and apalutamide.

3. The pharmaceutical composition of claim 1 wherein the antiandrogen is bicalutamide.

4. The pharmaceutical composition of claim 1 wherein the TLK1B inhibitor is J54 and the antiandrogen is one of bicalutamide, aminoglutethimide, ketoconazole, abiraterone acetate, enzalutamide, and apalutamide.

5. The pharmaceutical composition of claim 1 wherein the TLK1B inhibitor is J54 and the antiandrogen is bicalutamide.

6. The pharmaceutical composition of claim 1 wherein the TLK1B inhibitor is J3-66 and the antiandrogen is one of bicalutamide, aminoglutethimide, ketoconazole, abiraterone acetate, enzalutamide, and apalutamide.

7. The pharmaceutical composition of claim 1 wherein the TLK1B inhibitor is J3-66 and the antiandrogen is bicalutamide.

8. The pharmaceutical composition of claim 1 further comprising an excipient.

9. The pharmaceutical composition of claim 1 wherein the pharmaceutical composition is in the form of a tablet, a capsule, a liquid solution or suspension, a powder, a liquid, or solid crystals.

10. A pharmaceutical composition comprising:

(a) a first therapeutic comprising a phenothiazine (PTH) antipsychotic selected from the group consisting of: Thioridazine (THD), Perphenazine (PPH), Trifloroperazine (TFP), Promazine (PMZ), 4-(2-(10H-phenothiazin-10-yl) ethyl) morpholine (J54), 10-methyl-10H-phenothiazine (J56), J3-50, J3-51, J3-54, J3-55, JS-56, J3-65, and J3-66; and (b) a second therapeutic including an antiandrogen or a pharmaceutically acceptable salt, solvate, ester, amide, clathrate, stereoisomer, enantiomer, or prodrug thereof, wherein the antiandrogen is selected from the group consisting of bicalutamide, aminoglutethimide, ketoconazole, abiraterone acetate, enzalutamide, and apalutamide.

11. The pharmaceutical composition of claim 10 wherein the phenothiazine (PTH) antipsychotic is J54 and the antiandrogen is bicalutamide.

12. The pharmaceutical composition of claim 10 wherein the phenothiazine (PTH) antipsychotic is J3-66 and the antiandrogen is bicalutamide.

13. The pharmaceutical composition of claim 10 further comprising an excipient.

14. The pharmaceutical composition of claim 10 wherein the pharmaceutical composition is in the form of a tablet, a capsule, a liquid solution or suspension, a powder, a liquid, or solid crystals.

15. A pharmaceutical composition for treating prostate cancer, the composition comprising:

(a) a first therapeutic comprising a phenothiazine (PTH) antipsychotic, or a pharmaceutically acceptable salt, solvate, ester, amide, clathrate, stereoisomer, enantiomer, prodrug or conformer thereof; and (b) a second therapeutic including an antiandrogen or a pharmaceutically acceptable salt, solvate, ester, amide, clathrate, stereoisomer, enantiomer, prodrug or conformer thereof, wherein the antiandrogen is selected from the group consisting of bicalutamide, aminoglutethimide, ketoconazole, abiraterone acetate, enzalutamide, and apalutamide.

16. The pharmaceutical composition of claim 15 wherein the phenothiazine (PTH) antipsychotic is selected from the group consisting of: Thioridazine (THD), Perphenazine (PPH), Trifloroperazine (TFP), Promazine (PMZ), 4-(2-(10H-phenothiazin-10-yl) ethyl) morpholine (J54), 10-methyl-10H-phenothiazine (156), J3-50, J3-51, J3-54, J3-55, JS-56, J3-65, and J3-66.

17. The pharmaceutical composition of claim 16 wherein the phenothiazine (PTH) antipsychotic is J54 and the antiandrogen is bicalutamide.

18. The pharmaceutical composition of claim 16 wherein the phenothiazine (PTH) antipsychotic is J3-66 and the antiandrogen is bicalutamide.

19. The pharmaceutical composition of claim 16 further comprising an excipient.

20. The pharmaceutical composition of claim 16 wherein the pharmaceutical composition is in the form of a tablet, a capsule, a liquid solution or suspension, a powder, a liquid, or solid crystals.

* * * * *